(12) United States Patent
Jang et al.

(10) Patent No.: US 11,696,498 B2
(45) Date of Patent: Jul. 4, 2023

(54) COMPOUND FOR AN ORGANIC OPTOELECTRONIC DEVICE, ORGANIC OPTOELECTRONIC DEVICE, AND DISPLAY DEVICE USING THE SAME

(71) Applicant: SAMSUNG SDI CO., LTD., Yongin-si (KR)

(72) Inventors: Kipo Jang, Suwon-si (KR); Byungku Kim, Suwon-si (KR); Giwook Kang, Suwon-si (KR); Hanill Lee, Suwon-si (KR); Sung-Hyun Jung, Suwon-si (KR); Ho Kuk Jung, Suwon-si (KR); Youngkyoung Jo, Suwon-si (KR); Eun Sun Yu, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 619 days.

(21) Appl. No.: 16/722,853

(22) Filed: Dec. 20, 2019

(65) Prior Publication Data

US 2020/0127213 A1    Apr. 23, 2020

Related U.S. Application Data

(63) Continuation of application No. PCT/KR2018/006794, filed on Jun. 15, 2018.

(30) Foreign Application Priority Data

Jun. 22, 2017    (KR) .................. 10-2017-0079209

(51) Int. Cl.
*C09K 11/02* (2006.01)
*H10K 85/60* (2023.01)
(Continued)

(52) U.S. Cl.
CPC ......... *H10K 85/654* (2023.02); *C07D 405/14* (2013.01); *C09K 11/025* (2013.01);
(Continued)

(58) Field of Classification Search
CPC ............ H01L 51/0067; H01L 51/0072; H01L 51/0073; H01L 51/0085; H01L 51/5012; H01L 51/5016; H01L 51/5056; H01L 51/5072; H01L 51/5088; H01L 2251/5384; H01L 51/00; C07D 405/14; C09K 11/025; C09K 11/06; C09K 2211/1029;
(Continued)

(56) References Cited

U.S. PATENT DOCUMENTS 5,061,569 A    10/1991  VanSlyke
8,946,697 B1    2/2015  Ma et al.
(Continued)

FOREIGN PATENT DOCUMENTS

CN    103435597 A    12/2013
CN    106029831 A    10/2016
(Continued)

OTHER PUBLICATIONS

CAS reg. No. 2259709-50-5, Jan. 17, 2019. (Year: 2019).*
(Continued)

*Primary Examiner* — Douglas J McGinty
(74) *Attorney, Agent, or Firm* — Lee IP Law, P.C.

(57) ABSTRACT

A compound and an organic optoelectronic device, the compound being represented by Chemical Formula 1-3a-I or Chemical Formula 1-4a-I:

[Chemical Formula 1-3a-I]

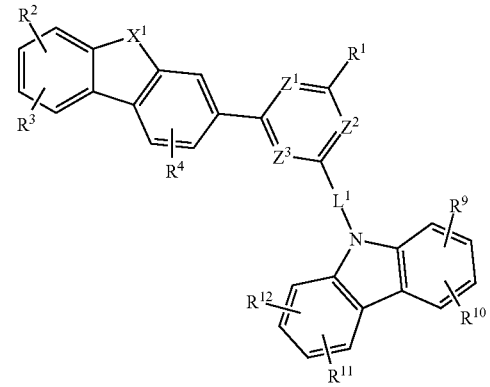

[Chemical Formula 1-4a-I]

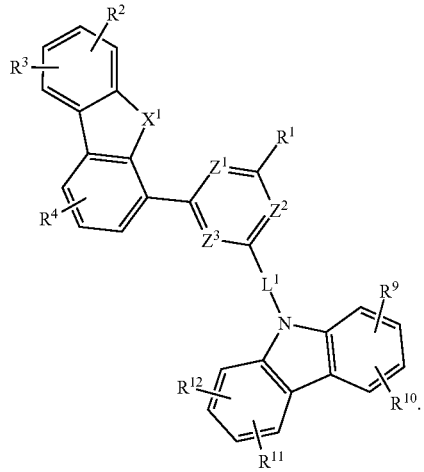

14 Claims, 1 Drawing Sheet

(51) Int. Cl.
  *C07D 405/14* (2006.01)
  *C09K 11/06* (2006.01)
  *H10K 85/30* (2023.01)
  *H10K 50/11* (2023.01)
  *H10K 50/15* (2023.01)
  *H10K 50/16* (2023.01)
  *H10K 50/17* (2023.01)
  *H10K 101/10* (2023.01)
  *H10K 101/00* (2023.01)

(52) U.S. Cl.
  CPC ............ *C09K 11/06* (2013.01); *H10K 85/342* (2023.02); *H10K 85/6572* (2023.02); *H10K 85/6574* (2023.02); *C09K 2211/1029* (2013.01); *C09K 2211/1088* (2013.01); *C09K 2211/185* (2013.01); *H10K 50/11* (2023.02); *H10K 50/15* (2023.02); *H10K 50/16* (2023.02); *H10K 50/17* (2023.02); *H10K 2101/10* (2023.02); *H10K 2101/90* (2023.02)

(58) Field of Classification Search
  CPC ...... C09K 2211/1088; C09K 2211/185; H10K 85/654; H10K 85/342; H10K 85/6572; H10K 85/6574; H10K 50/11; H10K 50/15; H10K 50/16; H10K 50/17; H10K 2101/10; H10K 2101/90; H10K 99/00
  USPC .......................................................... 428/690
  See application file for complete search history.

(56) References Cited

U.S. PATENT DOCUMENTS

| | | | |
|---|---|---|---|
| 9,397,307 B2 | 7/2016 | Nishimura | |
| 9,847,501 B2 | 12/2017 | Mizutani | |
| 10,985,329 B2 | 4/2021 | Lee | |
| 11,217,756 B2* | 1/2022 | Lui | ........... H01L 51/0073 |
| 11,223,019 B2* | 1/2022 | Lui | ........... C09K 11/06 |
| 2002/0121860 A1 | 9/2002 | Seo | |
| 2002/0182441 A1 | 12/2002 | Lamansky | |
| 2006/0022590 A1 | 2/2006 | Aziz et al. | |
| 2006/0078757 A1 | 4/2006 | Boerner et al. | |
| 2006/0088728 A1 | 4/2006 | Kwong | |
| 2007/0252516 A1 | 11/2007 | Kondakova et al. | |
| 2012/0273764 A1 | 11/2012 | Yu et al. | |
| 2014/0131676 A1 | 5/2014 | Beers | |
| 2014/0231769 A1 | 8/2014 | Nishimura | |
| 2014/0312338 A1 | 10/2014 | Mizutani | |
| 2015/0171340 A1 | 6/2015 | Lee | |
| 2015/0207079 A1 | 7/2015 | Cho et al. | |
| 2016/0049597 A1 | 2/2016 | Ma | |
| 2016/0088728 A1 | 3/2016 | Wang et al. | |
| 2016/0093808 A1 | 3/2016 | Adamovich et al. | |
| 2016/0141521 A1 | 5/2016 | Watanabe et al. | |
| 2017/0047527 A1 | 2/2017 | Lee et al. | |
| 2017/0069848 A1 | 3/2017 | Zeng | |
| 2017/0170408 A1 | 6/2017 | Park et al. | |
| 2017/0213968 A1 | 7/2017 | Park | |
| 2017/0317293 A1 | 11/2017 | Kim | |
| 2019/0198771 A1 | 6/2019 | Lui et al. | |
| 2019/0198772 A1* | 6/2019 | Lui | ........... H01L 51/0072 |
| 2019/0363261 A1 | 11/2019 | Lee et al. | |
| 2020/0127213 A1 | 4/2020 | Jang | |
| 2020/0161560 A1* | 5/2020 | Jang | ........... H01L 51/0073 |
| 2020/0161563 A1 | 5/2020 | Jang et al. | |
| 2020/0350501 A1* | 11/2020 | Lui | ........... H01L 51/0073 |
| 2021/0135118 A1 | 5/2021 | Son | |
| 2022/0140251 A1* | 5/2022 | Lui | ........... H01L 51/0073 257/40 |

FOREIGN PATENT DOCUMENTS

| | | |
|---|---|---|
| CN | 106575663 A | 4/2017 |
| CN | 107337650 A | 11/2017 |
| JP | 059471 A | 1/1993 |
| JP | 0525473 A | 2/1993 |
| JP | 07126615 A | 5/1995 |
| JP | 1095973 A | 4/1998 |
| JP | 2003-133075 A | 5/2003 |
| JP | 5206907 B2 | 6/2013 |
| JP | 5338184 B2 | 11/2013 |
| JP | 5707665 B2 | 4/2015 |
| JP | 2017-503338 A | 1/2017 |
| JP | 2017-513220 A | 5/2017 |
| JP | 2017/175099 A | 9/2017 |
| KR | 10-2013-0074765 | 7/2013 |
| KR | 10-2013-0131230 | 12/2013 |
| KR | 10-2014-0046541 | 4/2014 |
| KR | 20140083897 A | 7/2014 |
| KR | 10-2014-0144550 | 12/2014 |
| KR | 10-2015-0042335 | 4/2015 |
| KR | 10-2015-0070860 | 6/2015 |
| KR | 10-2016-0010333 | 1/2016 |
| KR | 10-2016-0010373 | 1/2016 |
| KR | 10-2016-0011036 | 1/2016 |
| KR | 10-2016-0060539 | 5/2016 |
| KR | 10-2016-0064955 | 6/2016 |
| KR | 10-2016-0069934 | 6/2016 |
| KR | 10-2017-0037276 | 4/2017 |
| KR | 10-1744248 | 5/2017 |
| KR | 10-2017-0113318 | 10/2017 |
| KR | 10-2018-0007617 | 1/2018 |
| KR | 10-2018-0010808 | 1/2018 |
| KR | 10-2018-0013449 | 2/2018 |
| KR | 10-2018-0069475 | 6/2018 |
| KR | 10-2019-0045436 A | 5/2019 |
| KR | 10-2019-0058748 A | 5/2019 |
| WO | WO 9509147 A1 | 4/1995 |
| WO | WO 2004/055921 A2 | 7/2004 |
| WO | WO 2012/070233 A1 | 5/2012 |
| WO | WO 2012/108881 A1 | 8/2012 |
| WO | WO 2013/077352 A1 | 5/2013 |
| WO | WO 2013/077362 A1 | 5/2013 |
| WO | WO 2014/054912 A1 | 4/2014 |
| WO | WO 2016-013867 A1 | 1/2016 |
| WO | WO-2016010402 A1 * | 1/2016 ........... C09K 11/025 |
| WO | WO 2016-080791 A1 | 5/2016 |
| WO | WO 2016-208873 A1 | 12/2016 |
| WO | WO 2018/016724 A1 | 1/2018 |
| WO | WO 2018/038400 A1 | 3/2018 |
| WO | WO 2018/048074 A1 | 3/2018 |
| WO | WO 2018110958 A1 | 6/2018 |
| WO | WO 2018/194278 A2 | 10/2018 |
| WO | WO2018/236094 A1 | 12/2018 |
| WO | WO 2019/083215 A1 | 5/2019 |
| WO | WO 2020157204 A1 | 8/2020 |

OTHER PUBLICATIONS

U.S. Office action received in co pending related U.S. Appl. No. 16/285,617.
European Office action dated Nov. 13, 2020.
Japanese Office action dated Dec. 15, 2020.
Office action received in U.S. Appl. No. 16/285,711 dated Jun. 25, 2020.
USPTO Advisory action dated Mar. 30, 2020 for U.S. Appl. No. 16/269,700.
U.S. Office action received in co pending related U.S. Appl. No. 16/269,700 dated Apr. 22, 2021.
U.S. Office action received in co pending related U.S. Appl. No. 16/285,711 dated Mar. 4, 2021.
U.S. Patent Office Action received in Co pending U.S. Appl. No. 16/930,406 dated Jun. 24, 2021.
Office action received in co-pending U.S. Appl. No. 16/285,617 dated Oct. 16, 2020.
U.S. Office action received in Co pending U.S. Appl. No. 16/930,406 dated Mar. 3, 2022.
Office action received in co pending U.S. Appl. No. 16/285,617 dated Nov. 13, 2020.
Office action received in co pending U.S. Appl. No. 16/269,700 dated Oct. 29, 2020.

(56) References Cited

OTHER PUBLICATIONS

Chinese Office action dated Mar. 24, 2020.
Office Action received in U.S. Appl. No. 16/285,711 dated Jan. 13, 2020.
Office Action received in U.S. Appl. No. 16/285,617 dated Jan. 13, 2020.
Office Action received in U.S. Appl. No. 16/269,700 dated Dec. 20, 2019.
U.S. Appl. No. 16/269,700, filed Feb. 7, 2019.
U.S. Appl. No. 16/285,617, filed Feb. 26, 2019.
U.S. Appl. No. 16/285,711, filed Feb. 26, 2019.
U.S. Appl. No. 16/619,677, filed Dec. 5, 2019.
Gong, "Tuning the Photophysical Properties and Energy Levels by Linking Spacer, etc." Journal of Physical Chemistry C, 2010, vol. 114, pp. 5193-5198.
Third party submission dated Aug. 21, 2019.
U.S. Advisory action received in co pending U.S. Appl. No. 16/930,406, dated May 25, 2022.
U.S. Office action received in co pending U.S. Appl. No. 16/619,677 dated Jun. 8, 2022.
U.S. Office action received in copending U.S. Appl. No. 16/285,711 dated Sep. 20, 2021.
U.S. Office action received in U.S. Appl. No. 16/619,677, dated Dec. 1, 2022.
Chinese Search Report dated Sep. 9, 2022.
U.S. Office action received in co pending related U.S. Appl. No. 16/930,406, dated Sep. 2, 2022.
U.S. Office action received in copending related U.S. Appl. No. 16/930,406, dated Mar. 16, 2023.
U.S. Office received in copending related U.S. Appl. No. 17/569,012, dated Mar. 31, 2023.

\* cited by examiner

[Figure 1]
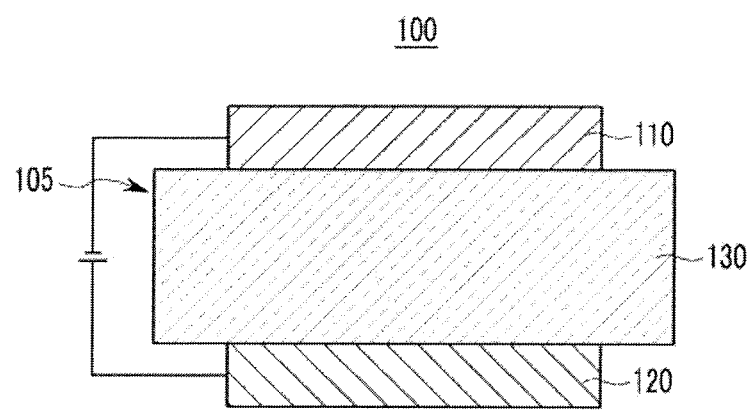
[Figure 2]
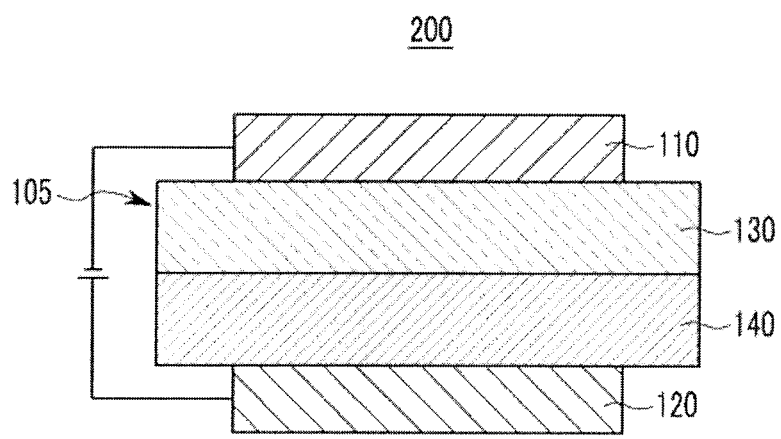

COMPOUND FOR AN ORGANIC OPTOELECTRONIC DEVICE, ORGANIC OPTOELECTRONIC DEVICE, AND DISPLAY DEVICE USING THE SAME

CROSS-REFERENCE TO RELATED APPLICATION

This application is a continuation of pending International Application No. PCT/KR2018/006794, entitled "Organic Optoelectronic Device and Display Device Using the Same," which was filed on Jun. 15, 2018, the entire contents of which are hereby incorporated by reference.

Korean Patent Application No. 10-2017-0079209, filed on Jun. 22, 2017, in the Korean Intellectual Property Office, and entitled: "Organic Optoelectronic Device and Display Device Using the Same," is incorporated by reference herein in its entirety.

BACKGROUND

1. Field

Embodiments relate to a compound for an organic optoelectronic device, an organic optoelectronic device and a display device.

2. Description of the Related Art

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device that converts electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example, at least one layer selected from a hole injection layer, a hole transport layer, an electron blocking layer, an electron transport layer, an electron injection layer, and a hole blocking layer.

SUMMARY

The embodiments may be realized by providing a compound for an organic optoelectronic device, the compound being represented by Chemical Formula 1-3a-I or Chemical Formula 1-4a-I,

[Chemical Formula 1-3a-I]

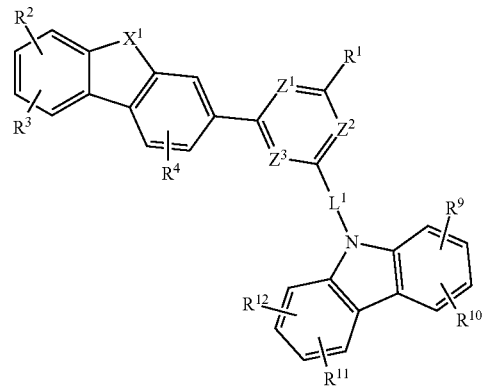

[Chemical Formula 1-4a-I]

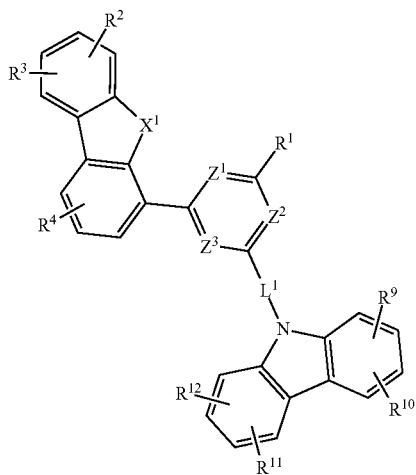

wherein, in Chemical Formulae 1-3a-I and 1-4a-I, $X^1$ is O or S, $Z^1$ to $Z^3$ are each independently N or $CR^a$, at least two of $Z^1$ to $Z^3$ are N, $L^1$ is a single bond, or a substituted or unsubstituted C6 to C20 arylene group, $R^1$ is a substituted or unsubstituted C6 to C20 aryl group, a substituted or unsubstituted dibenzofuranyl group, or a substituted or unsubstituted dibenzothiophenyl group, and $R^a$, $R^2$ to $R^4$ and $R^9$ to $R^{13}$ are independently hydrogen, deuterium, a cyano group, a substituted or unsubstituted C1 to C10 alkyl group, or a substituted or unsubstituted C6 to C20 aryl group.

In Chemical Formulae 1-3a-I and 1-4a-I, $Z^1$ to $Z^3$ may be N.

In Chemical Formulae 1-3a-I and 1-4a-I, $R^1$ may be a substituent of Group I:

[Group I]

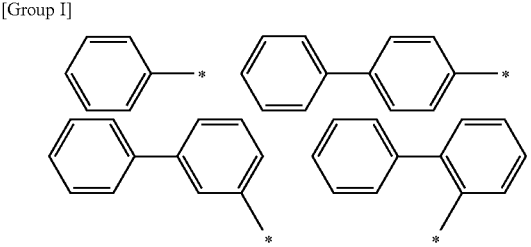

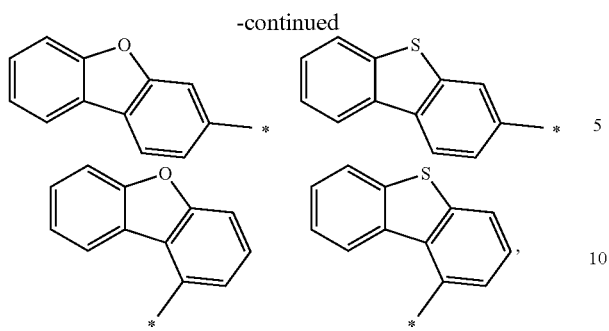

and in Group I, * is a linking point.

In Chemical Formulae 1-3a-I and 1-4a-I, $L^1$ may be a single bond, a C6 arylene group, a C12 arylene group or a C18 arylene group.

In Chemical Formulae 1-3a-I and 1-4a-I, $L^1$ may be a single bond, or an unsubstituted C6 arylene group.

In Chemical Formulae 1-3a-I and 1-4a-I, $R^1$ may be an unsubstituted C6 aryl group.

The compound may be represented by Chemical Formula 1-3a-I, and in Chemical Formula 1-4a-I, $X^1$ may be O, $Z^1$ to $Z^3$ may each be N, $L^1$ may be a single bond, or an unsubstituted C6 arylene group, $R^1$ may be an unsubstituted C6 aryl group, and $R^2$ to $R^4$ and $R^9$ to $R^{13}$ may each be hydrogen.

The embodiments may be realized by providing an organic optoelectronic device including an anode and a cathode facing each other; and an organic layer between the anode and the cathode, wherein the organic layer includes a light emitting layer and at least one of a hole injection layer, a hole transport layer, and an electron transport layer, and wherein the light emitting layer includes the compound according to an embodiment as a host.

The embodiments may be realized by providing an organic optoelectronic device, wherein the light emitting layer further includes a second host represented by Chemical Formula 2:

[Chemical Formula 2]

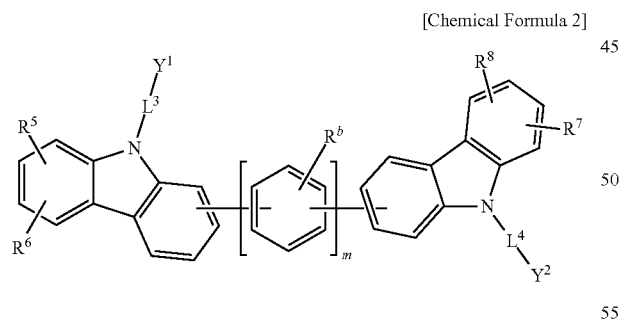

wherein, in Chemical Formula 2, $Y^1$ and $Y^2$ are each independently a substituted or unsubstituted C6 to C20 aryl group or a substituted or unsubstituted C2 to C30 heterocyclic group, $L^3$ and $L^4$ are each independently a single bond or a substituted or unsubstituted C6 to C20 arylene group, $R^b$ and $R^5$ to $R^8$ are each independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group, and m is an integer ranging from 0 to 2.

Chemical Formula 2 may include a moiety of Group II, and *-$L^3$-$Y^1$ and *-$L^4$-$Y^2$ are each independently a substituent of Group III:

[Group II]

C-1

C-2

C-3

C-4

C-5

C-6

C-7
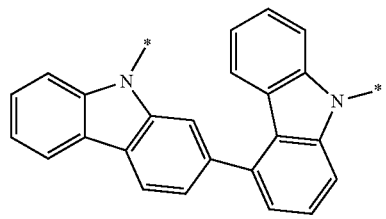
C-8
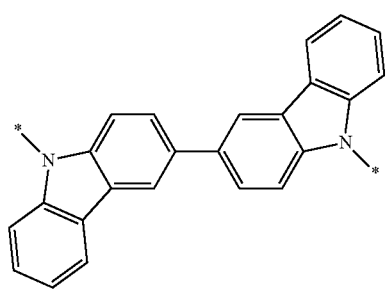
C-9
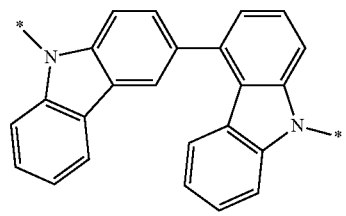
C-10
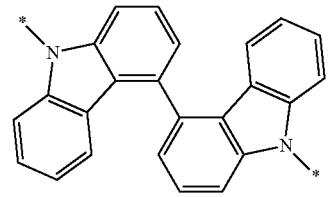
C-11
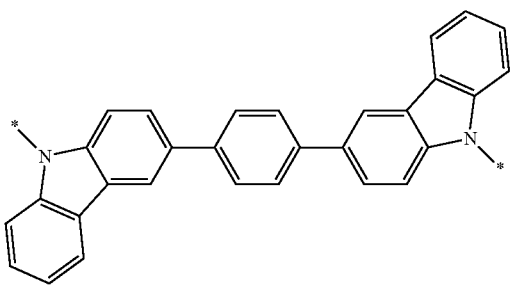
C-12
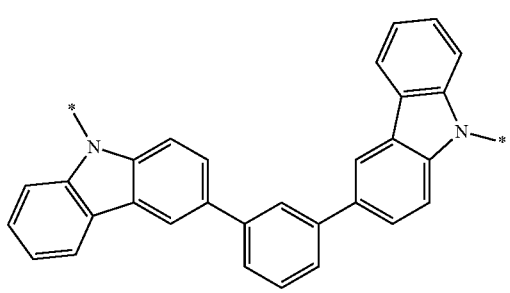
C-13
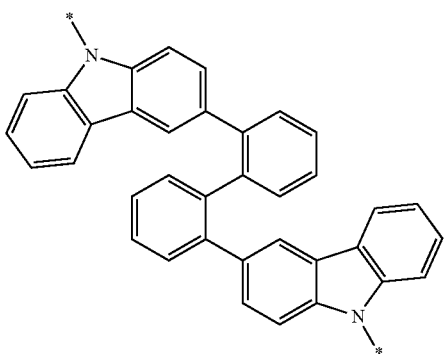
C-14
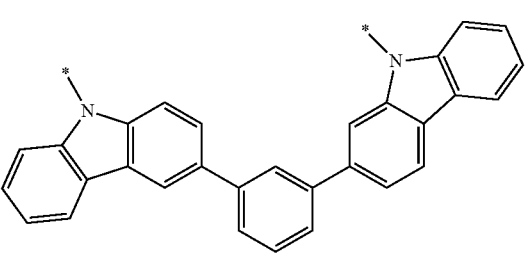
C-15
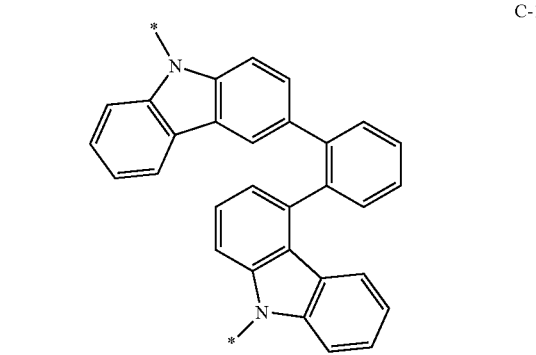
C-16
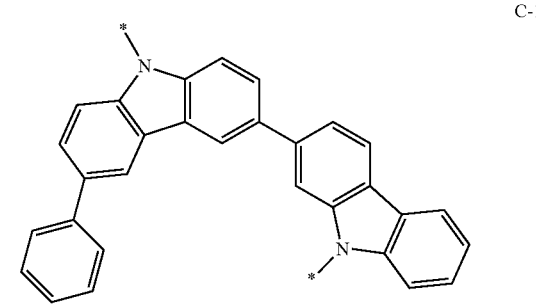
C-17
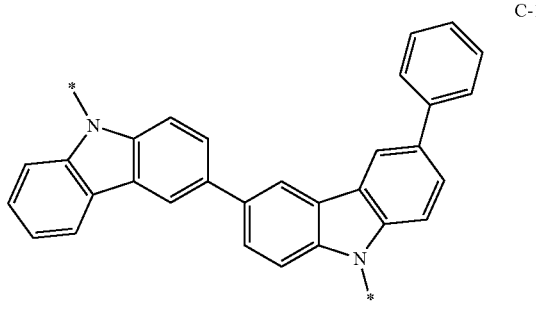

-continued
C-18
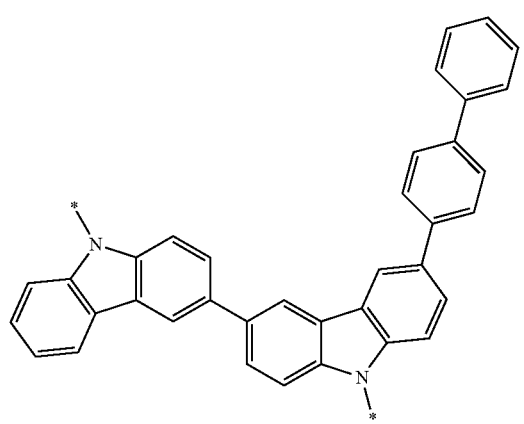
[Group III]
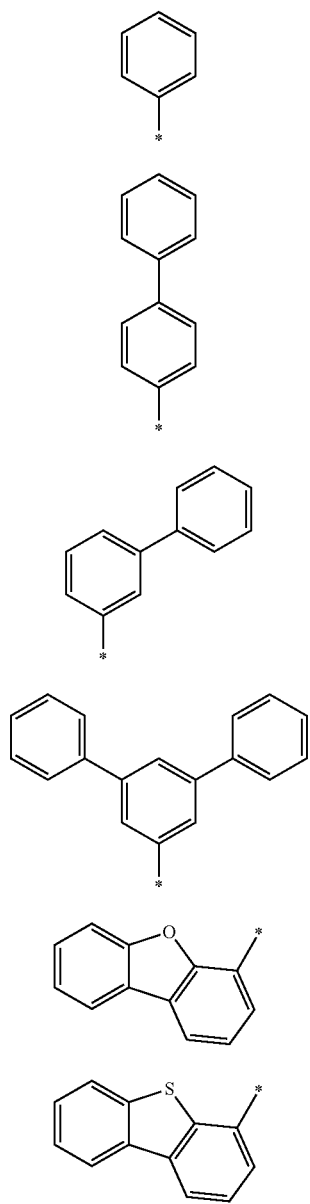
B-1
B-2
B-3
B-4
B-5
B-6
-continued
B-7
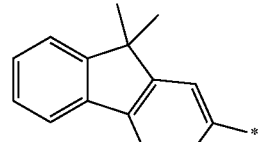
B-8
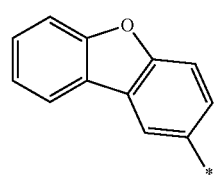
B-9
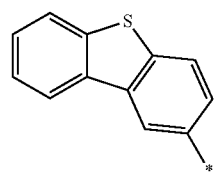
B-10
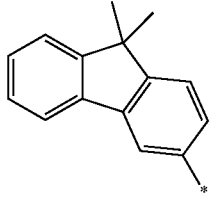
B-11
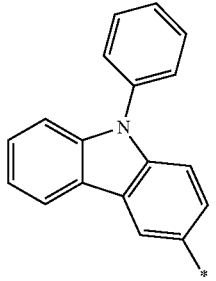
B-12
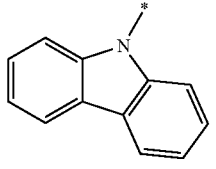
B-13
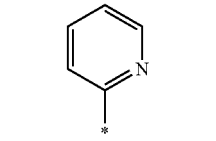
B-14
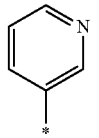

B-15 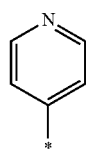
B-16 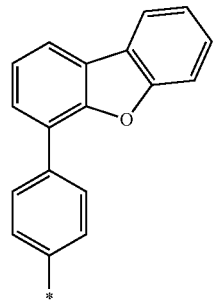
B-17 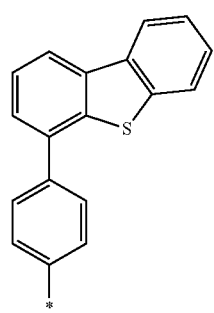
B-18 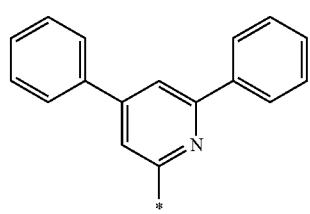
B-19 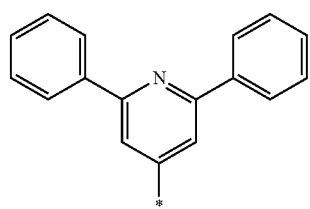
B-20 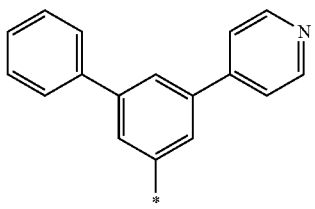
B-21 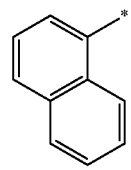
B-22 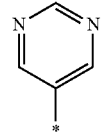
B-23 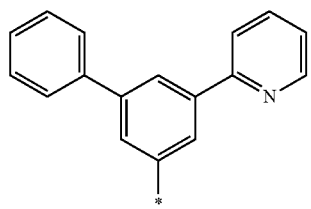
B-24 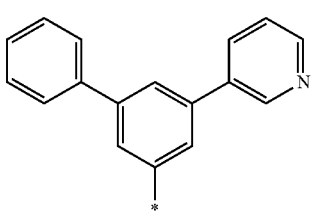
B-25 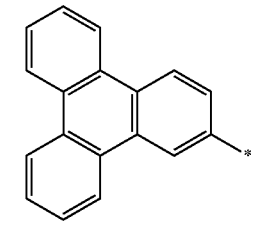
B-26 
B-27
B-28
wherein, in Group II and Group III, * is a linking point.

Chemical Formula 2 may include a moiety represented by Chemical Formula c-8 or Chemical Formula c-17 of Group II, and *-$L^3$-$Y^1$ and *-$L^4$-$Y^2$ may each independently be a substituent of Group III.

Chemical Formula 2 may include a moiety represented by Chemical Formula c-8 or Chemical Formula c-17 of Group II, and *-$L^3$-$Y^1$ and *-$L^4$-$Y^2$ may each independently be a substituent represented by B-1, B-2, B-3, B-11, B-16, or B-17 of Group III.

The second host represented by Chemical Formula 2 may be represented by Chemical Formula 2A:

[Chemical Formula 2A]

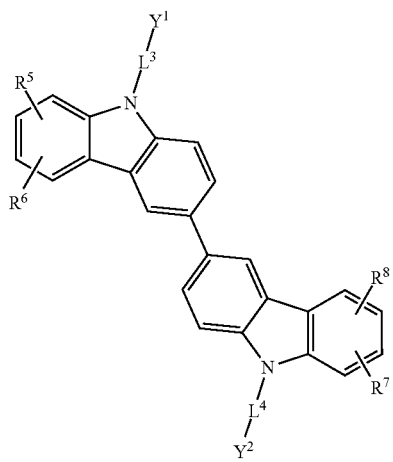

wherein, in Chemical Formula 2A, $L^3$ and $L^4$ are each independently a single bond, or a substituted or unsubstituted C6 to C20 arylene group, $R^a$ and $R^2$ to $R^8$ are each independently hydrogen, deuterium, a cyano group, a substituted or unsubstituted C1 to C10 alkyl group, or a substituted or unsubstituted C6 to C20 aryl group, and $Y^1$ and $Y^2$ are each independently a substituted or unsubstituted C6 to C20 aryl group, or a substituted or unsubstituted C2 to C30 heterocyclic group.

In Chemical Formula 2, m may be 0, $Y^1$ and $Y^2$ may each be an unsubstituted C6 aryl group, $L^3$ and $L^4$ may each be an unsubstituted C6 arylene group, $R^5$ to $R^8$ may each be hydrogen.

The second host represented by Chemical Formula 2 may be the following compound D-99:

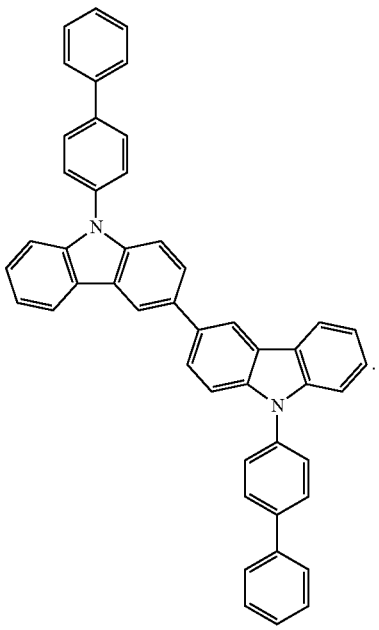

D-99

The embodiments may be realized by providing a display device comprising the organic optoelectronic device according to an embodiment.

BRIEF DESCRIPTION OF THE DRAWINGS

Features will be apparent to those of skill in the art by describing in detail example embodiments with reference to the attached drawings, in which:

FIGS. 1 and 2 illustrate cross-sectional views showing organic light emitting diodes according to embodiments.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

In the present specification when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C10 alkyl group, a C6 to C20 aryl group, or a C2 to C20 heterocyclic group. In addition, in specific examples, "substituted" refers to replacement of at least one hydrogen of a substituent or a compound by deuterium, a C1 to C4 alkyl group, a C6 to C12 aryl group, or a C2 to C12 heterocyclic group. More specifically, "substituted" refers to replacement of at least one hydrogen of a substituent or a compound by deuterium, a C1 to C5 alkyl group, a phenyl group, a biphenyl group, a terphenyl group, a naphthyl group, a benzofuranyl group, a benzothiophenyl group, a dibenzofuranyl group, a dibenzothiophenyl group, or a carbazolyl group. In addition, in most specific examples, "substituted" refers to replacement of at least one hydrogen of a substituent or a compound by deuterium, a methyl group, an ethyl group, a propanyl group, a butyl group, a phenyl group, a para-biphenyl group, a meta-biphenyl group, a dibenzofuranyl group, a dibenzothiophenyl group, or a carbazolyl group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic, or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or combination thereof.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, a substituted or unsubstituted dibenzothiophenyl group, or combination thereof.

In the present specification, hole characteristics refer to an ability to donate an electron to form a hole when an electric field is applied and that a hole formed in the anode may be easily injected into the light emitting layer, a hole formed in the light emitting layer may be easily transported into the anode, and a hole may be easily transported in the light emitting layer due to conductive characteristics according to a highest occupied molecular orbital (HOMO) level.

In addition, electron characteristics refer to an ability to accept an electron when an electric field is applied and that an electron formed in the cathode may be easily injected into the light emitting layer, an electron formed in the light emitting layer may be easily transported into the cathode, and an electron may be easily transported in the light emitting layer due to conductive characteristics according to a lowest unoccupied molecular orbital (LUMO) level.

Hereinafter, an organic optoelectronic device according to an embodiment is described.

The organic optoelectronic device may be any device to convert electrical energy into photoenergy and vice versa without particular limitation and may be, for example, an organic photoelectric device, an organic light emitting diode, an organic solar cell, and an organic photo conductor drum, and the like.

Herein, an organic light emitting diode as one example of an organic optoelectronic device is described, referring to the drawings.

FIGS. 1 and 2 illustrate cross-sectional views showing organic light emitting diodes according to embodiments.

Referring to FIG. 1, an organic light emitting diode 100 according to an embodiment may include an anode 120 and a cathode 110 facing each other and an organic layer 105 interposed between the anode 120 and cathode 110.

The anode 120 may be made of a conductor having a large work function to facilitate hole injection, and may be, e.g., metal, metal oxide and/or a conductive polymer. The anode 120 may be, e.g., a metal such as nickel, platinum, vanadium, chromium, copper, zinc, gold and the like or an alloy thereof; metal oxide such as zinc oxide, indium oxide, indium tin oxide (ITO), indium zinc oxide (IZO), and the like; a combination of a metal and an oxide such as ZnO and Al or SnO$_2$ and Sb; a conductive polymer such as poly(3-methylthiophene), poly(3,4-(ethylene-1,2-dioxy)thiophene) (PEDOT), polypyrrole, and polyaniline.

The cathode 110 may be made of a conductor having a small work function to facilitate electron injection, and may be, e.g., metal, metal oxide and/or a conductive polymer. The cathode 110 may be, e.g., a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, LiO$_2$/Al, LiF/Ca, LiF/Al and BaF$_2$/Ca.

The organic layer 105 may include a light emitting layer 130.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, e.g., a hole transport layer, a hole injection layer, and/or an electron blocking layer and may include at least one layer.

In an implementation, the organic layer 105 may further include, e.g., an electron injection layer, an electron transport layer, an electron transport auxiliary layer, a hole transport layer, a hole transport auxiliary layer, a hole injection layer, or a combination thereof.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

An organic optoelectronic device according to an embodiment may include an anode and a cathode facing each other, and an organic layer between the anode and the cathode.

The organic layer may include at least one of a hole injection layer, a hole transport layer, a light emitting layer, and an electron transport layer. The light emitting layer may include a first host represented by Chemical Formula 1, a second host represented by Chemical Formula 2, and a phosphorescent dopant.

[Chemical Formula 1]

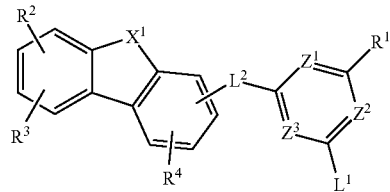

[Chemical Formula 2]

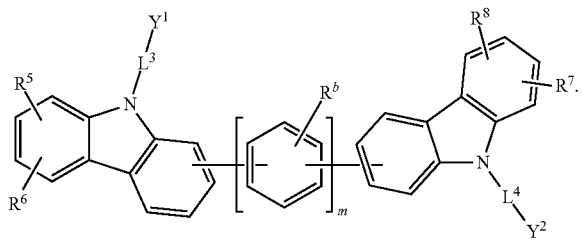

In Chemical Formula 1,
X$^1$ may be O or S,
Z$^1$ to Z$^3$ may each independently be N or CR$^a$,
at least two of Z$^1$ to Z$^3$ are N,
L$^1$ and L$^2$ may each independently be a single bond, or a substituted or unsubstituted C6 to C20 arylene group,
A may be a substituted or unsubstituted carbazolyl group,
R$^1$ may be a substituted or unsubstituted C6 to C20 aryl group, a substituted or unsubstituted dibenzofuranyl group, or a substituted or unsubstituted dibenzothiophenyl group, and
R$^a$ (e.g., of CR$^a$ in Z$^1$ to Z$^3$, above) and R$^2$ to R$^4$ may each independently be hydrogen, deuterium, a cyano group, a substituted or unsubstituted C1 to C10 alkyl group, or a substituted or unsubstituted C6 to C20 aryl group.

In Chemical Formula 2,
Y$^1$ and Y$^2$ may each independently be a substituted or unsubstituted C6 to C20 aryl group, or a substituted or unsubstituted C2 to C30 heterocyclic group,
L$^3$ and L$^4$ may each independently be a single bond or a substituted or unsubstituted C6 to C20 arylene group,
R$^b$ and R$^5$ to R$^8$ may each independently be hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group, and
m may be an integer ranging from 0 to 2.

The organic optoelectronic device according to an embodiment may increase material stability by introducing a triazine or pyrimidine moiety linked with dibenzofuran (or dibenzothiophene) and simultaneously introducing a carbazole moiety to obtain additional stability due to bipolar characteristics as the first host. A glass transition temperature relative to a molecular weight due to the carbazole moiety may be improved, and thus heat resistance may be ensured.

For example, biscarbazole may be combined as the second host and thereby holes and electrons may be balanced to realize long life-span and low driving voltage characteristics.

Simultaneously, a phosphorescent dopant may be additionally combined and thereby combination matching such as packing of host and dopant materials, energy transfer, and the like may be ensured.

The first host represented by Chemical Formula 1 may be, e.g., represented by one of Chemical Formula 1-1 to Chemical Formula 1-4 according to a specific linking position of dibenzofuran (or dibenzothiophene) with the nitrogen-containing hexagonal ring through $L^2$.

In an implementation, Chemical Formula 1-1 may be, e.g., represented by one of Chemical Formula 1-1a, Chemical Formula 1-1b, and Chemical Formula 1-1c according to $L^2$.

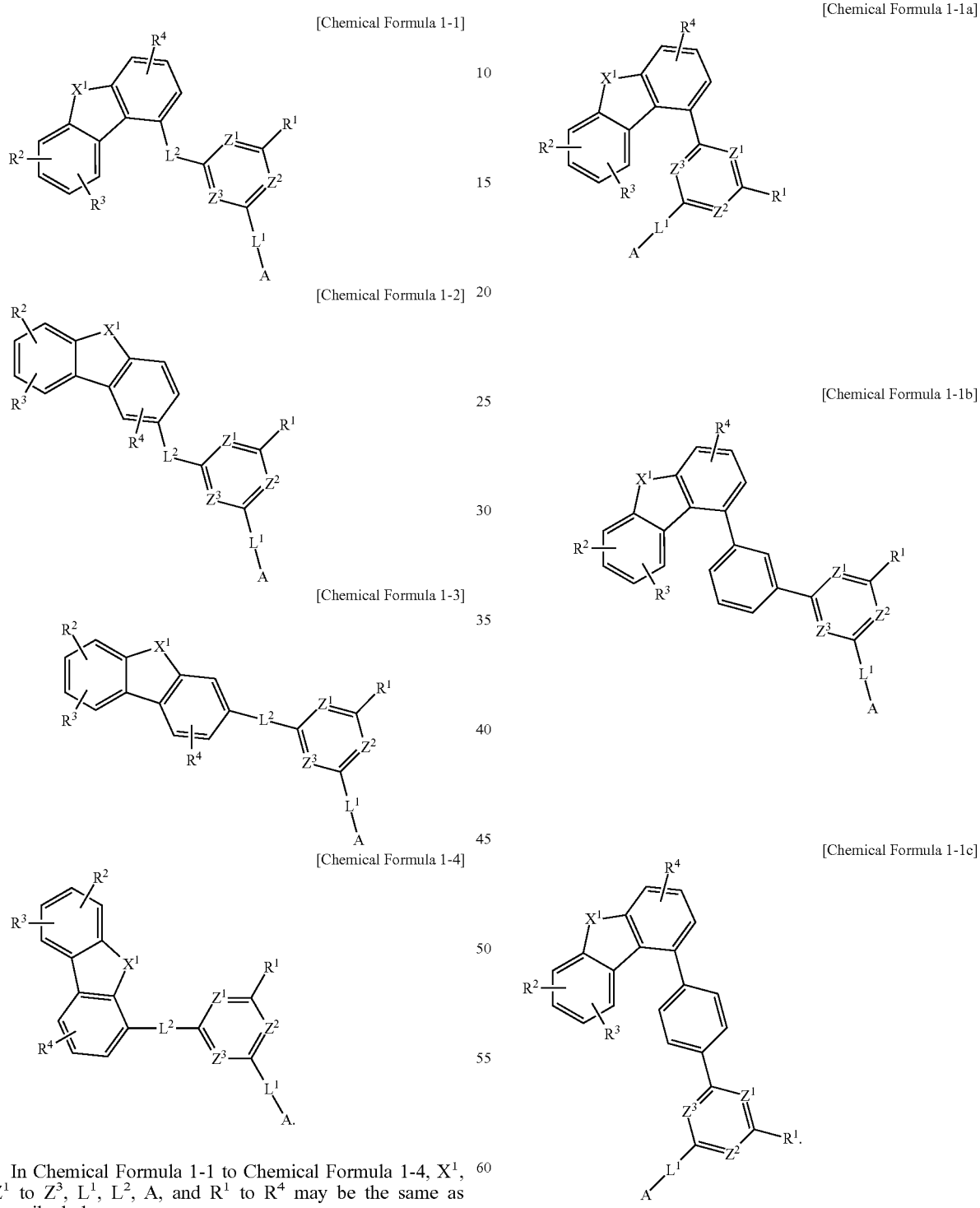

In Chemical Formula 1-1 to Chemical Formula 1-4, $X^1$, $Z^1$ to $Z^3$, $L^1$, $L^2$, A, and $R^1$ to $R^4$ may be the same as described above.

In an implementation, the first host may be represented by, e.g., Chemical Formula 1-1, Chemical Formula 1-3, or Chemical Formula 1-4. In an implementation, the first host may be represented by, e.g., Chemical Formula 1-3 or Chemical Formula 1-4.

In an implementation, Chemical Formula 1-2 may be, e.g., represented by one of Chemical Formula 1-2a, Chemical Formula 1-2b and Chemical Formula 1-2c according to $L^2$.

[Chemical Formula 1-2a]

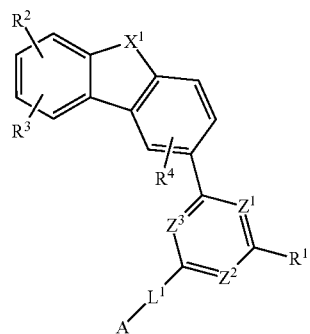

[Chemical Formula 1-3a]

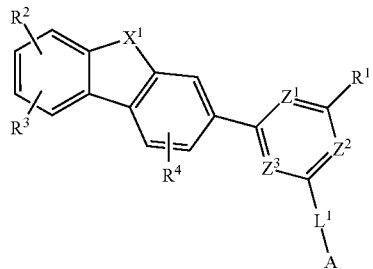

[Chemical Formula 1-2b]

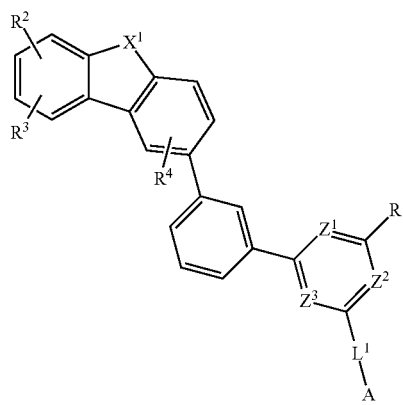

[Chemical Formula 1-3b]

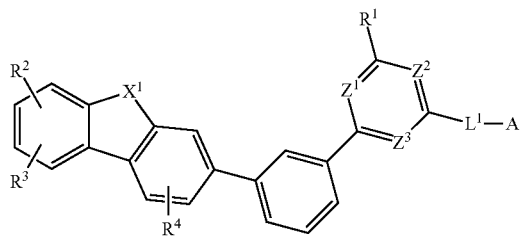

[Chemical Formula 1-3c]

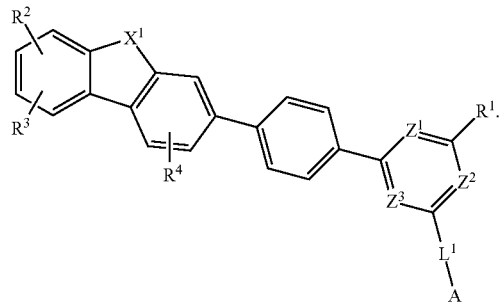

[Chemical Formula 1-2c]

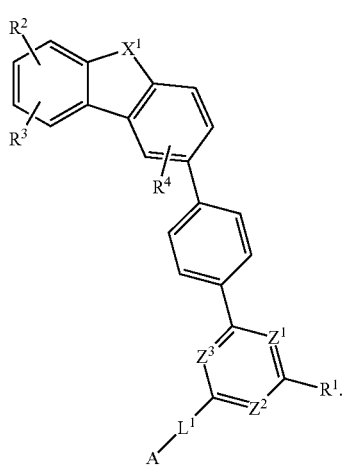

In an implementation, Chemical Formula 1-4 may be, e.g., represented by one of Chemical Formula Chemical Formula 1-4a, Chemical Formula 1-4b, and Chemical Formula 1-4c according to $L^2$.

[Chemical Formula 1-4a]

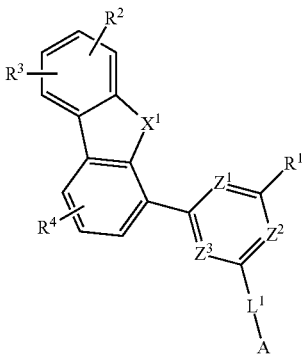

In an implementation, Chemical Formula 1-3 may be, e.g., represented by one of Chemical Formula 1-3a, Chemical Formula 1-3b, and Chemical Formula 1-3c according to $L^2$.

[Chemical Formula 1-4b]

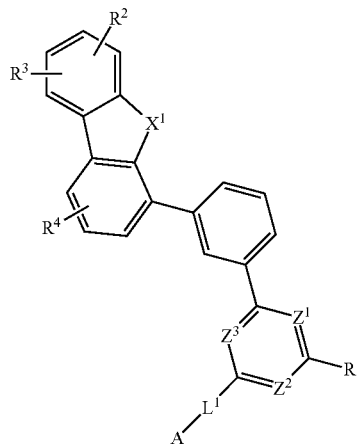

[Chemical Formula 1-4c]

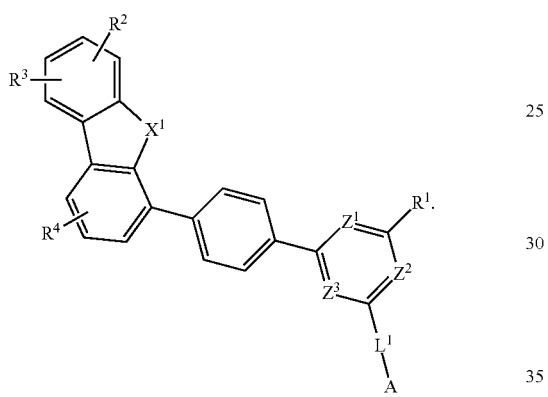

In Chemical Formula 1-1a to Chemical Formula 1-1c, Chemical Formula 1-2a to Chemical Formula 1-2c, Chemical Formula 1-3a to Chemical Formula 1-3c, and Chemical Formula 1-4a to Chemical Formula 1-4c, $X^1$, $Z^1$ to $Z^3$, $L^1$, A, and $R^1$ to $R^4$ may be the same as described above.

In an implementation, the first host may be represented by one of Chemical Formulae 1-1a, 1-3a, and 1-4b, e.g., one of Chemical Formulae 1-3a, 1-4a, and 1-4b, and for example, Chemical Formula 1-3a wherein a position No. 3 of dibenzofuran (or dibenzothiophene) is directly linked to a nitrogen-containing hexagonal ring.

The first host may help increase a hole and electron injection rate through a LUMO expansion and a planarity expansion of an ET moiety such as triazine, pyrimidine, and the like by including a structure where 3-dibenzofuran (or 3-dibenzothiophene) is directly linked with the triazine or pyrimidine moiety as shown in Chemical Formula 1-3a and secures additional stability and improves a glass transition temperature relative to a molecular weight and thus secures heat resistance by introducing a carbazole moiety to apply bipolar characteristics.

In addition, biscarbazole as a second host may be combined with the first host material to balance the first host material having fast and stable electron transport characteristics and the second host material having fast and stable hole transport characteristics and thus to secure a low driving voltage/long life-span host set having a high glass transition temperature relative to a molecular weight.

Simultaneously, the host set may be combined with a phosphorescent dopant to secure a combination/matching advantage of packing of the host and dopant materials, an energy transport, and the like and thereby obtain characteristics of a low driving voltage, a long life-span, and high efficiency.

In an implementation, the substituent A may be a substituted or unsubstituted carbazolyl group, and may be represented by one of Chemical Formula A-1 to Chemical Formula A-5 according to specific substitution points.

[Chemical Formula A-1]

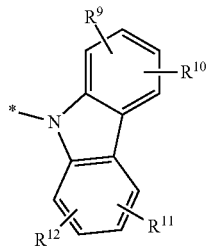

[Chemical Formula A-2]

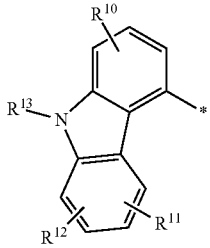

[Chemical Formula A-3]

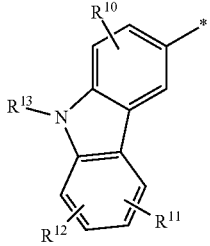

[Chemical Formula A-4]

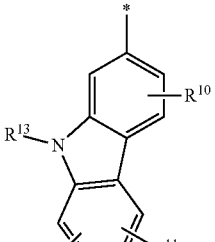

[Chemical Formula A-5]

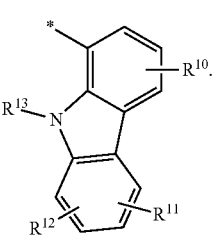

In Chemical Formula A-1 to Chemical Formula A-5, $R^9$ to $R^{13}$ may each independently be hydrogen, deuterium, a cyano group, a substituted or unsubstituted C1 to C10 alkyl group, or a substituted or unsubstituted C6 to C20 aryl group, and * is a linking point with $L^1$.

In an implementation, $R^9$ to $R^{13}$ may each independently be hydrogen, or a substituted or unsubstituted C6 to C20 aryl group, e.g., $R^9$ to $R^{13}$ may each independently be hydrogen or a phenyl group.

For example, when A is represented by Chemical Formula A-1, $R^9$ to $R^{12}$ may be all hydrogen or one or two of $R^9$ to $R^{12}$ may be a phenyl group.

In an implementation, when A is represented by one of Chemical Formula A-2 to Chemical Formula A-5, $R^{13}$ may be a phenyl group and $R^{10}$ to $R^{12}$ are all hydrogen or at least one of $R^{11}$ and $R^{12}$ may be a phenyl group.

In an implementation, Chemical Formula 1-3a may be, e.g., represented by one of Chemical Formula 1-3a-I, Chemical Formula 1-3a-II, Chemical Formula 1-3a-III, Chemical Formula 1-3a-IV, and Chemical Formula 1-3a-V according to specific structure of the substituent A.

Chemical Formula 1-4a may be, e.g., represented by one of Chemical Formula 1-4a-I, Chemical Formula 1-4a-II, Chemical Formula 1-4a-III, Chemical Formula 1-4a-IV and Chemical Formula 1-4a-V according to specific structure of the substituent A.

Chemical Formula 1-4b may be, e.g., represented by one of Chemical Formula 1-4b-I, Chemical Formula 1-4b-II, Chemical Formula 1-4b-III, Chemical Formula 1-4b-IV and Chemical Formula 1-4b-V according to specific structure of the substituent A.

[Chemical Formula 1-3a-I]

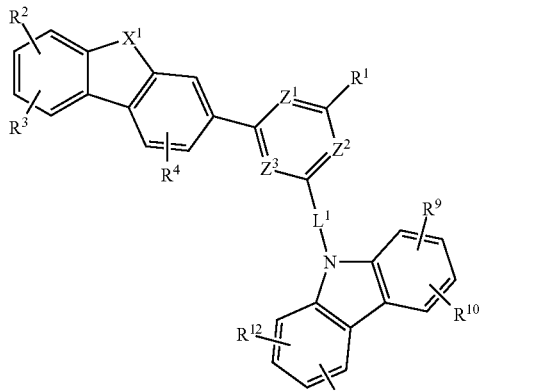

[Chemical Formula 1-3a-II]

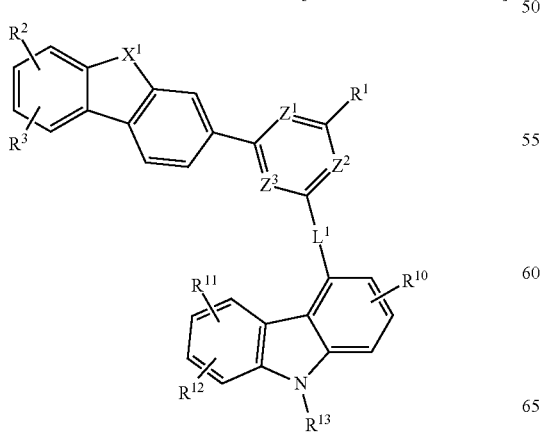

[Chemical Formula 1-3a-III]

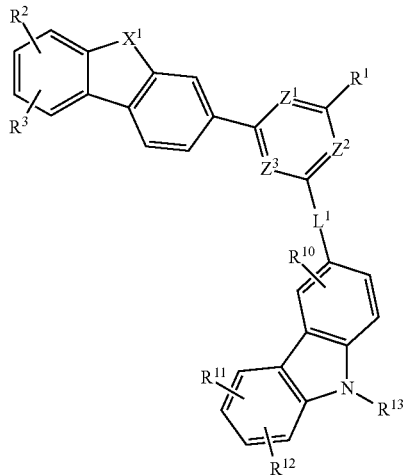

[Chemical Formula 1-3a-IV]

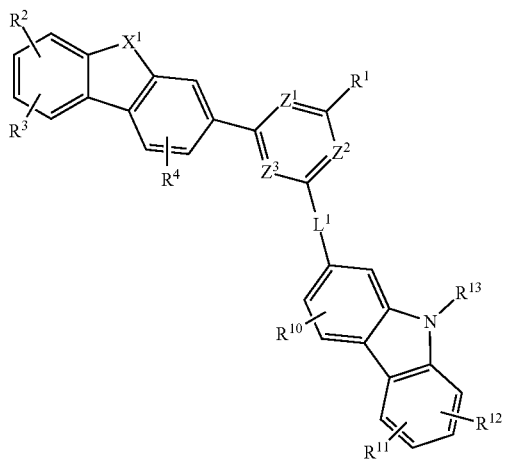

[Chemical Formula 1-3a-V]

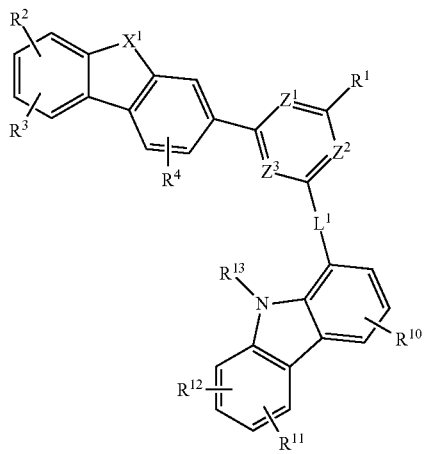

[Chemical Formula 1-4a-I]
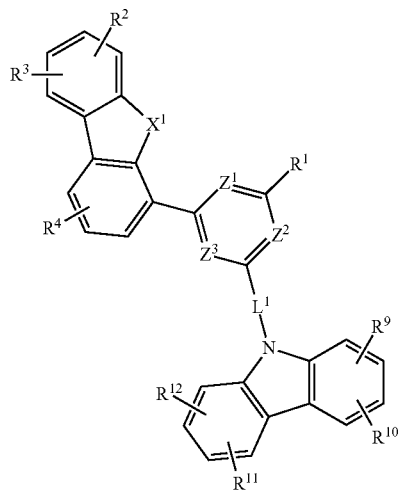
[Chemical Formula 1-4a-II]
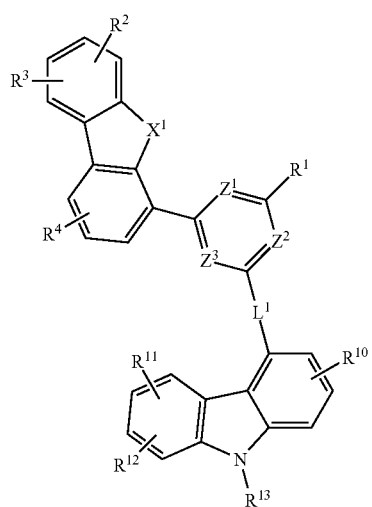
[Chemical Formula 1-4a-III]
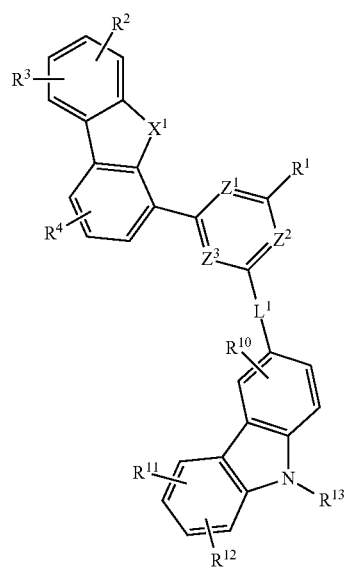
[Chemical Formula 1-4a-IV]
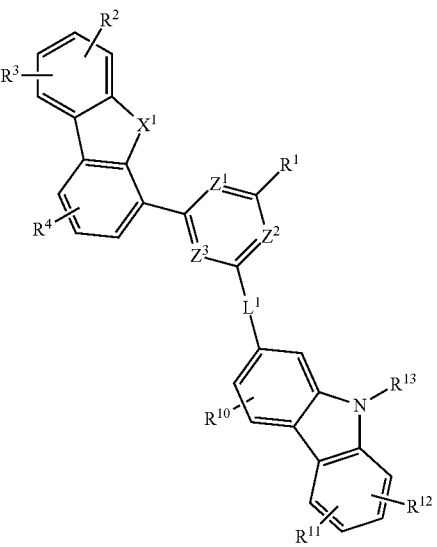
[Chemical Formula 1-4a-V]
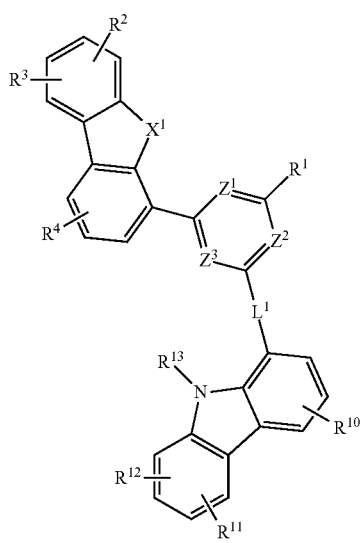

[Chemical Formula 1-4b-I]
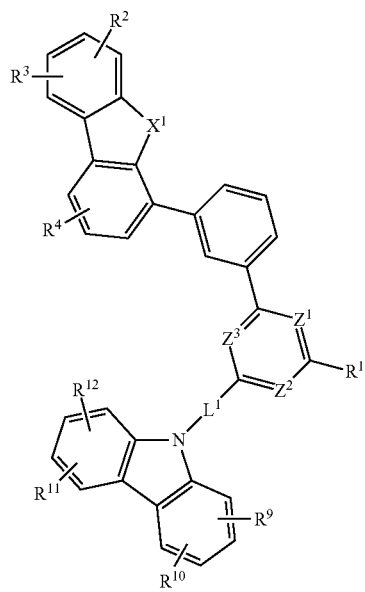
[Chemical Formula 1-4b-II]
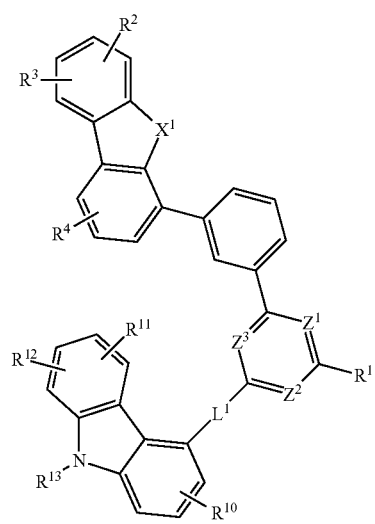
[Chemical Formula 1-4b-III]
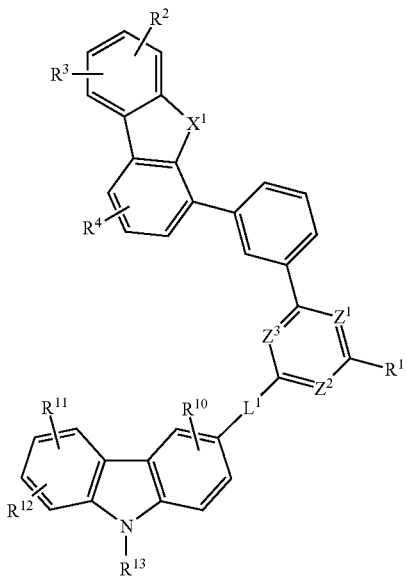
[Chemical Formula 1-4b-IV]
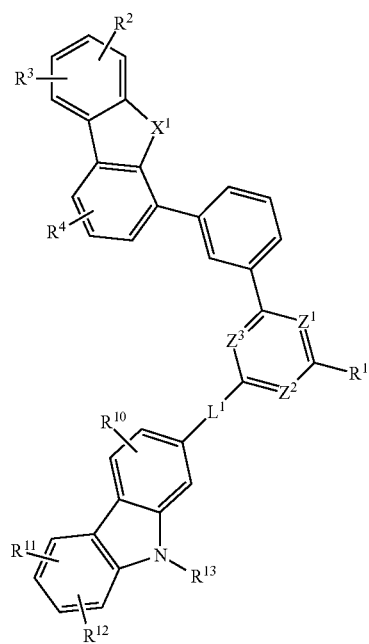

[Chemical Formula 1-4b-V]

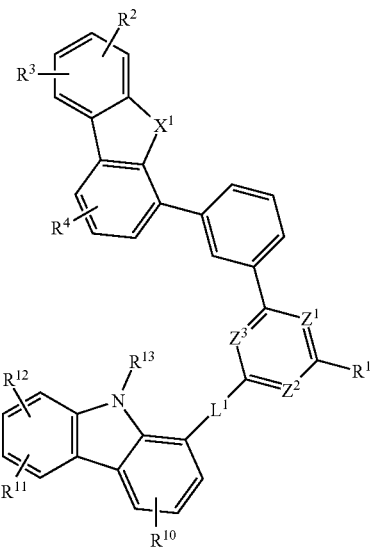

In Chemical Formula 1-3a-I to Chemical Formula 1-3a-V, Chemical Formula 1-4a-I to Chemical Formula 1-4a-V, and Chemical Formula 1-4b-I to Chemical Formula 1-4b-V, $X^1$, $Z^1$ to $Z^3$, $L^1$, $R^1$ to $R^4$ and $R^9$ to $R^{13}$ may be the same as described above.

In an implementation, the first host may be represented by one of Chemical Formula 1-3a-I, Chemical Formula 1-3a-II, Chemical Formula 1-3a-III, Chemical Formula 1-4a-I, Chemical Formula 1-4b-I and Chemical Formula 1-4b-II, and may be more preferably represented by one of Chemical Formula 1-3a-I, Chemical Formula 1-3a-II, and Chemical Formula 1-3a-III.

In an implementation, the hexagonal ring including $Z^1$ to $Z^3$ may be pyrimidine or triazine, e.g., pyrimidine where $Z^1$ and $Z^2$ are N, pyrimidine where $Z^1$ and $Z^3$ are N, pyrimidine where $Z^2$ and $Z^3$ are N, or triazine where $Z^1$ to $Z^3$ are N, and, e.g., triazine where $Z^1$ to $Z^3$ are N.

In an implementation. $R^1$ may be a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group, and more specifically $R^1$ may be a substituted or unsubstituted phenyl group, a substituted or unsubstituted dibenzofuranyl group, or a substituted or unsubstituted dibenzothiophenyl group. In an implementation, $R^1$ may be, e.g., a substituent of Group I.

[Group 1]

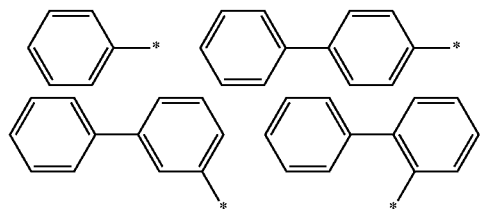

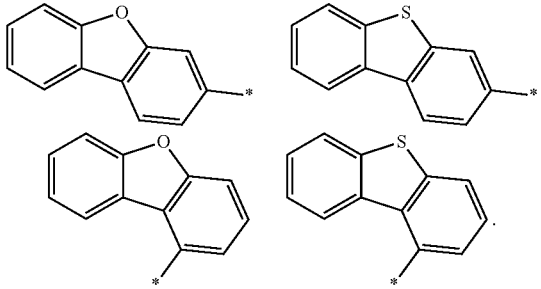

In Group I, * is a linking point with a nitrogen-containing hexagonal ring.

$R^1$ may be, e.g., a phenyl group, a dibenzofuranyl group, or a dibenzothiophenyl group.

In an implementation, $R^1$ and $R^2$ to $R^4$ may each independently be hydrogen, deuterium, a cyano group, or a substituted or unsubstituted C6 to C12 aryl group. In an implementation, $R^a$ and $R^2$ to $R^4$ may each independently be hydrogen, deuterium, or a cyano group, e.g., $R^a$ and $R^2$ to $R^4$ may be all hydrogen.

In an implementation, $L^1$ and $L^2$ may each independently be a single bond, or a substituted or unsubstituted C6 to C12 arylene group. In an implementation, $L^1$ and $L^2$ may each independently be a single bond, a meta-phenylene group, or a para-phenylene group.

In an implementation, $R^9$ to $R^{11}$ may each independently be hydrogen, deuterium, a cyano group, or a substituted or unsubstituted C6 to C12 aryl group. In an implementation, $R^9$ to $R^{11}$ may each independently be hydrogen, deuterium, a cyano group or a phenyl group. In an implementation, $R^9$ to $R^{11}$ may be all hydrogen or at least one of $R^9$ to $R^{11}$ may be a phenyl group. In an implementation, $R^9$ to $R^{11}$ may be all hydrogen or one of $R^9$ to $R^{11}$ may be a phenyl group.

In an implementation, the first host may be, e.g., selected from compounds of Group 1.

[Group 1]

[B-1]

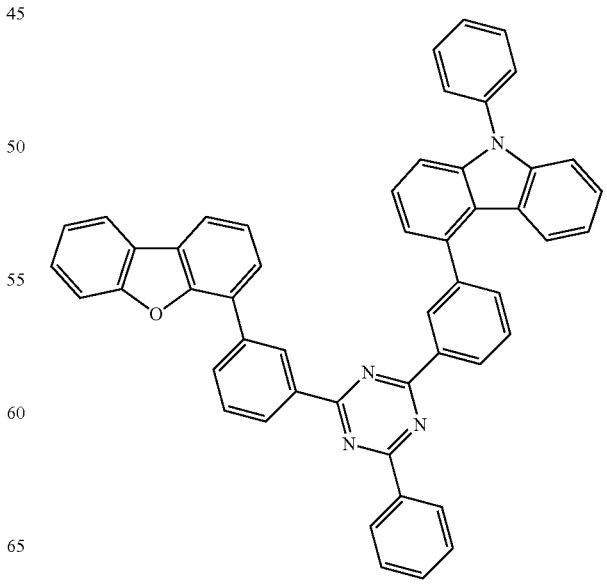

[B-2]
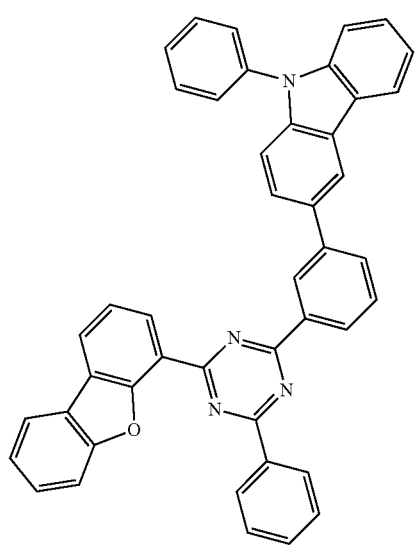
[B-3]
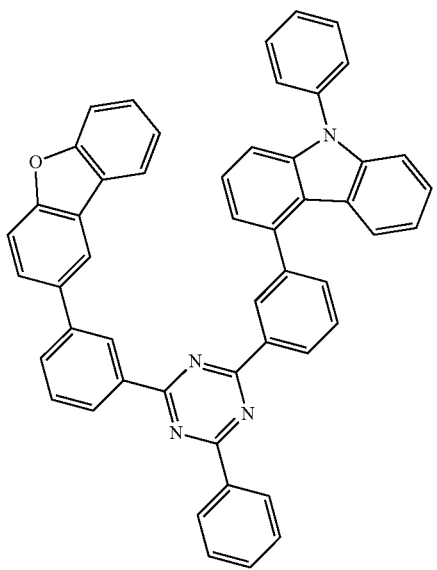
[B-4]
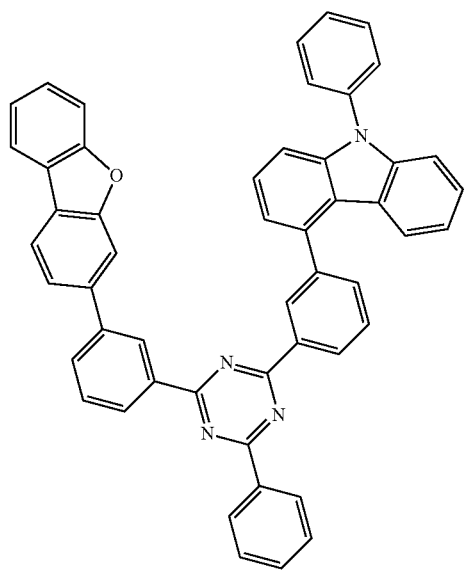
[B-5]
[B-6]
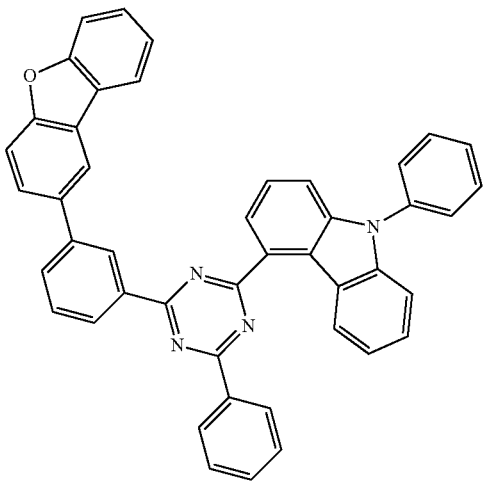

[B-7]
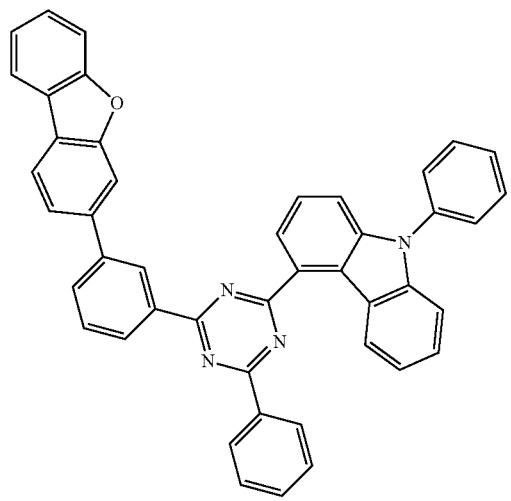
[B-8]
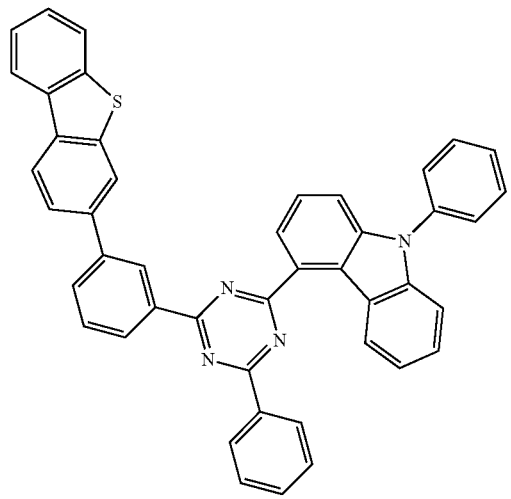
[B-9]
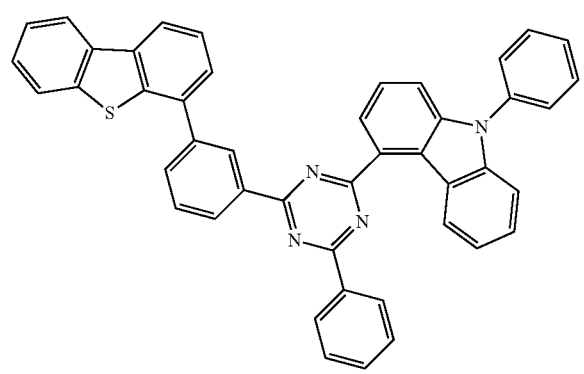
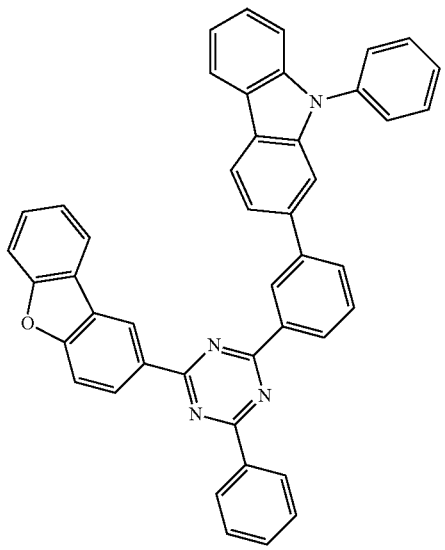
[B-11]
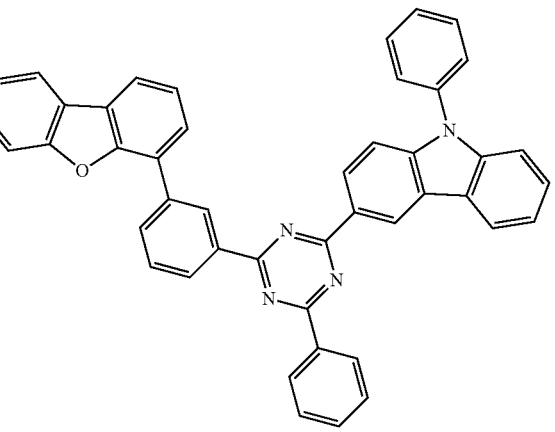
[B-12]

[B-13]
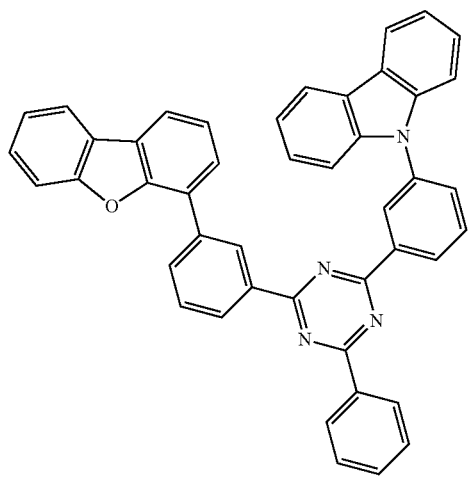
[B-14]
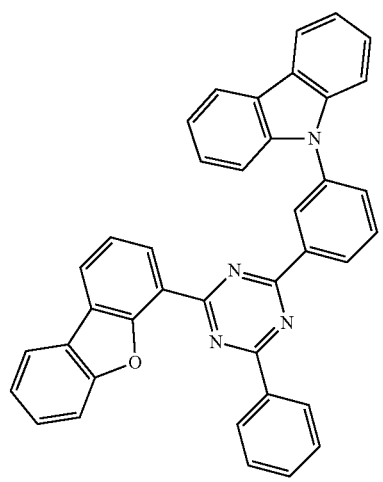
[B-15]
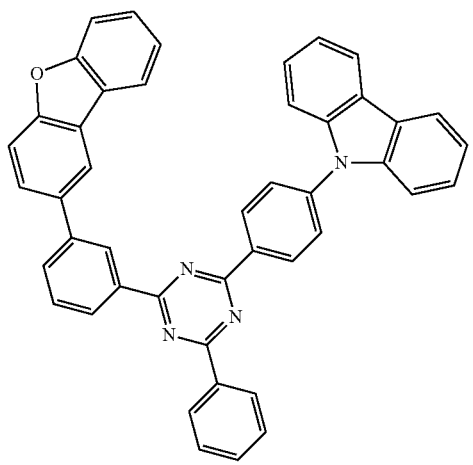
[B-16]
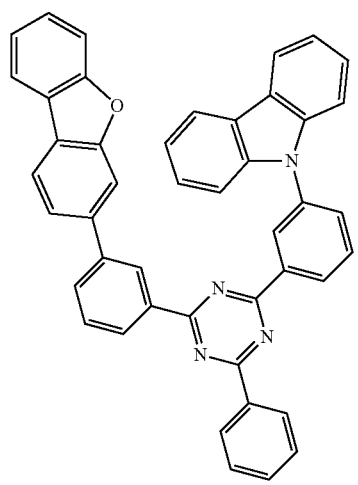
[B-17]
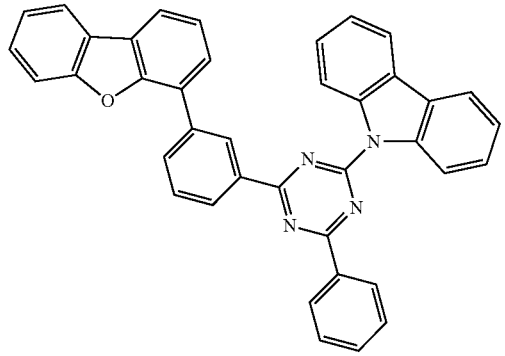
[B-18]

[B-19]
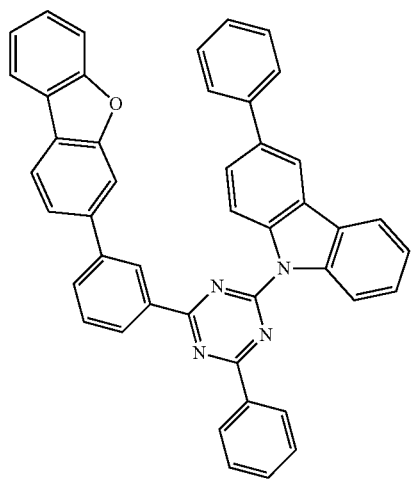
[B-22]
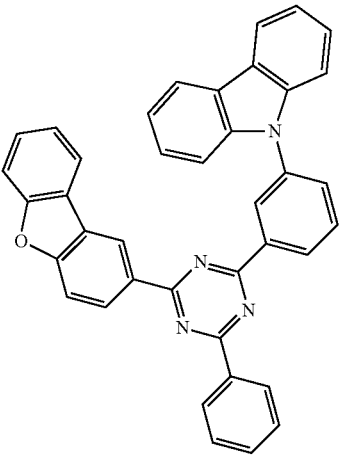
[B-20]
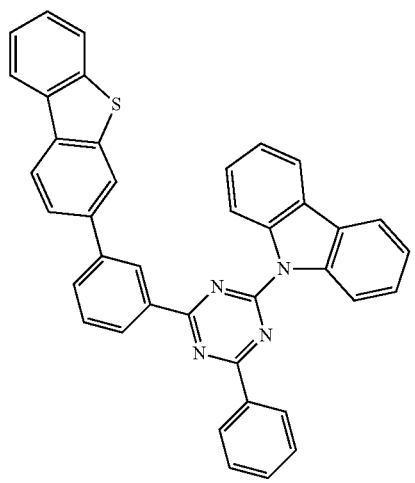
[B-23]
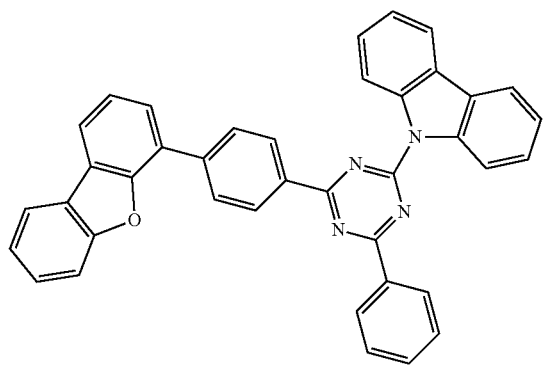
[B-21]
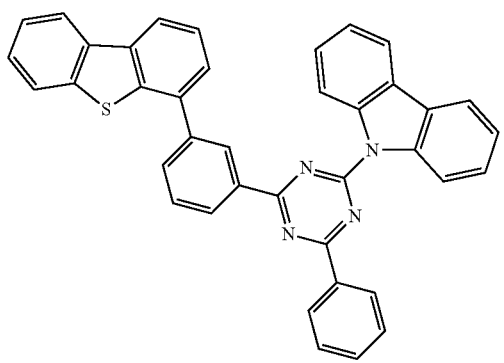
[B-24]
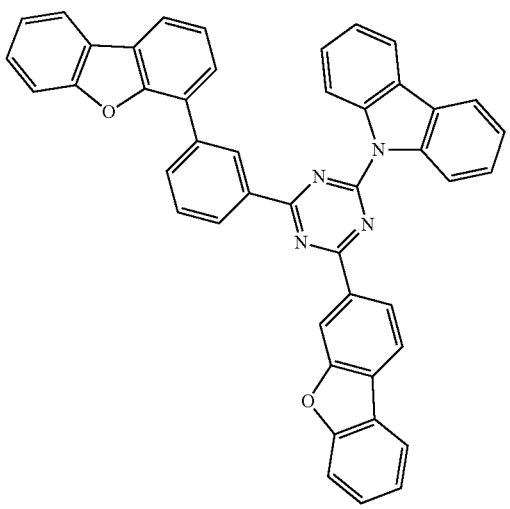

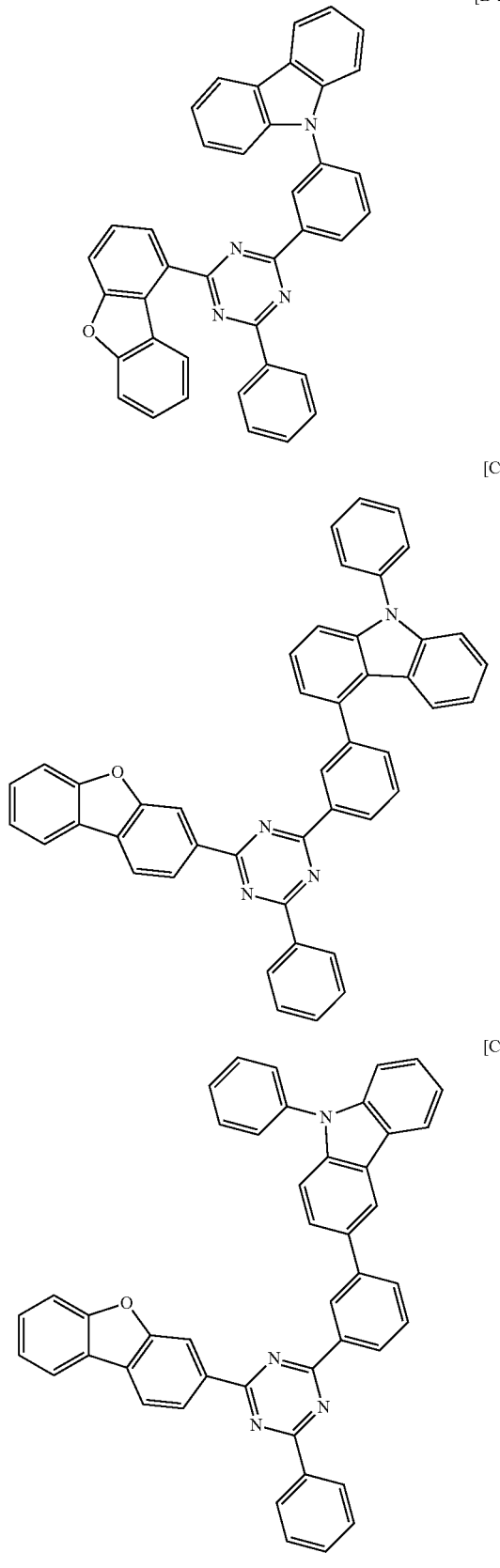
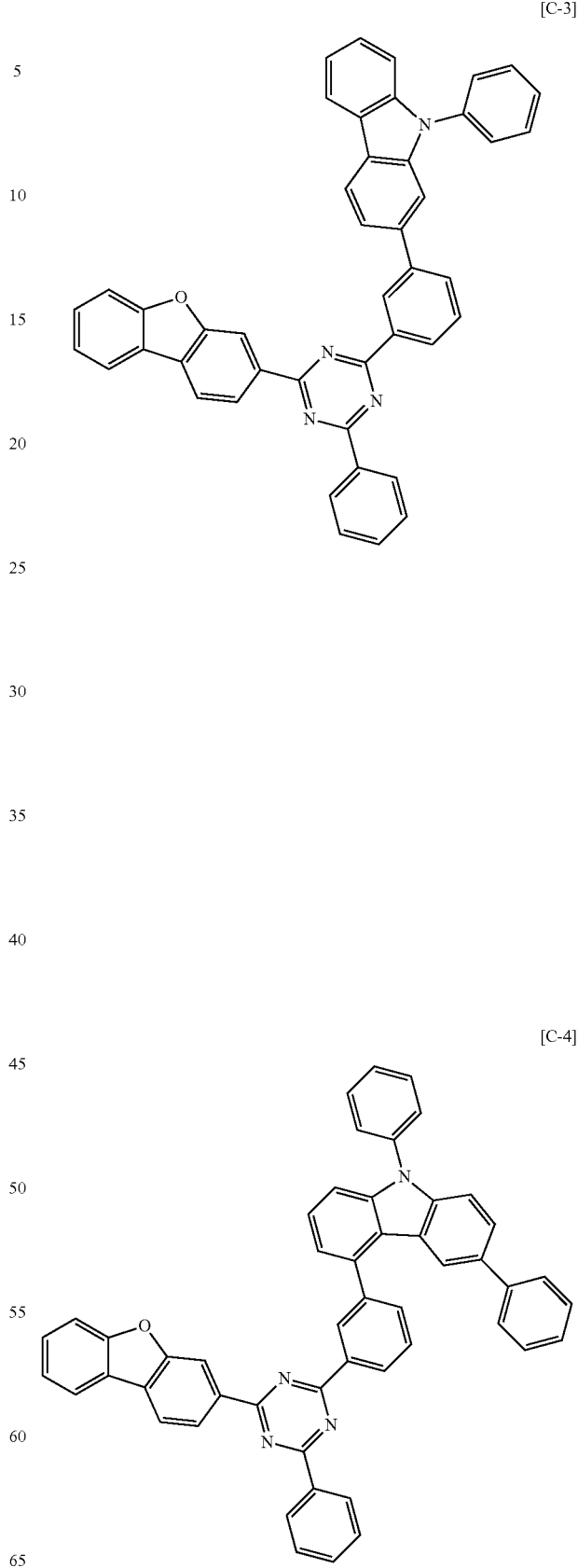

[C-5]
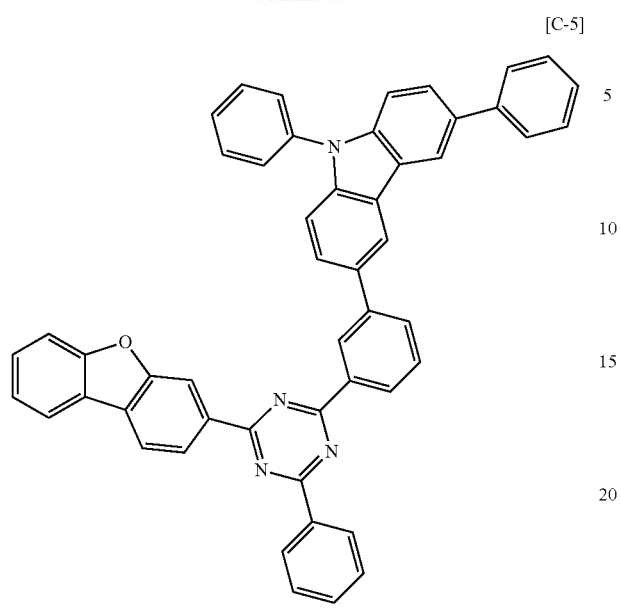
[C-6]
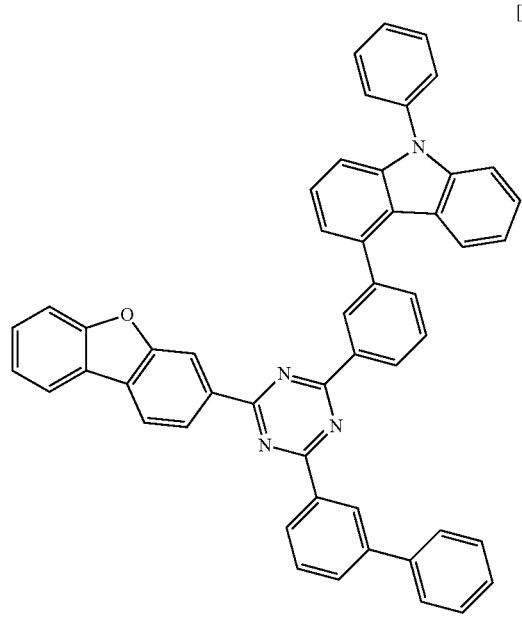
[C-7]
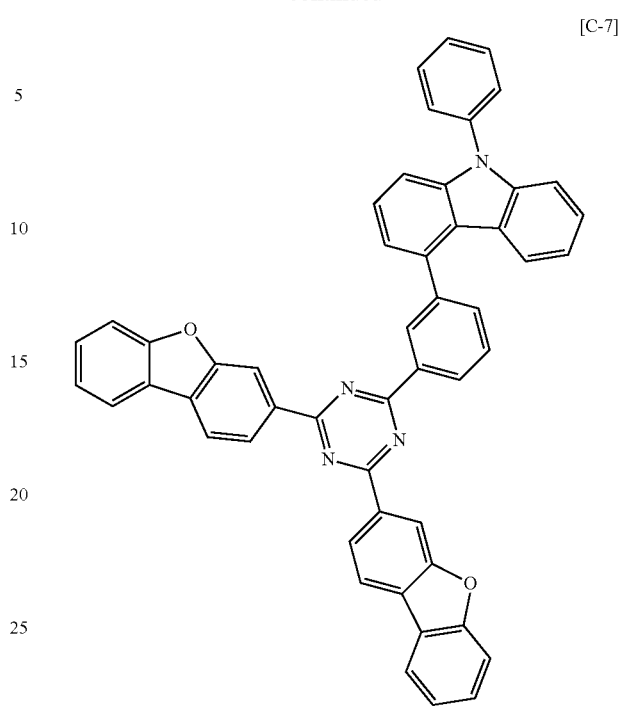
[C-8]
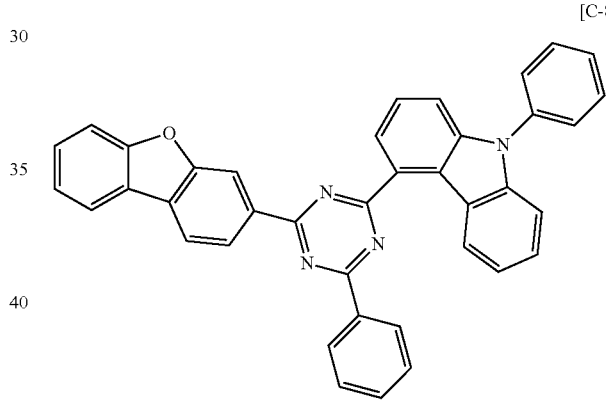
[C-9]
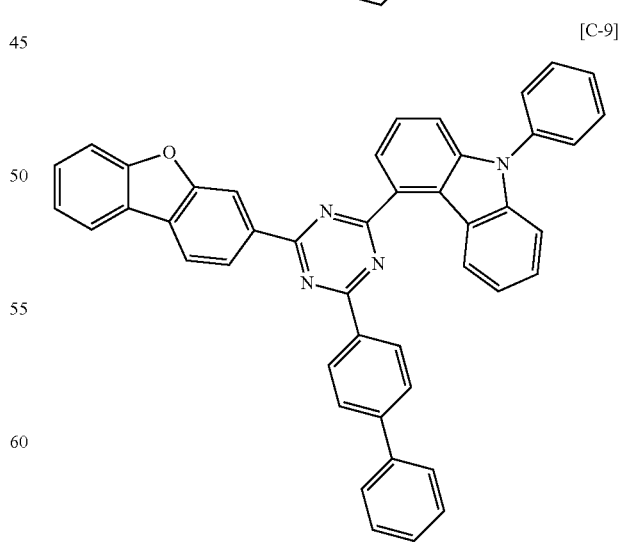

[C-10]
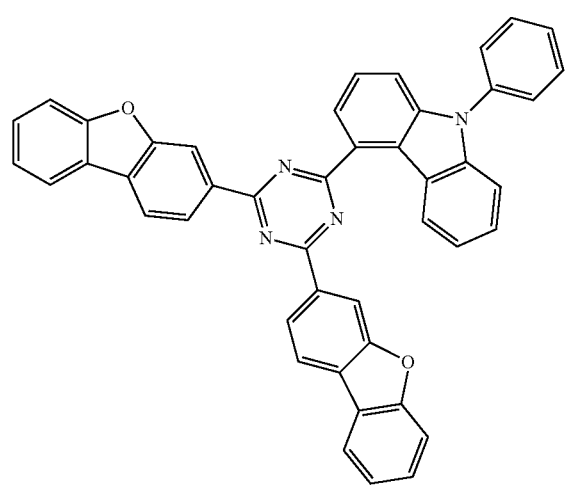
[C-13]
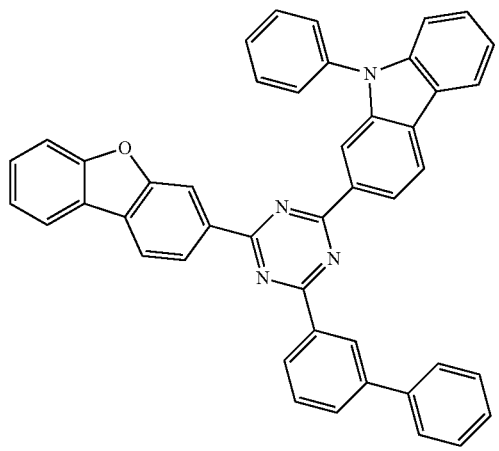
[C-11]
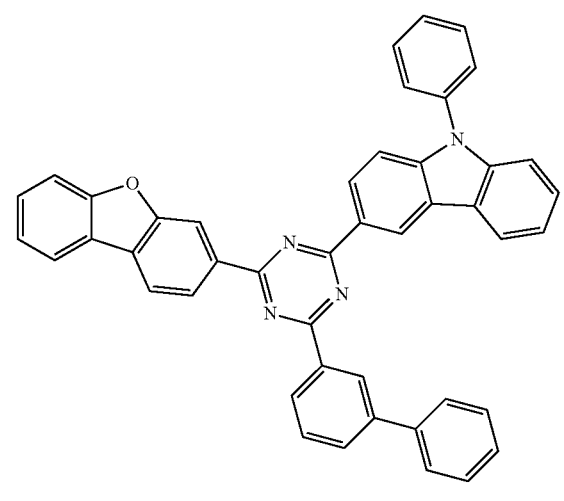
[C-14]
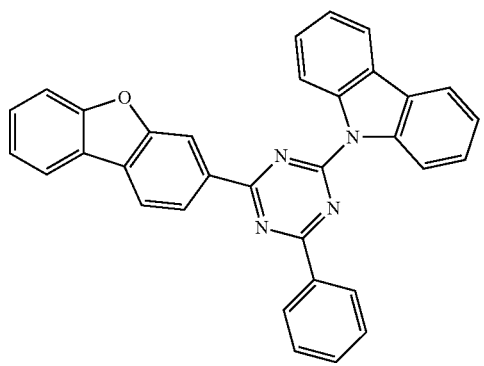
[C-12]
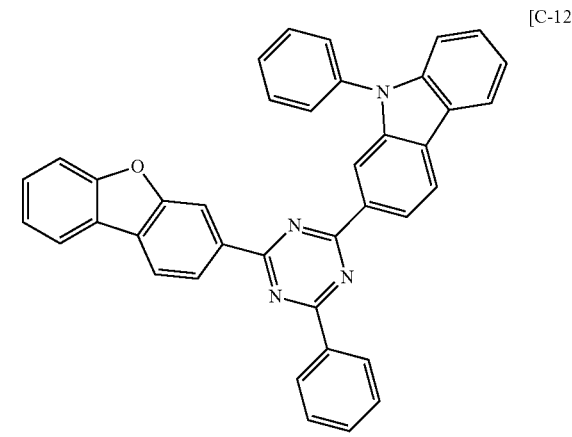
[C-15]
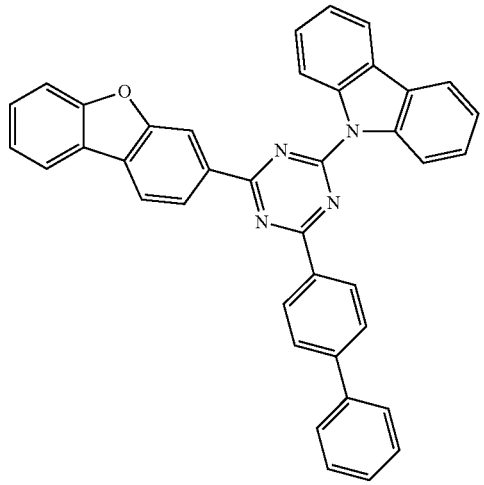

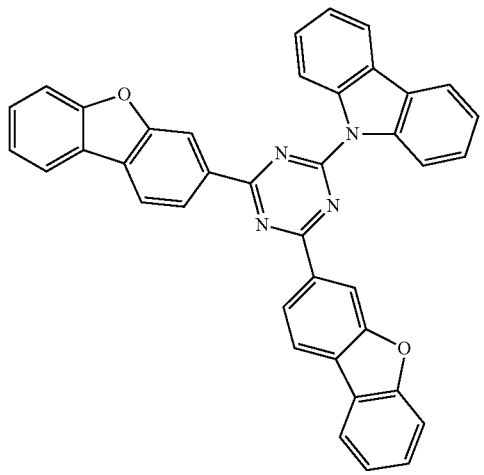
[C-16]
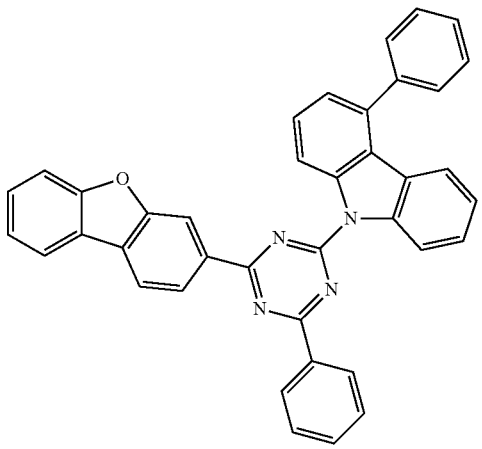
[C-19]
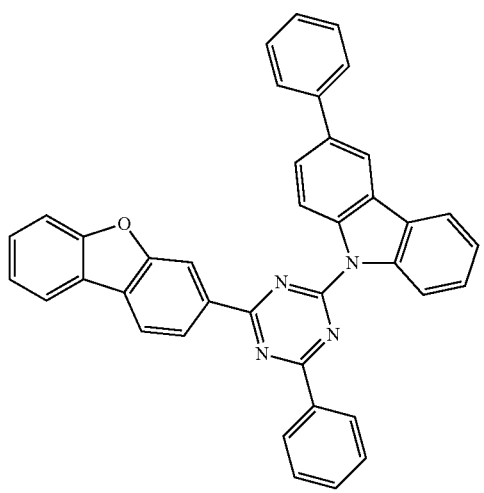
[C-17]
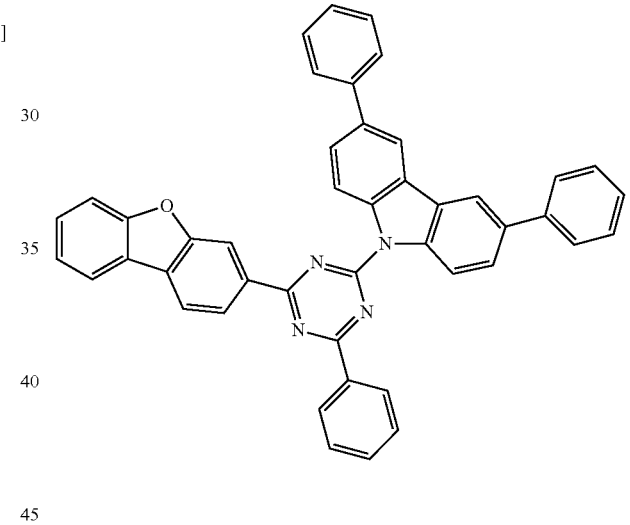
[C-20]
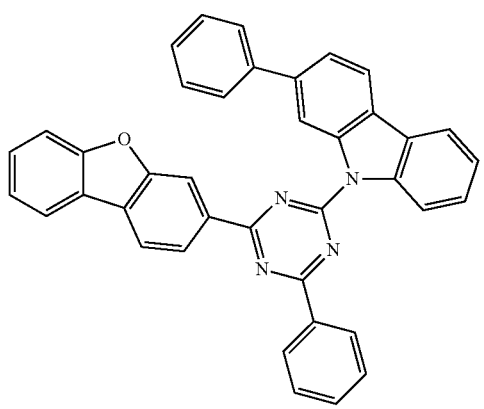
[C-18]
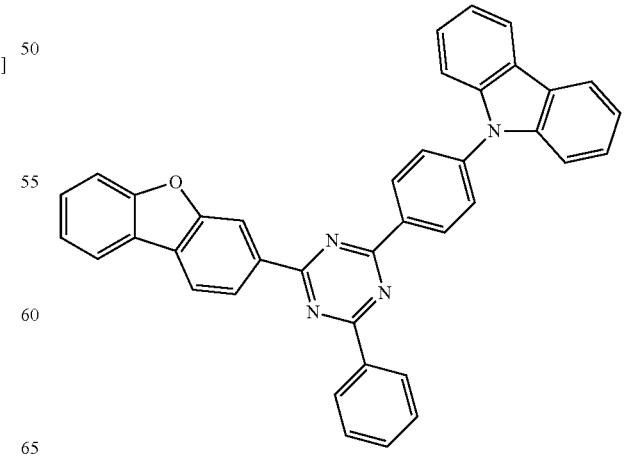
[C-21]

-continued
[C-22]
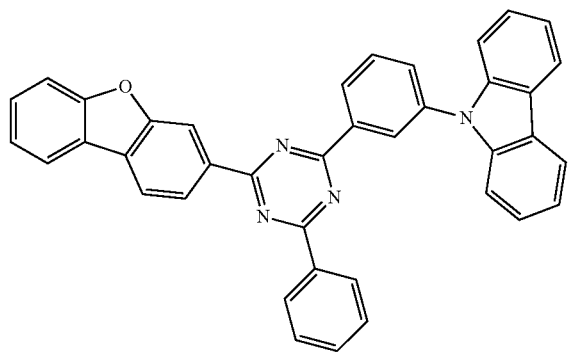
[C-23]
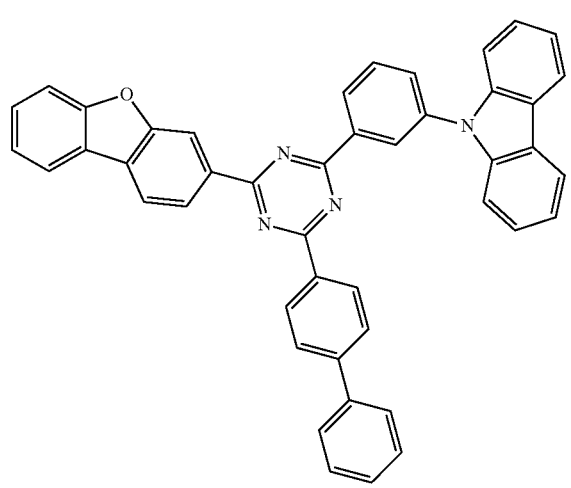
[C-24]
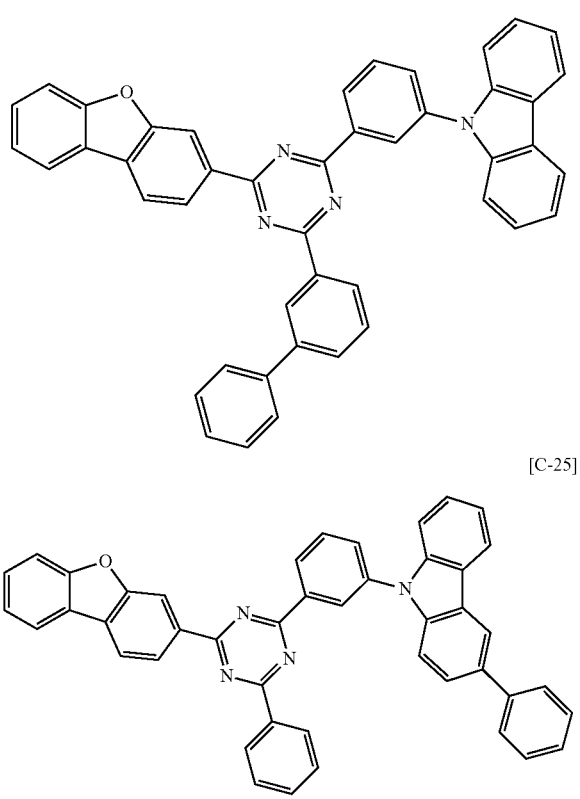
[C-25]
-continued
[C-26]
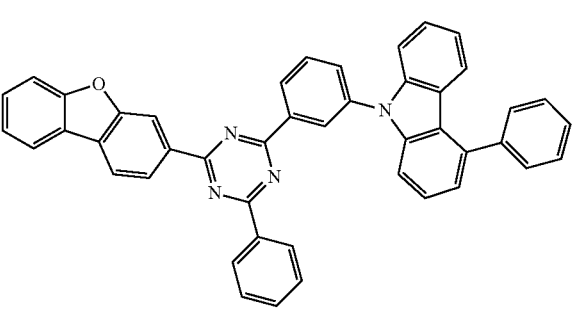
[C-27]
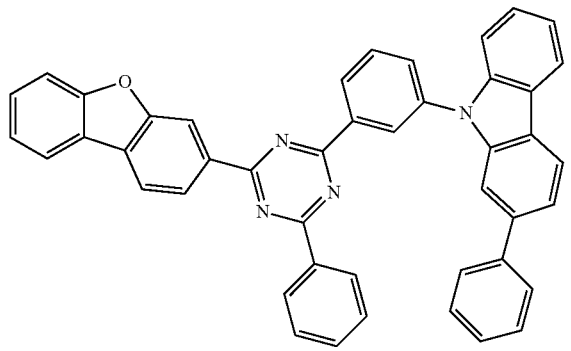
[C-28]
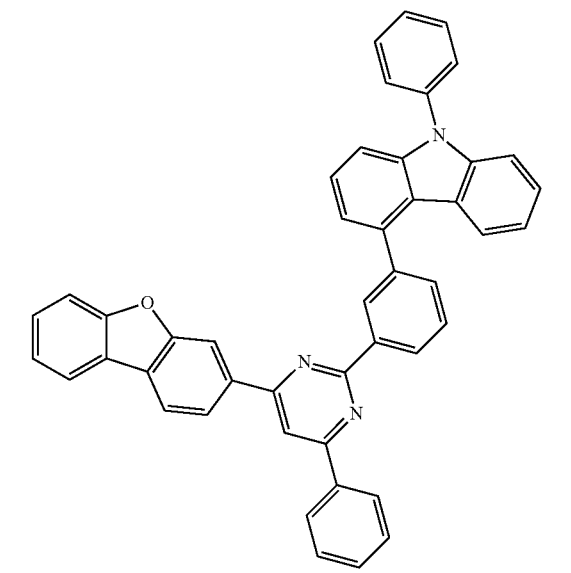

[C-29]
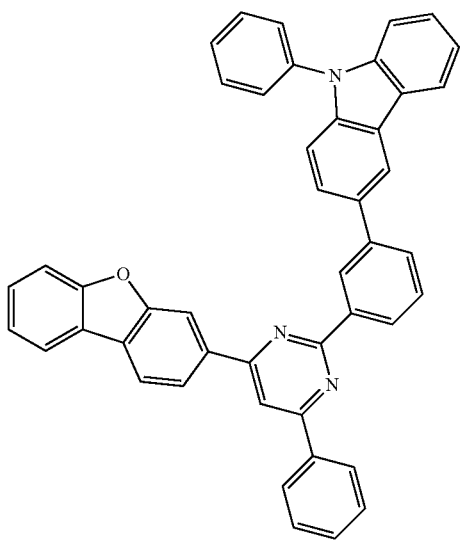
[C-31]
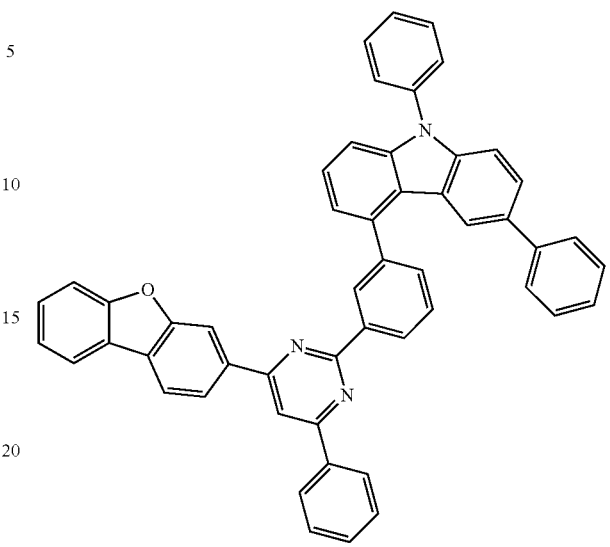
[C-30]
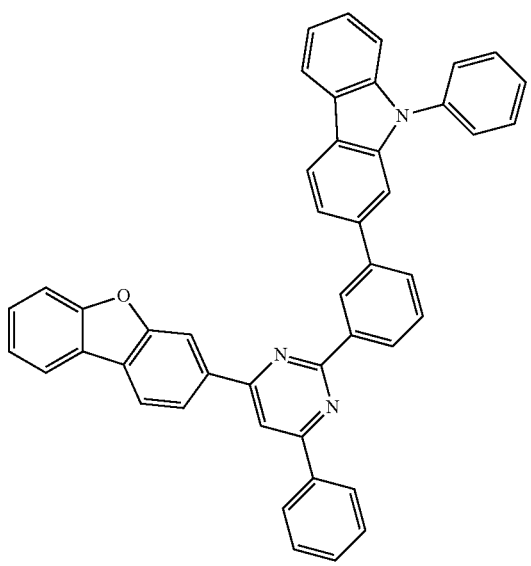
[C-32]
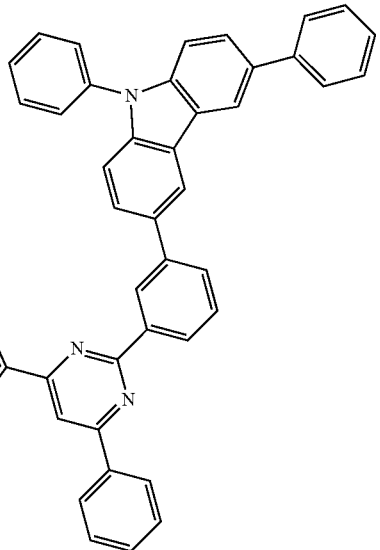

[C-33]
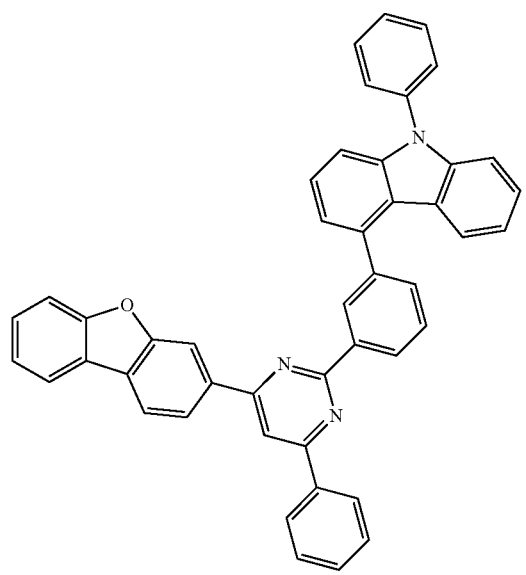
[C-34]
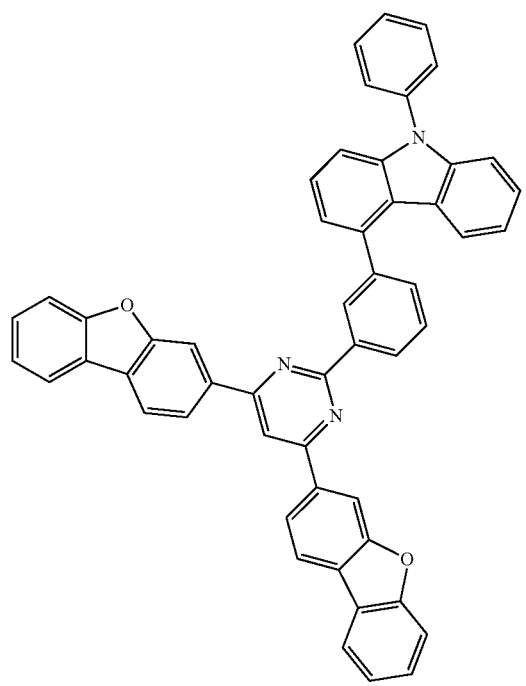
[C-35]
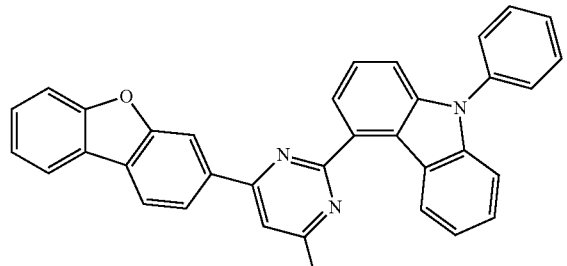
[C-36]
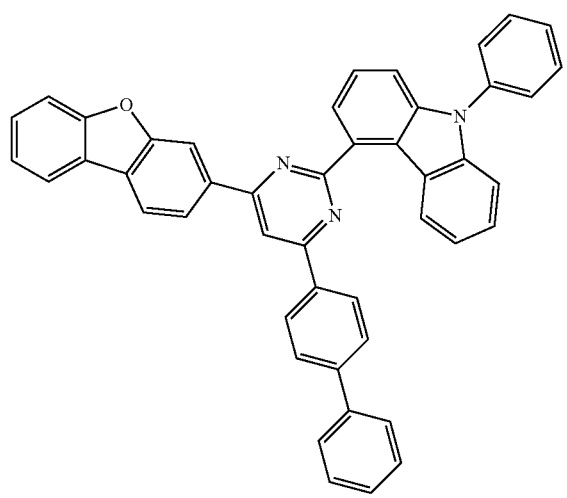
[C-37]
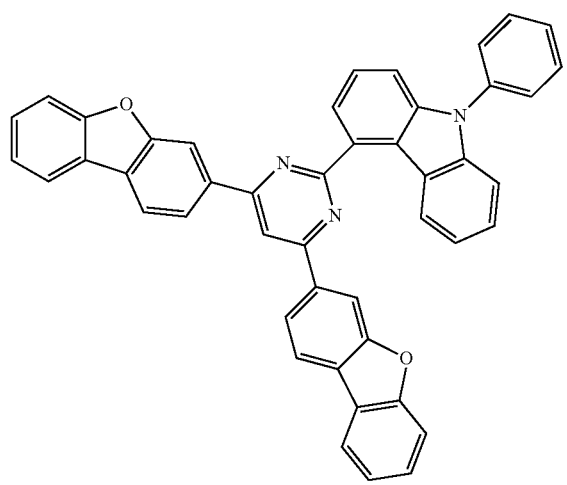

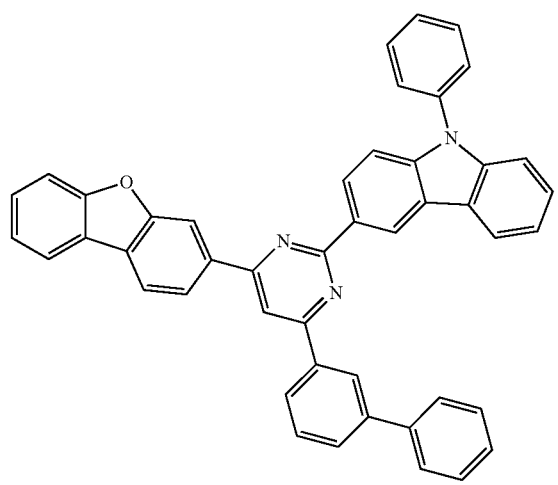
[C-38]
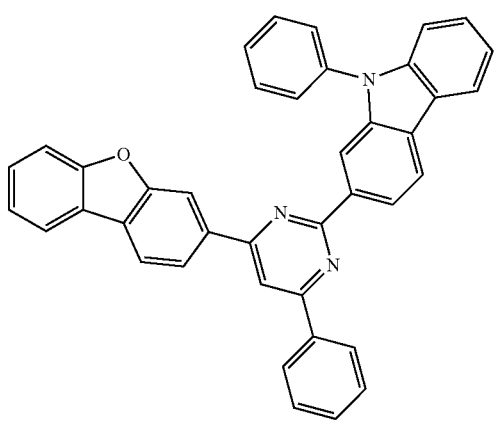
[C-39]
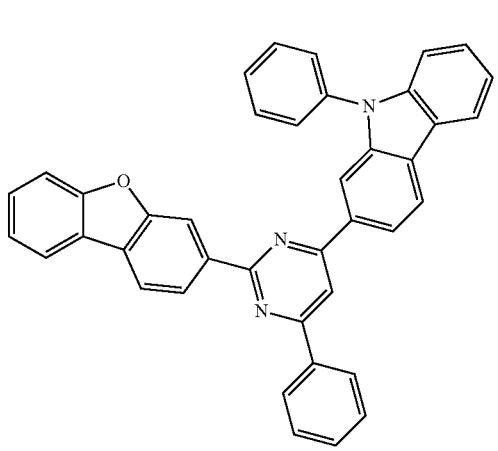
[C-40]
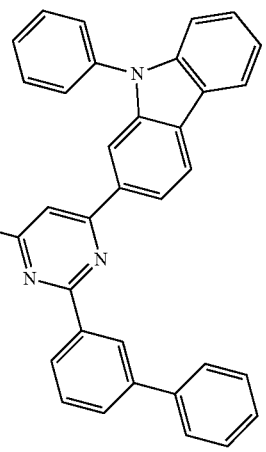
[C-41]
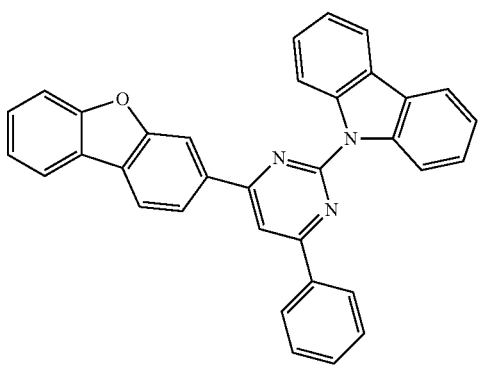
[C-42]
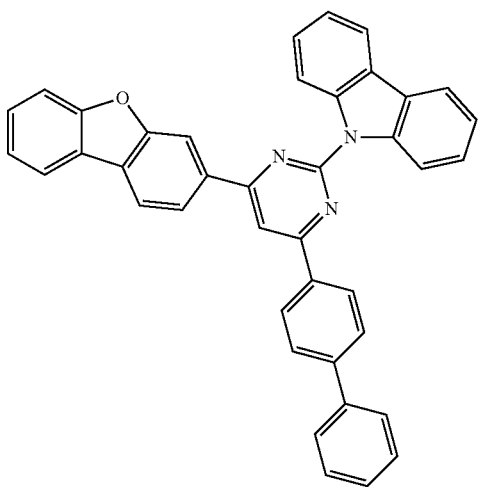
[C-43]

[C-44]
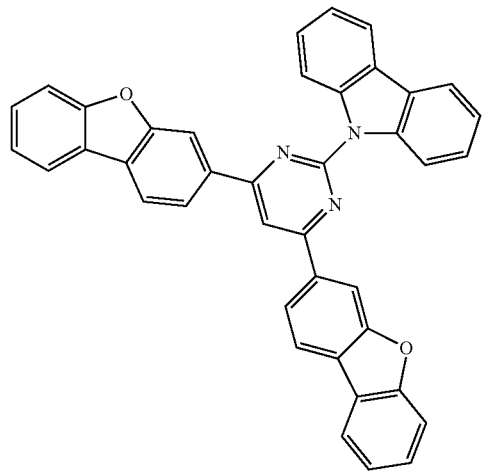
[C-45]
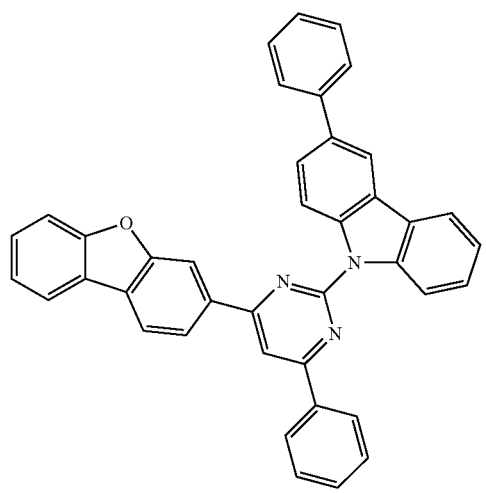
[C-46]
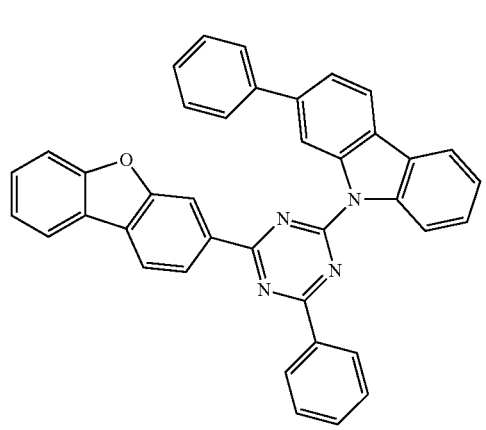
[C-47]
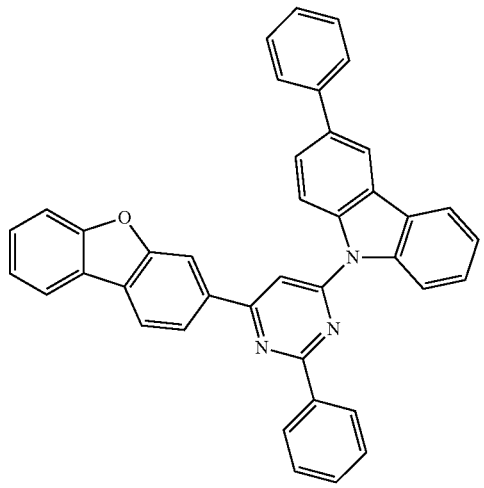
[C-48]
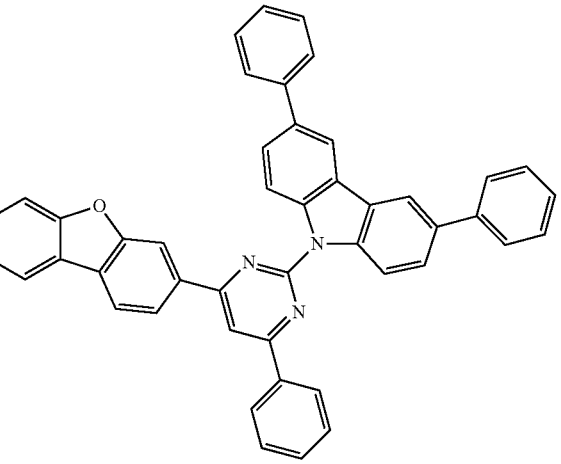
[C-49]
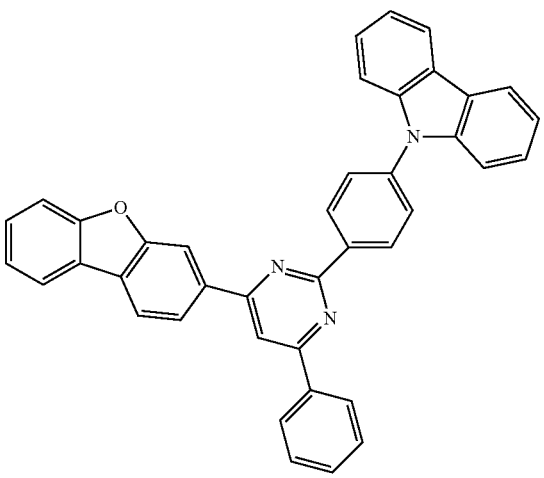

-continued
[C-50]
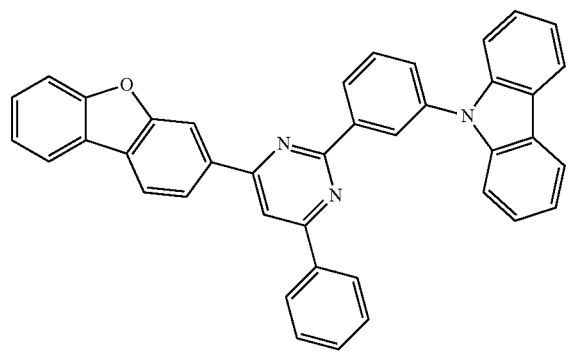
[C-51]
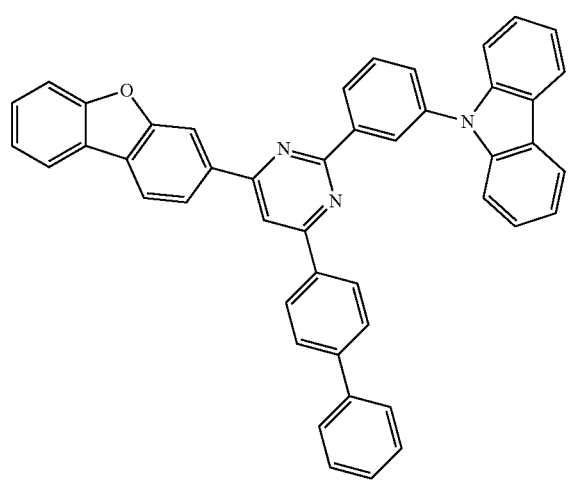
[C-52]
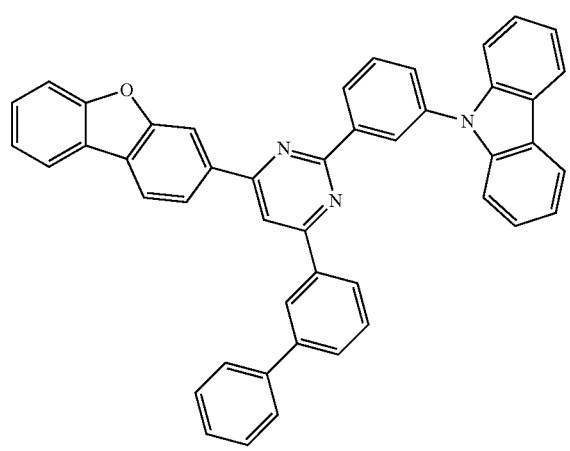
[C-53]
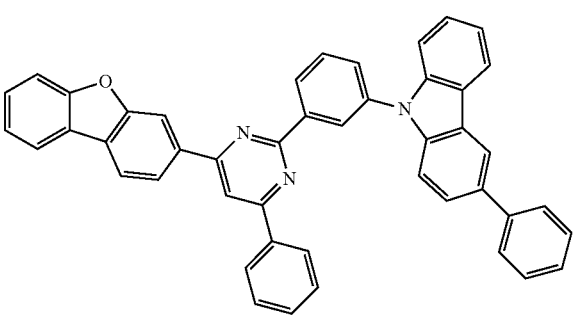
-continued
[C-54]
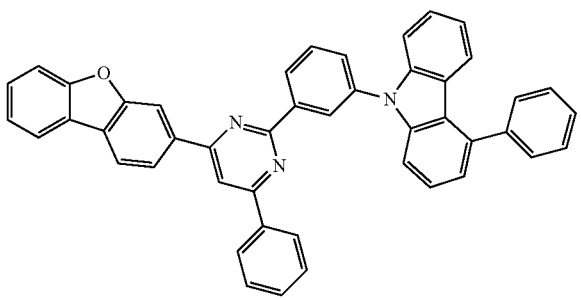
[C-55]
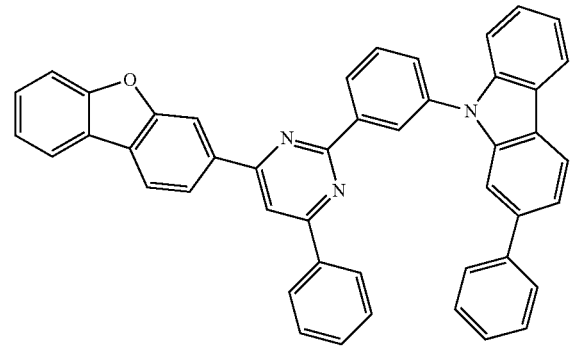
[C-56]
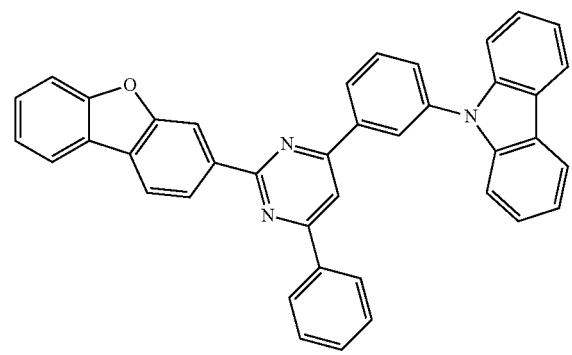
[C-57]
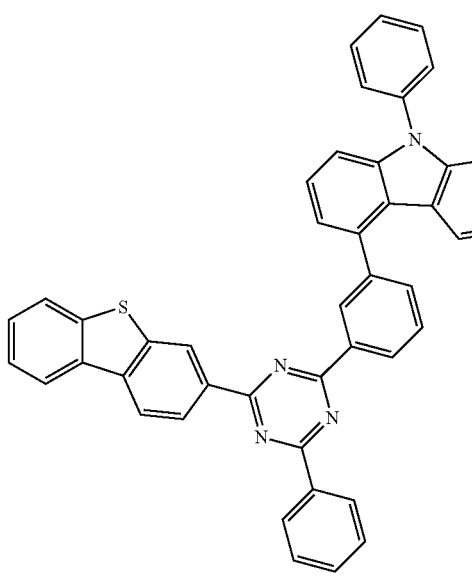

[C-58]
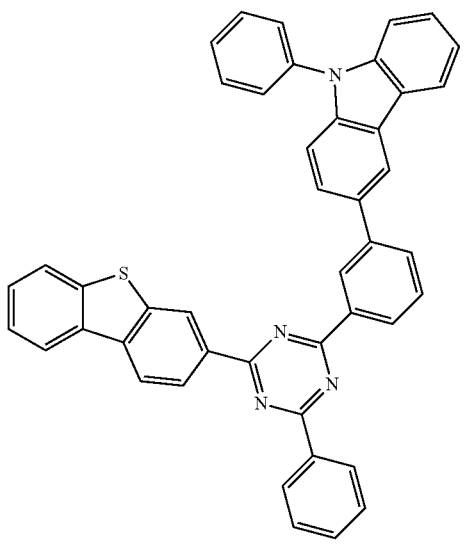
[C-60]
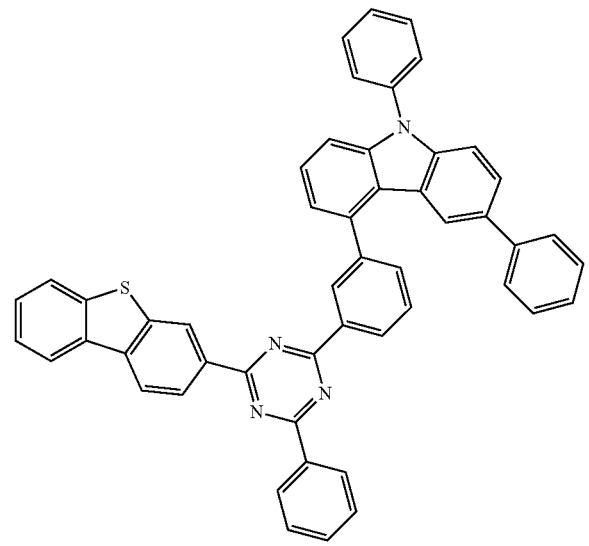
[C-59]
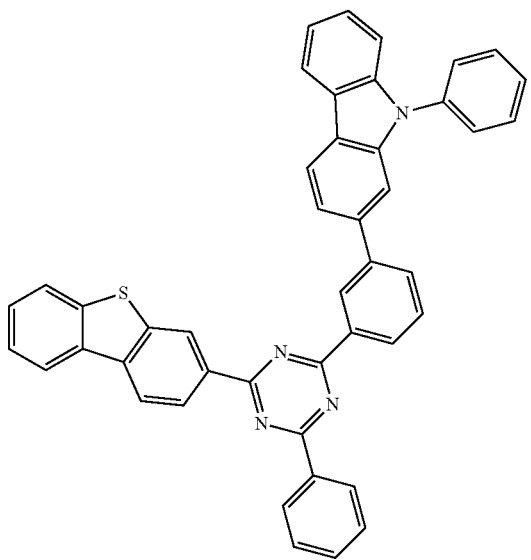
[C-61]
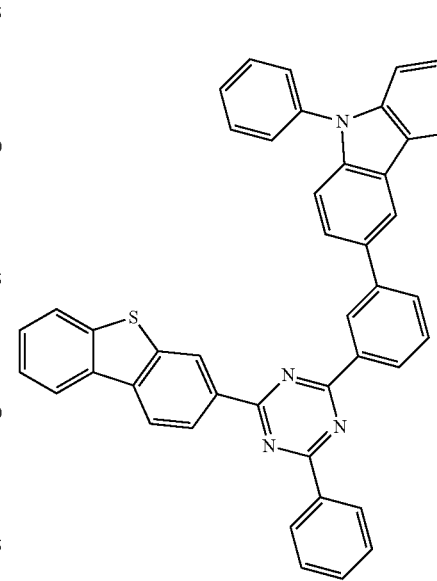

[C-62]
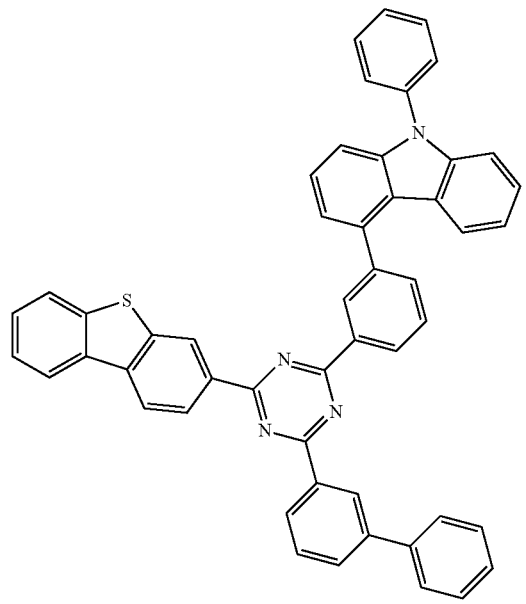
[C-63]
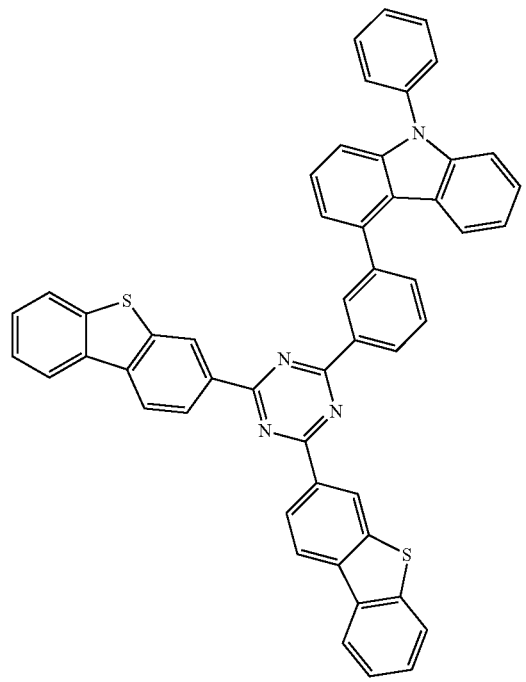
[C-64]
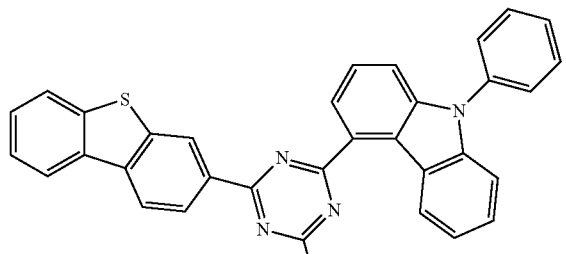
[C-65]
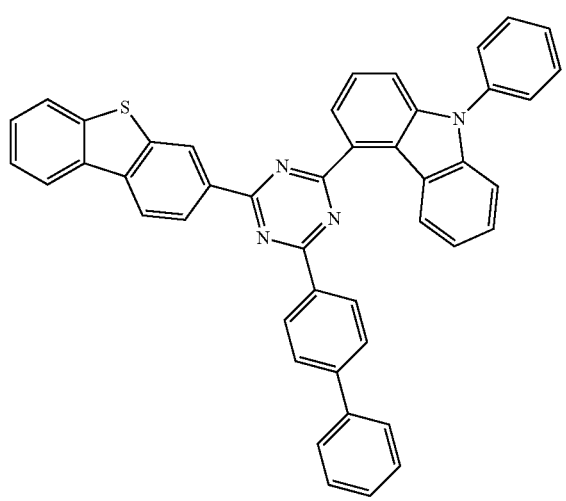
[C-66]
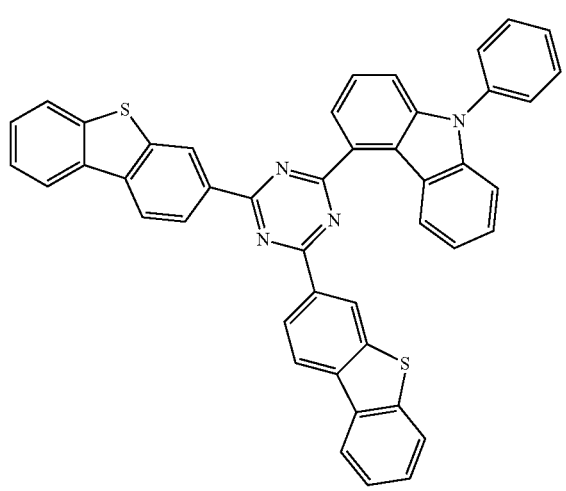

[C-66]
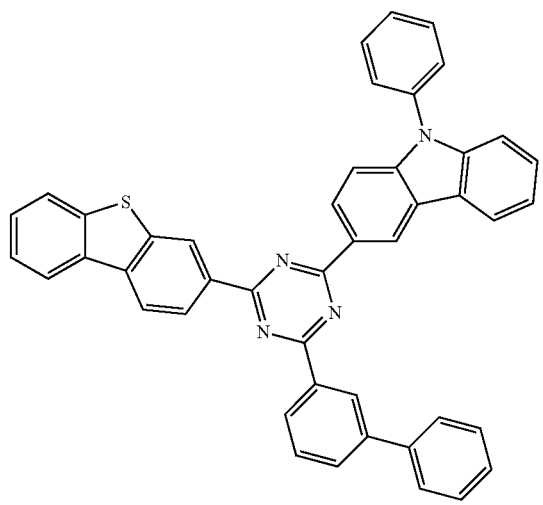
[C-67]
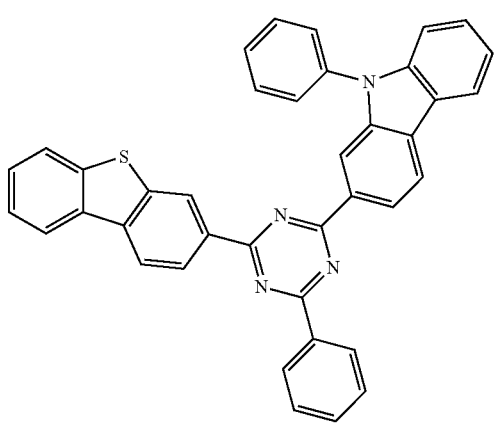
[C-68]
[C-69]
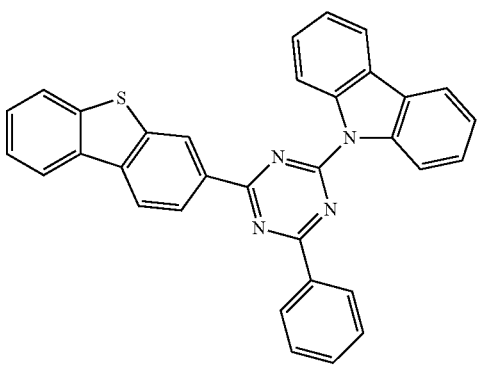
[C-70]
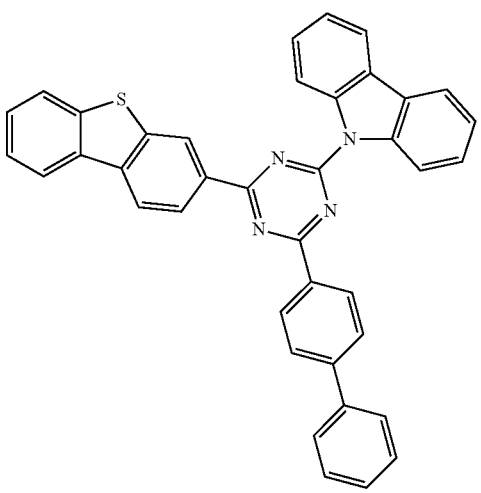
[C-71]
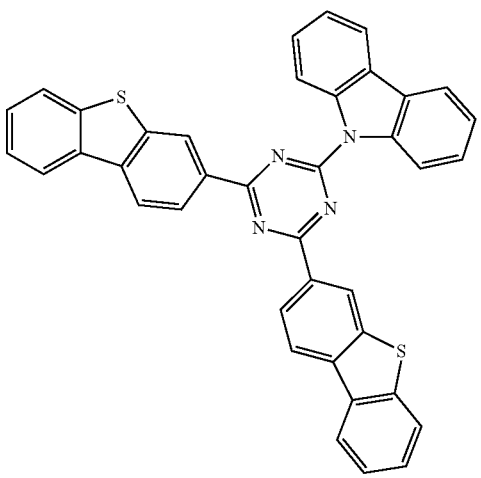

[C-72]
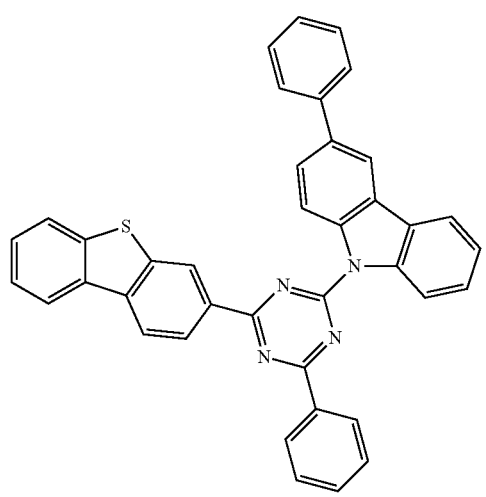
[C-73]
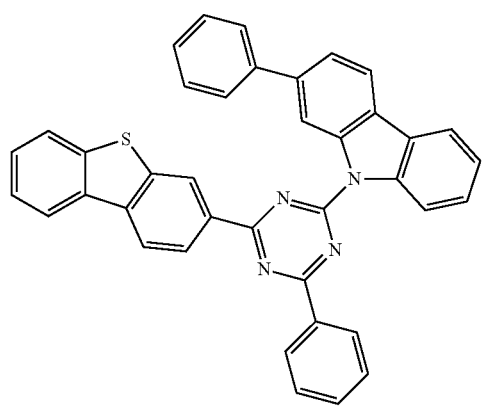
[C-74]
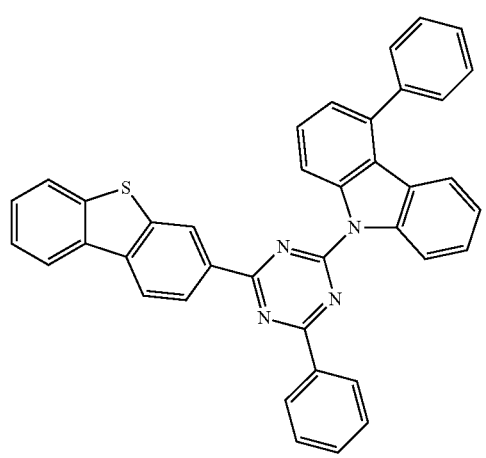
[C-75]
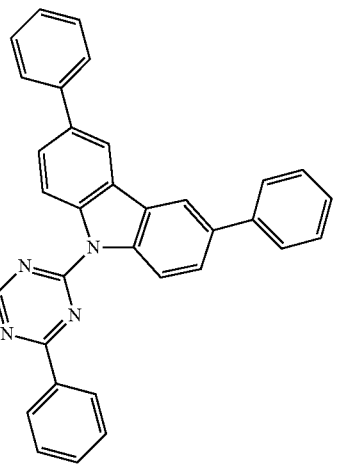
[C-76]
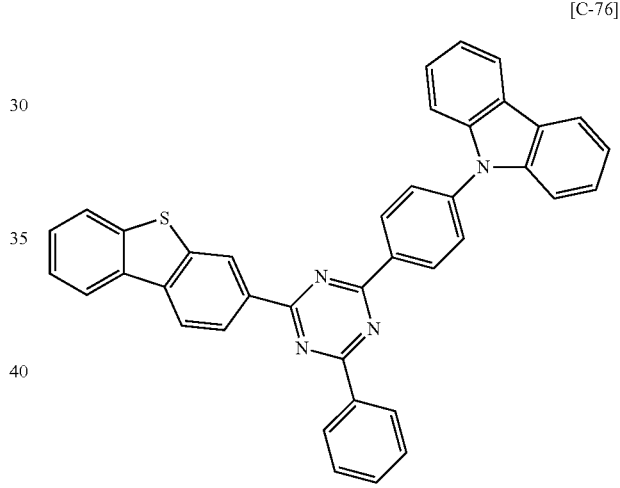
[C-77]

[C-78]
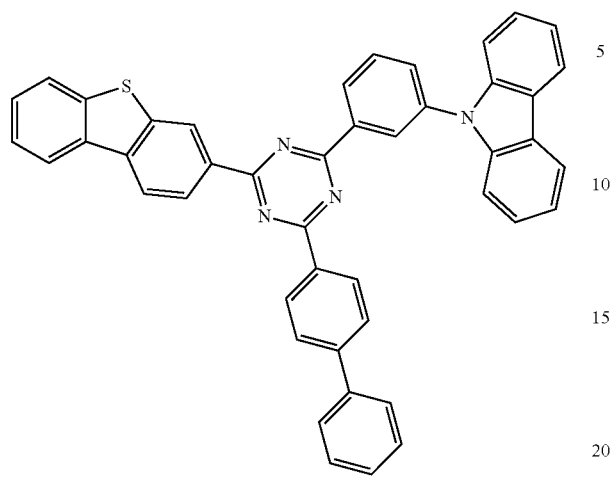
[C-82]
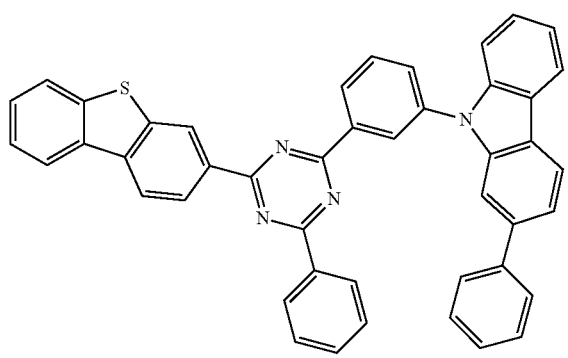
[C-79]
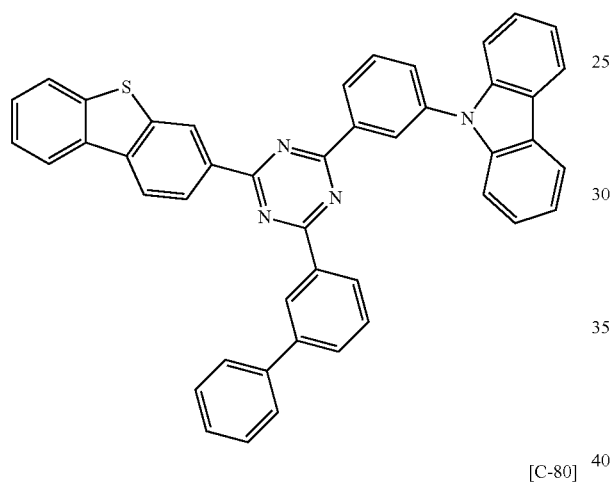
[C-83]
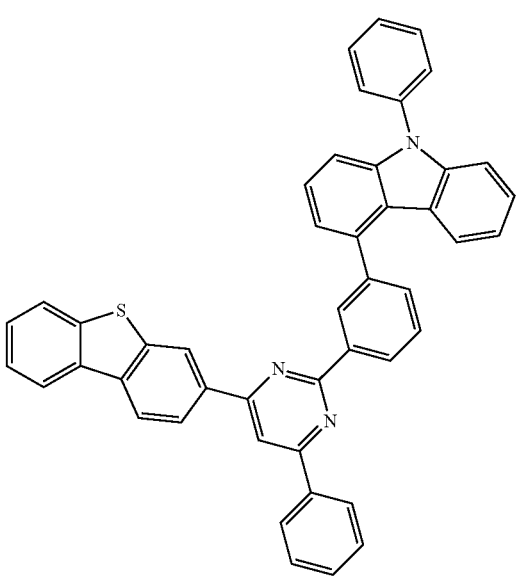
[C-80]
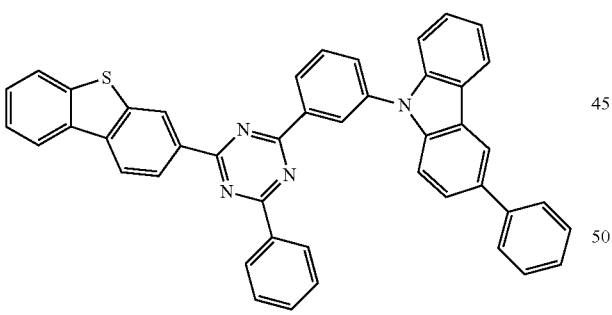
[C-84]
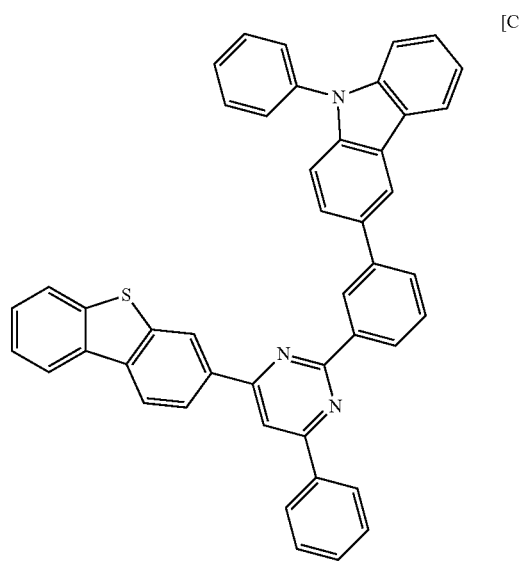
[C-81]

[C-85]
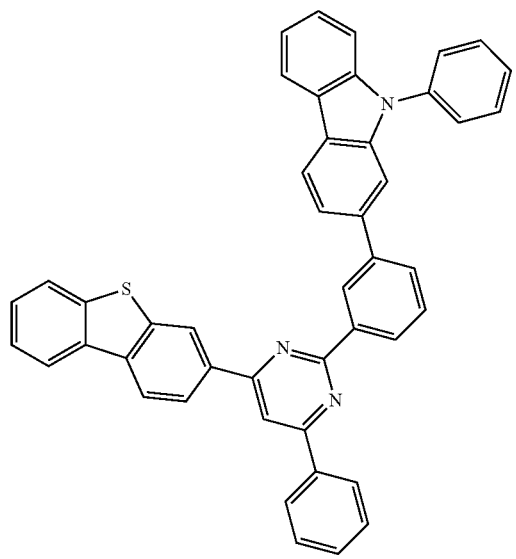
[C-86]
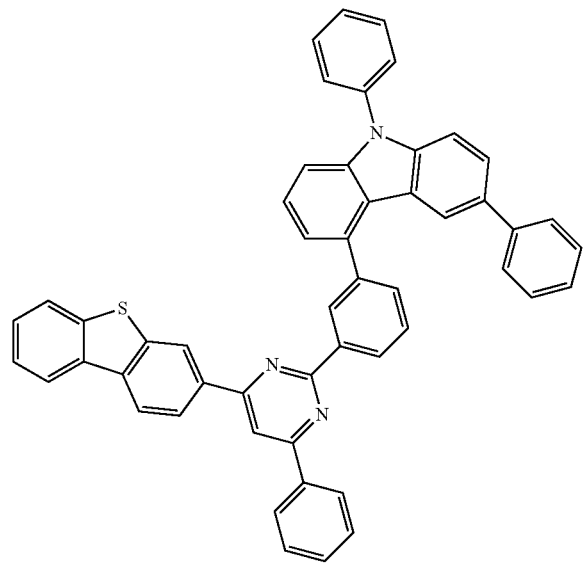
[C-87]
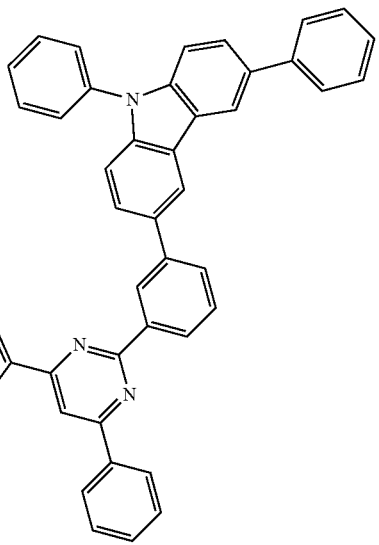
[C-88]
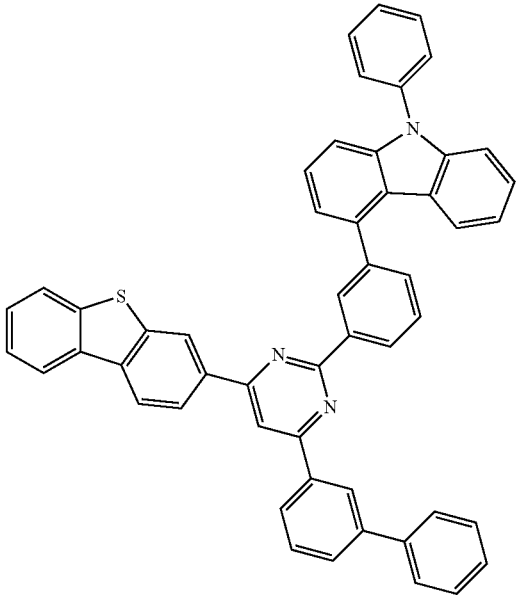

[C-89]
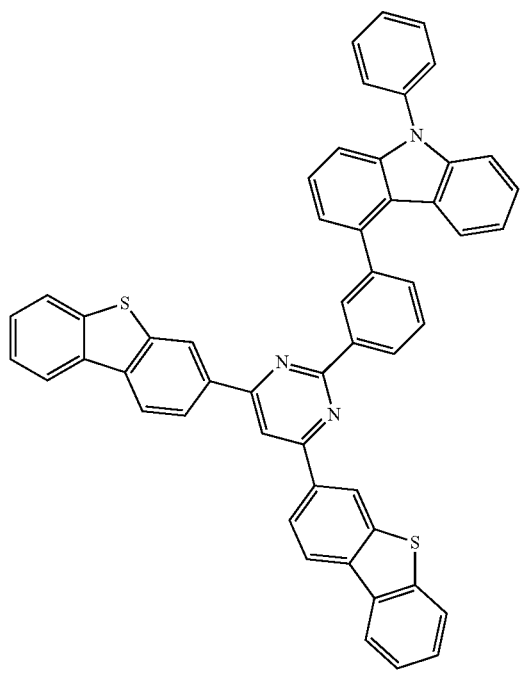
[C-90]
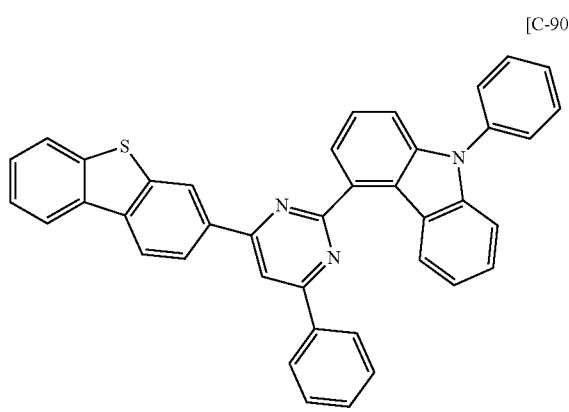
[C-91]
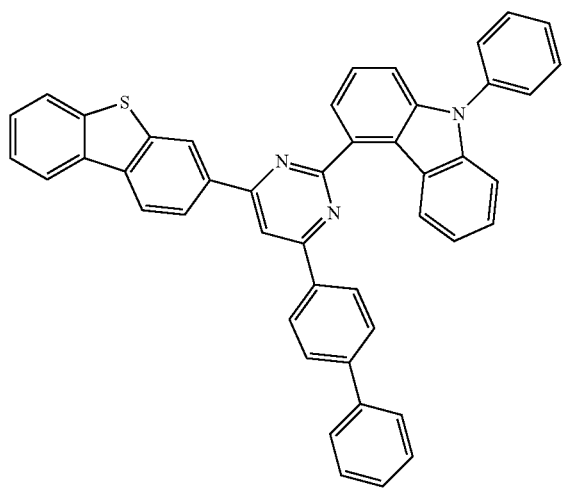
[C-92]
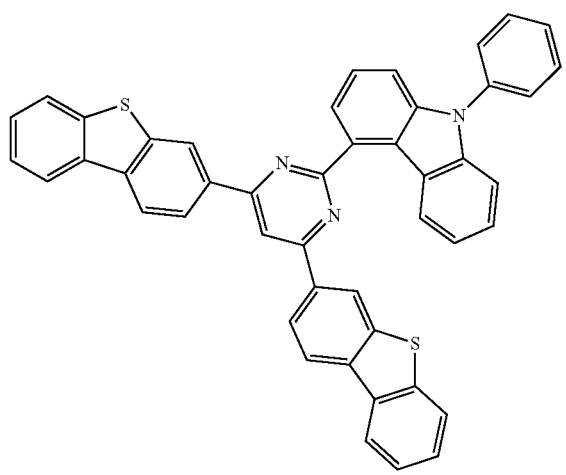
[C-93]
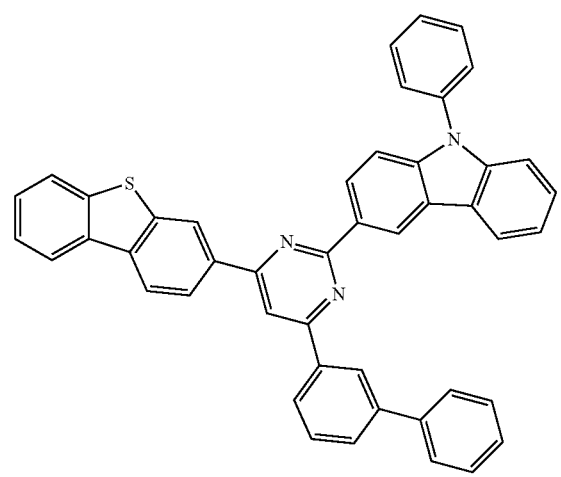
[C-94]
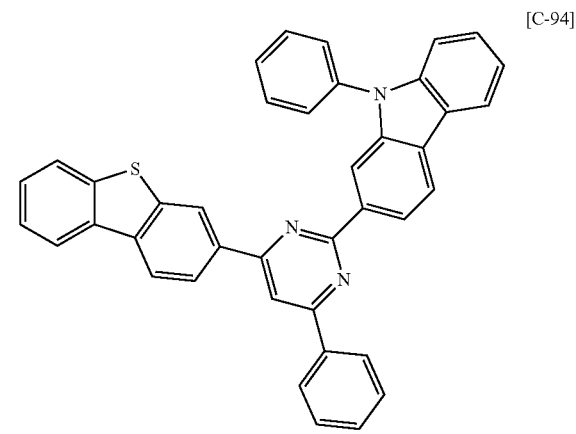

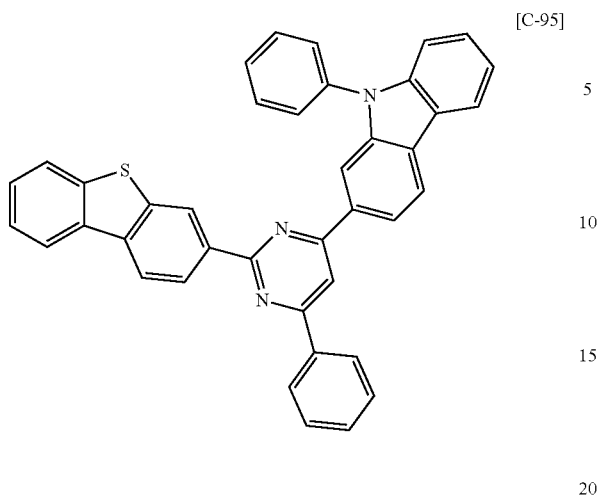 [C-95]
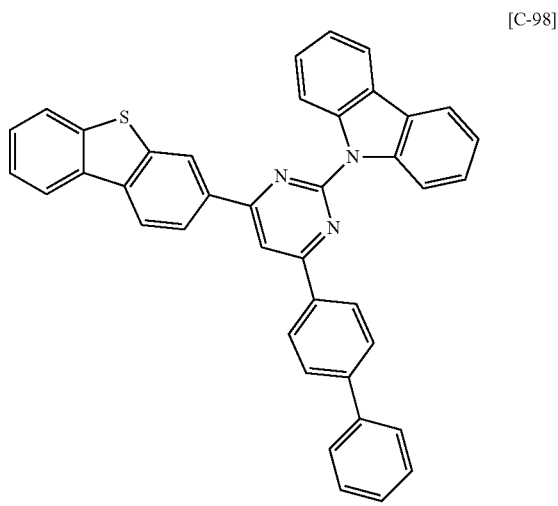 [C-98]
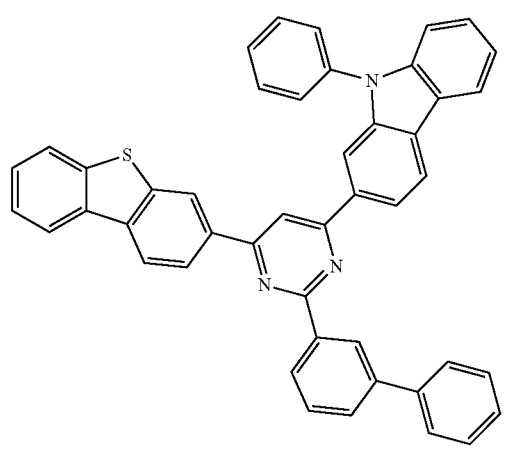 [C-96]
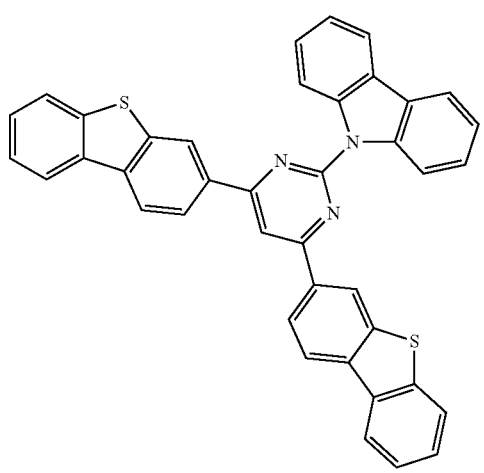 [C-99]
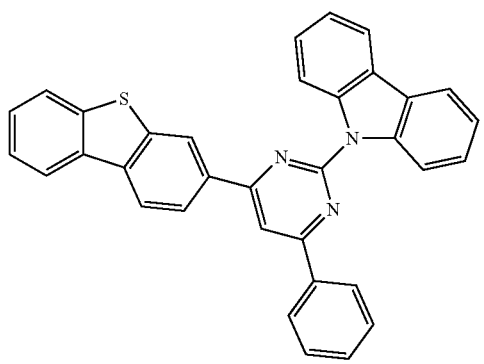 [C-97]
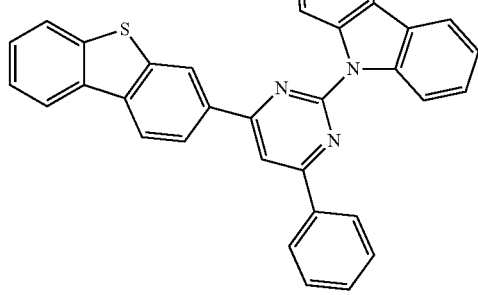 [C-100]

[C-101]
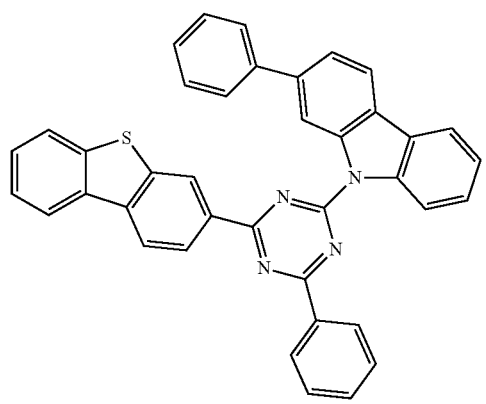
[C-102]
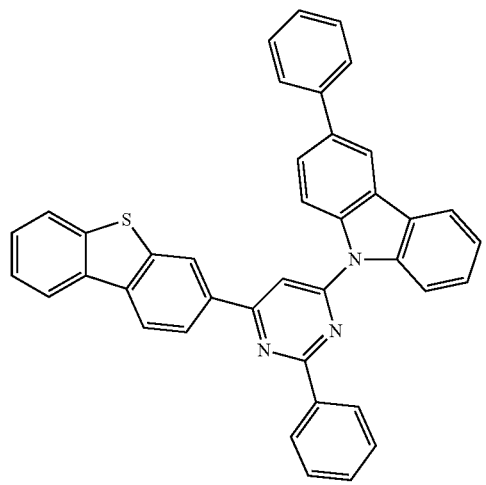
[C-103]
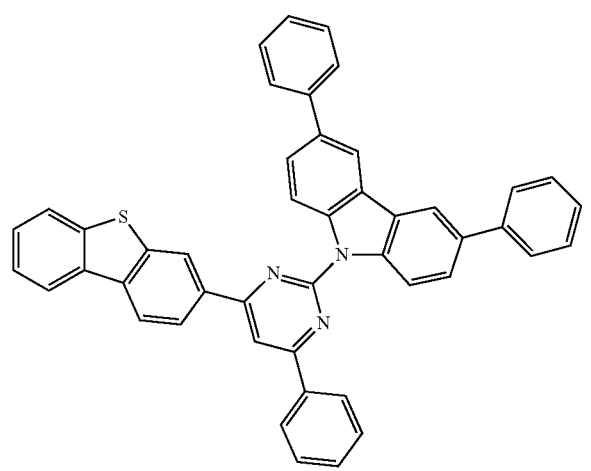
[C-104]
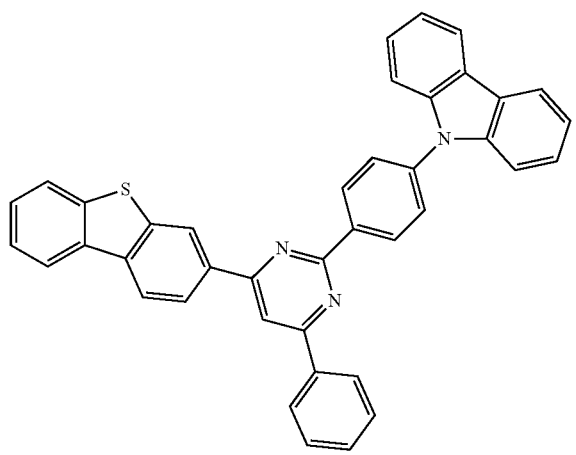
[C-105]
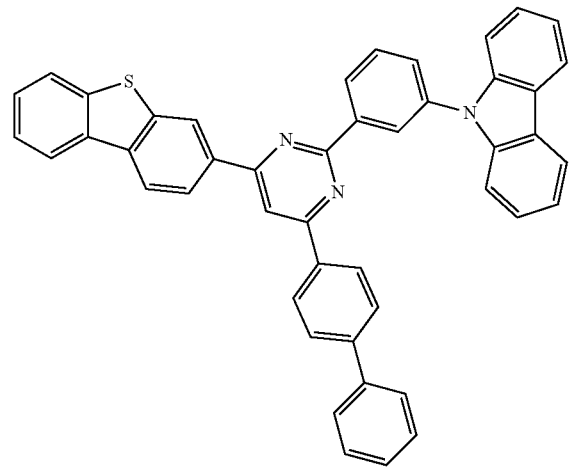
[C-106]

[C-107]
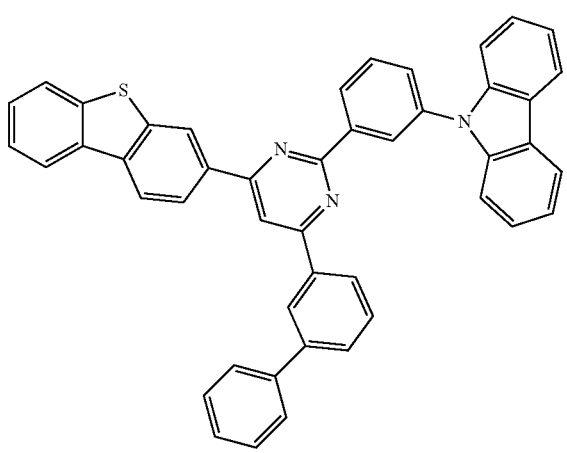

[C-108]
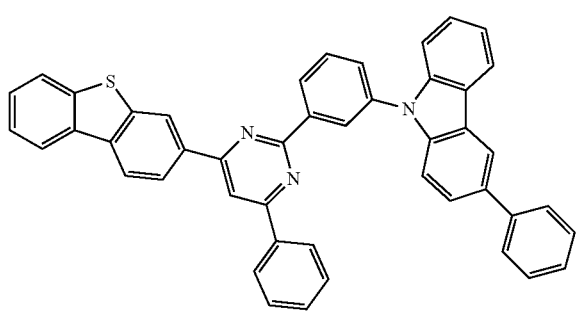

[C-109]
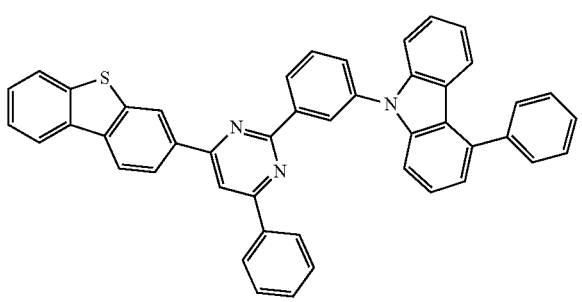

[C-110]
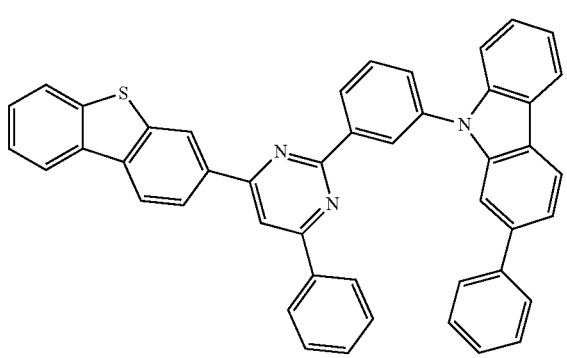

[C-111]
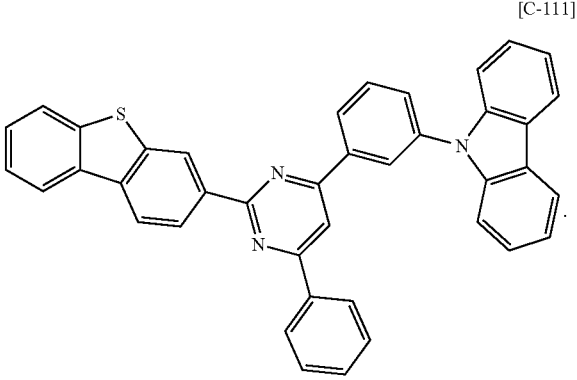

In an implementation, regarding the second host, $Y^1$ and $Y^2$ of Chemical Formula 2 may each independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group, $L^3$ and $L^4$ may each independently be a single bond, a substituted or unsubstituted phenylene group, or a substituted or unsubstituted biphenylene group, $R^5$ to $R^8$ may each independently be hydrogen, deuterium, or a substituted or unsubstituted C6 to C12 aryl group, and m may be 0 or 1.

"Substituted" groups of Chemical Formula 2 may refer to replacement of at least one hydrogen by deuterium, a C1 to C4 alkyl group, a C6 to C18 aryl group, or a C2 to C30 heteroaryl group.

In an implementation, Chemical Formula 2 may include a moiety of Group II, and *-$L^3$-$Y^1$ and *-$L^4$-$Y^2$ may be a substituent of Group III.

[Group II]

C-1
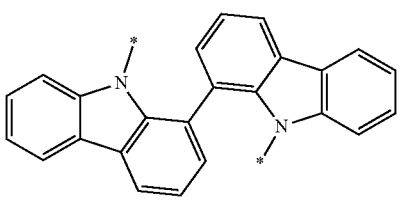

C-2
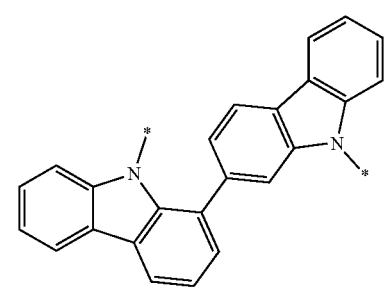

C-3
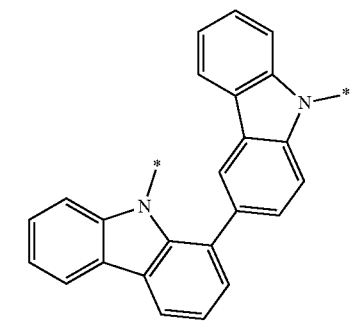
C-4
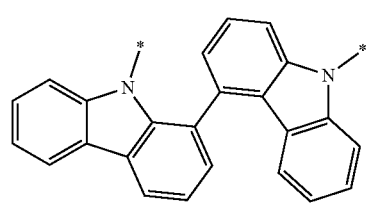
C-5
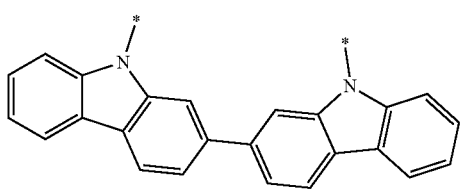
C-6
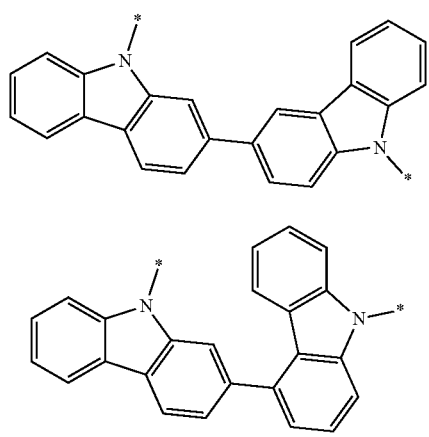
C-7
C-8
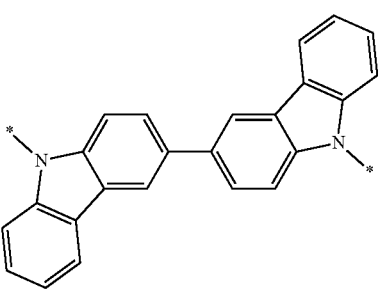
C-9
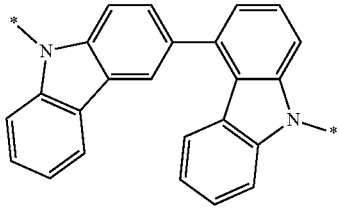
C-10
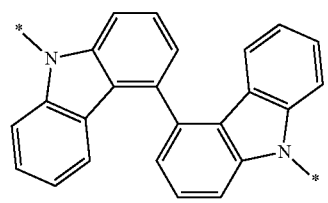
C-11
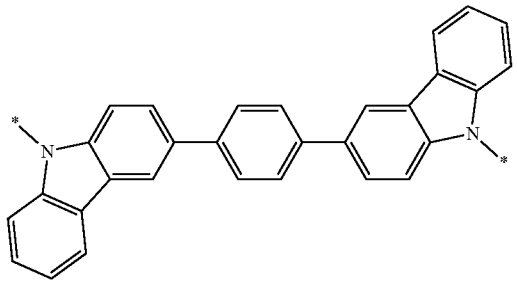
C-12
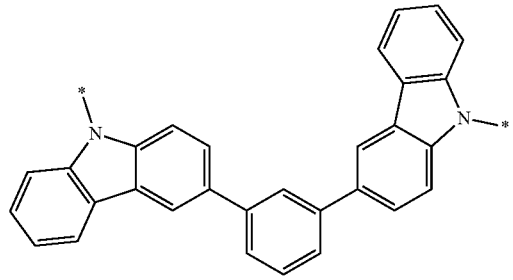
C-13
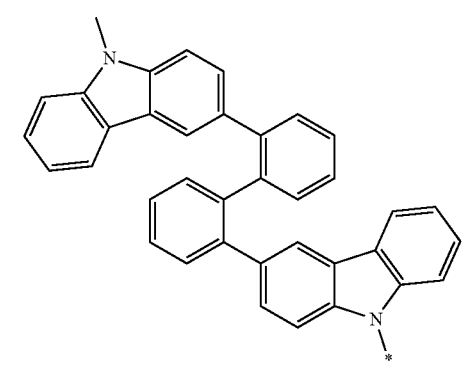

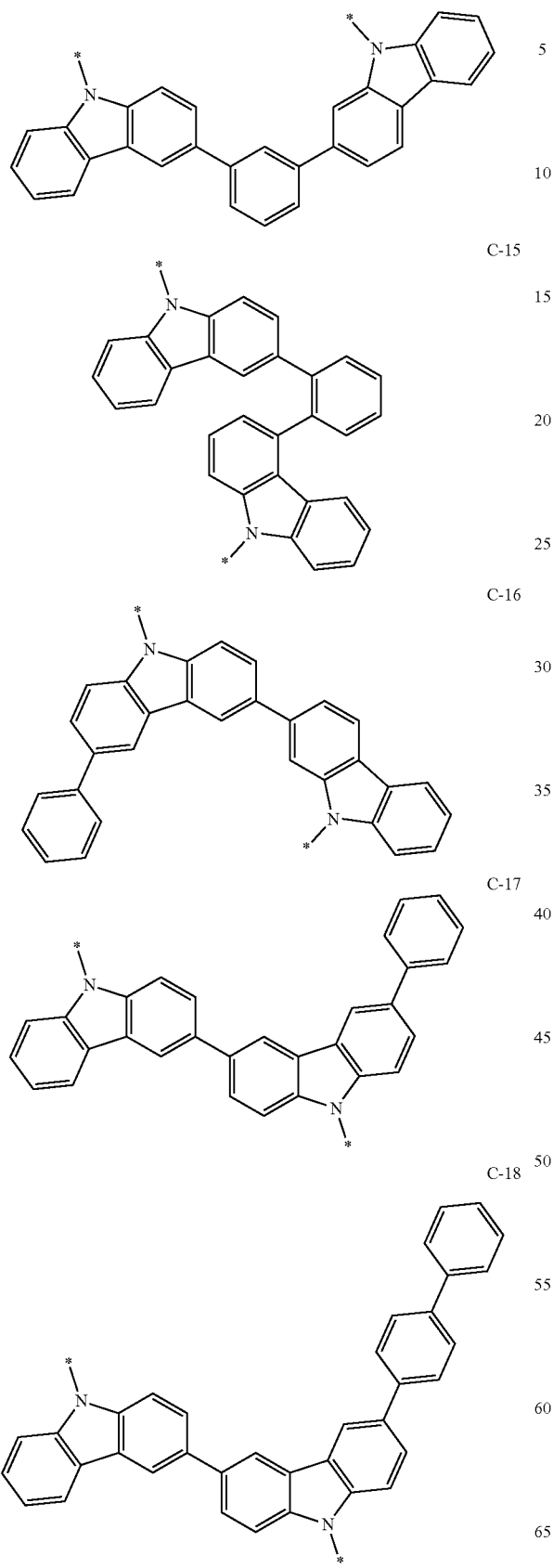
C-14
C-15
C-16
C-17
C-18
[Group III]
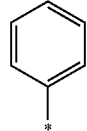 B-1
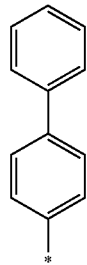 B-2
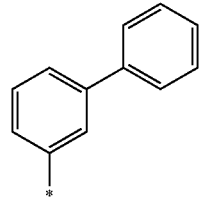 B-3
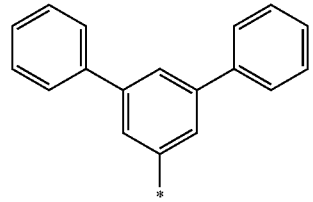 B-4
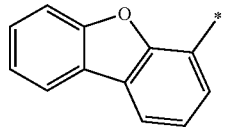 B-5
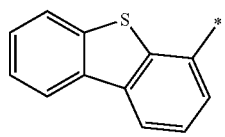 B-6
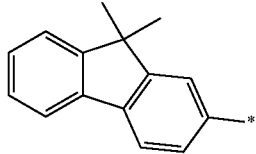 B-7
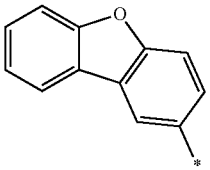 B-8

B-9
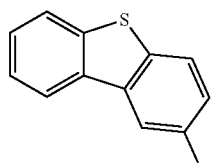
B-10
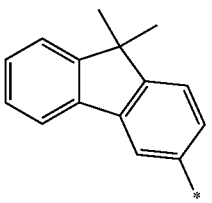
B-11
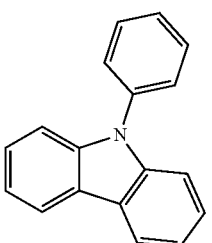
B-12
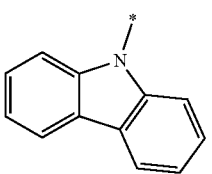
B-13
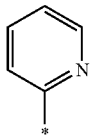
B-14
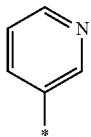
B-15
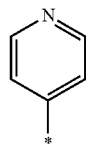
B-16
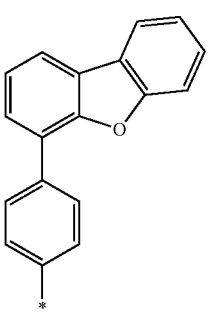
B-17
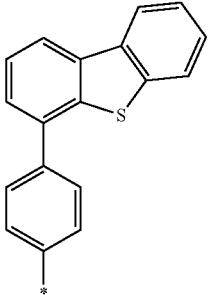
B-18
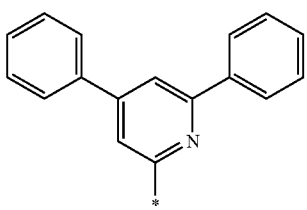
B-19
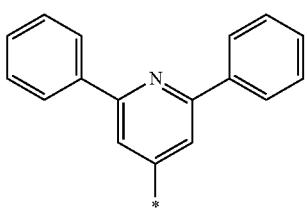
B-20
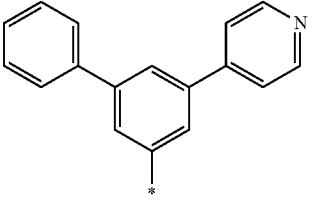
B-21
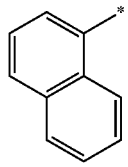
B-22
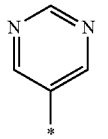
B-23
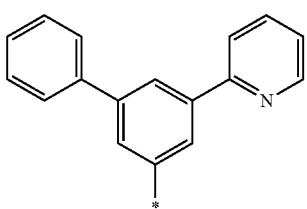

-continued

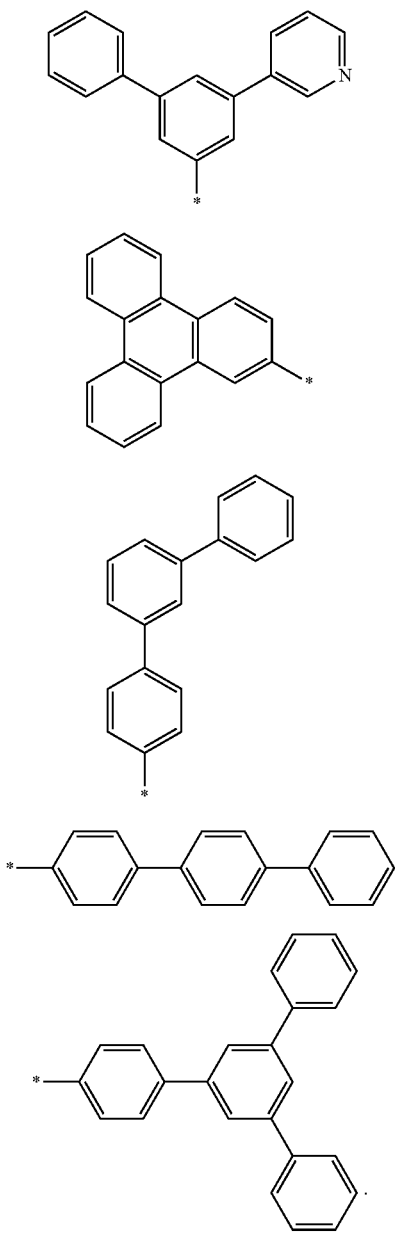

B-24

B-25

B-26

B-27

B-28

In Group II and Group III, * is a linking point.

In an implementation, Chemical Formula 2 may include a moiety represented by Chemical Formula C-8 or Chemical Formula C-17 of Group II and *-L³-Y¹ and *-L⁴-Y² may be selected from Group III.

In an implementation, $Y^1$ and $Y^2$ of Chemical Formula 2 may each independently be a substituted or unsubstituted phenyl group, a substituted or unsubstituted biphenyl group, a substituted or unsubstituted carbazolyl group, a substituted or unsubstituted dibenzofuranyl group, or a substituted or unsubstituted dibenzothiophenyl group. In an implementation, *-L³-Y¹ and *-L⁴-Y² may each independently be selected from B-1, B-2, B-3, B-11, B-16, and B-17 of Group III.

In an implementation, the second host may be, e.g., selected from compounds of Group 2.

[Group 2]

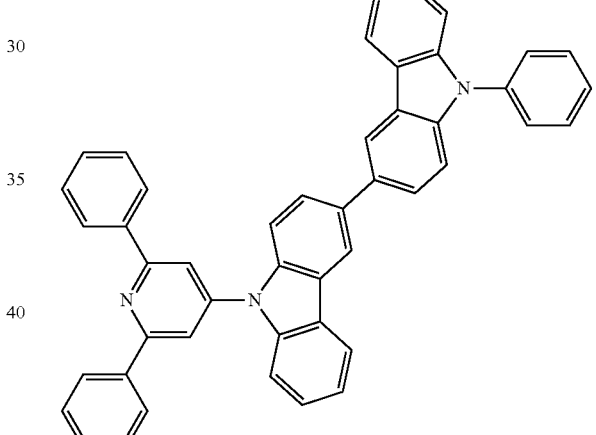

[D-1]

[D-2]

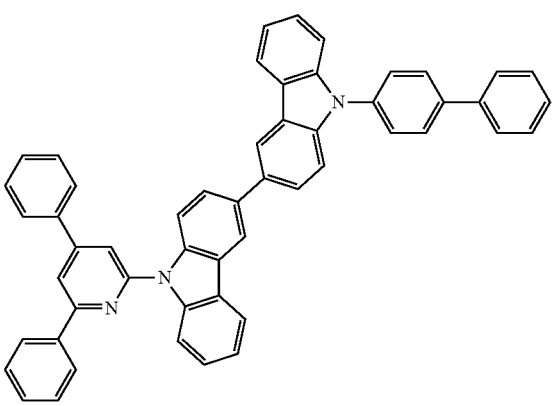

[D-3]

[D-4]
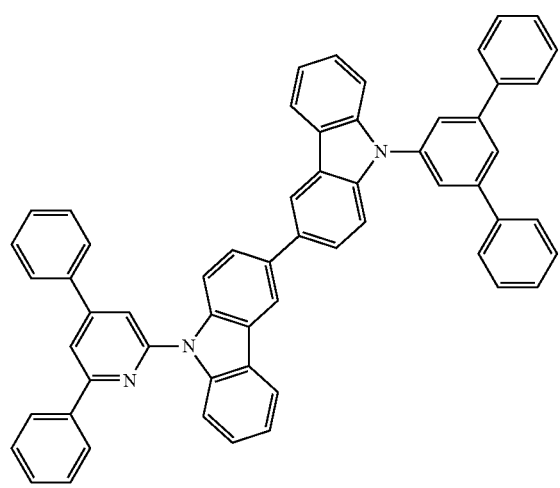
[D-5]
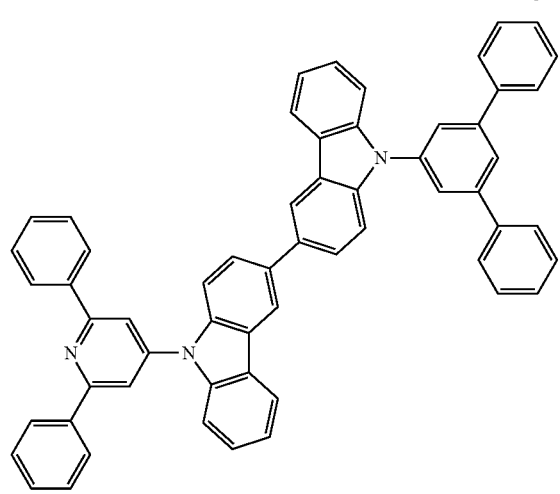
[D-6]
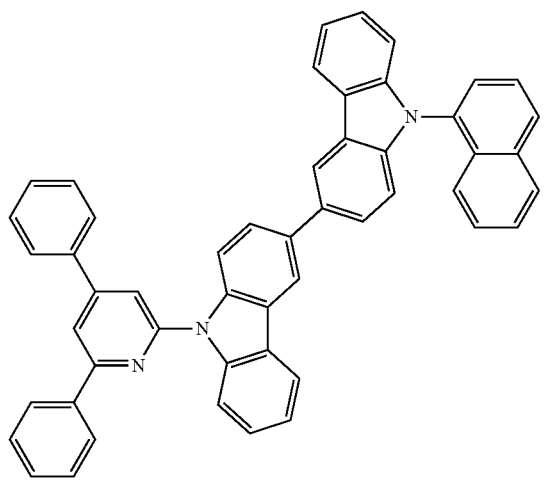
[D-7]
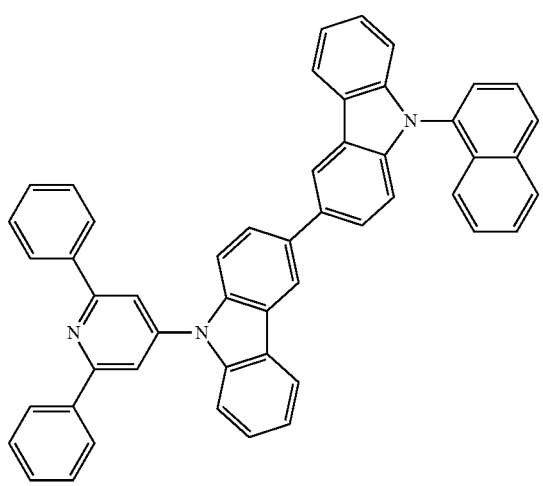
[D-8]
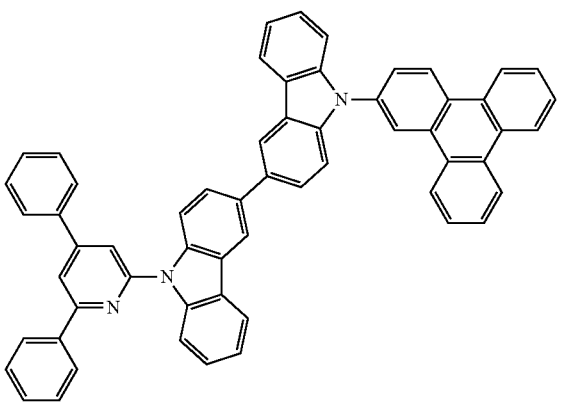
[D-9]
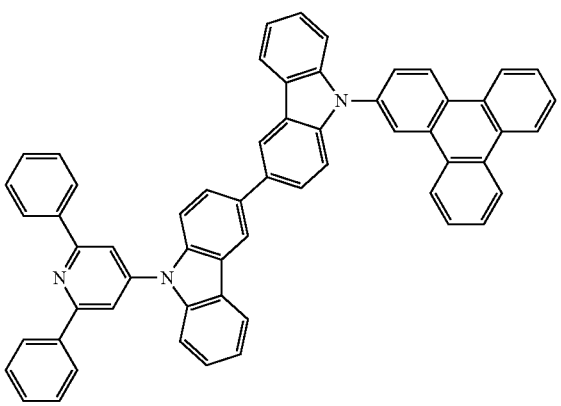

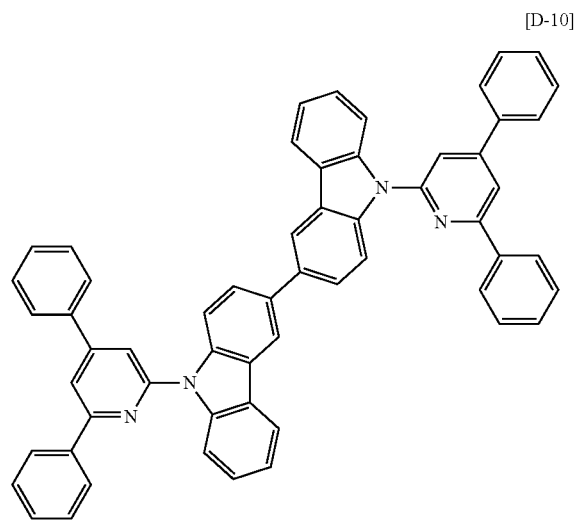
[D-10]
[D-11]
[D-12]
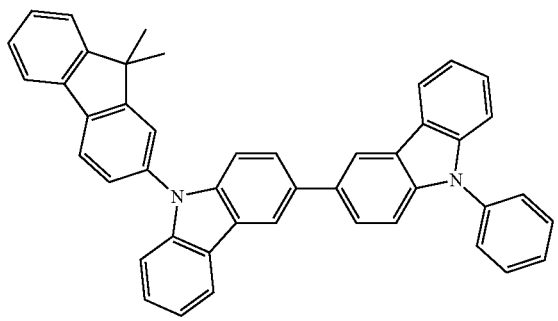
[D-13]
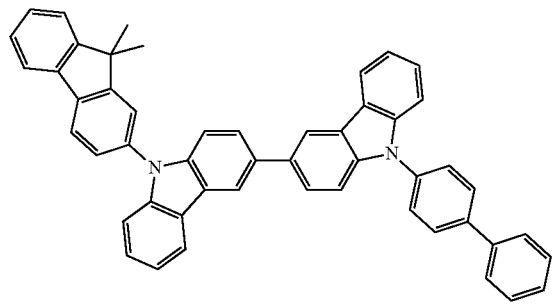
[D-14]
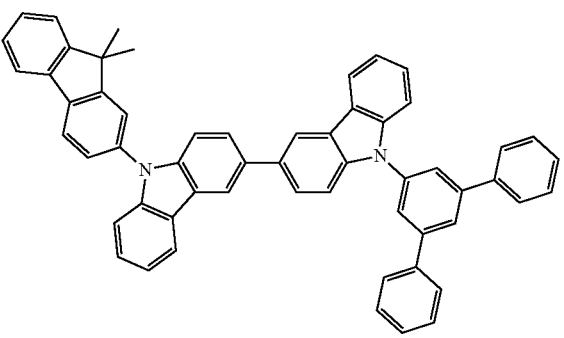
[D-15]
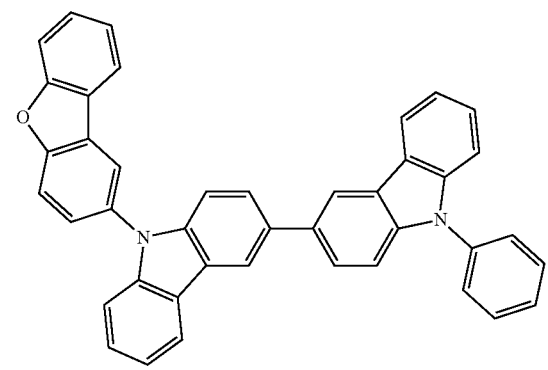
[D-16]

[D-17]
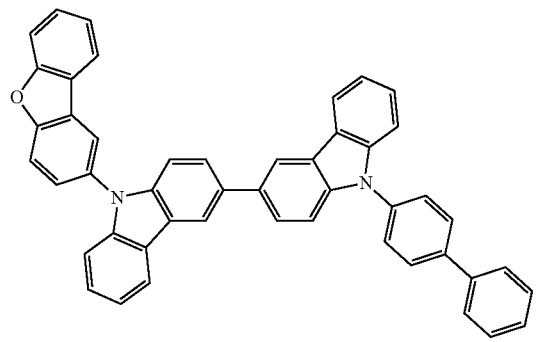
[D-21]
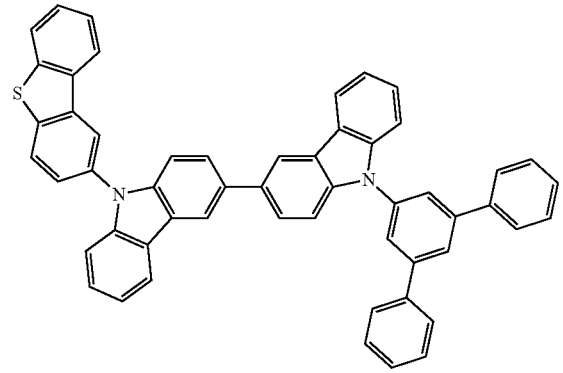
[D-18]
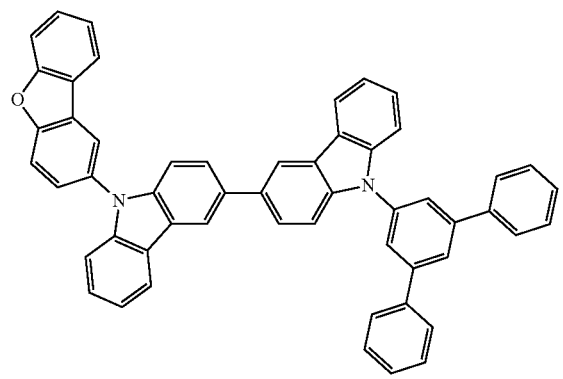
[D-22]
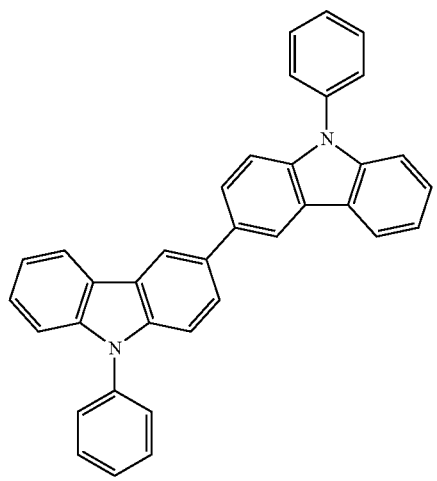
[D-19]
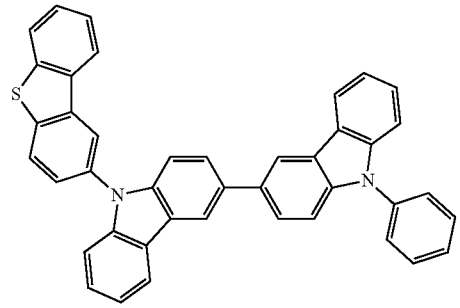
[D-20]
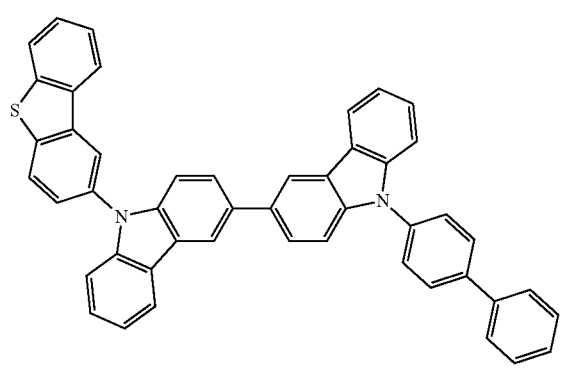
[D-23]
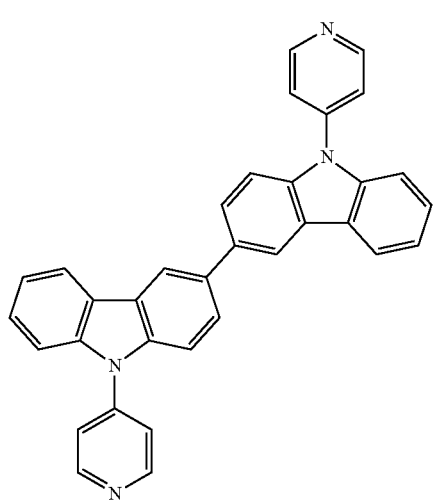

-continued
[D-24]
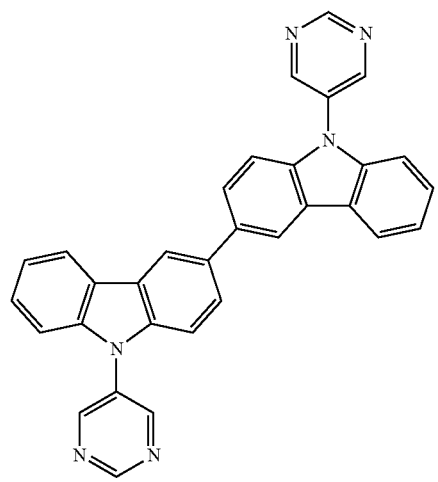
[D-25]
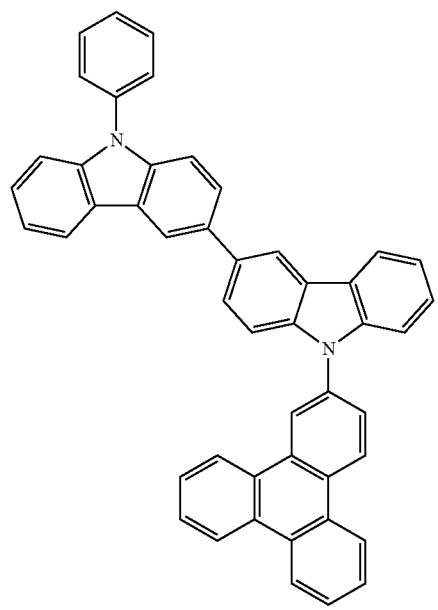
[D-26]
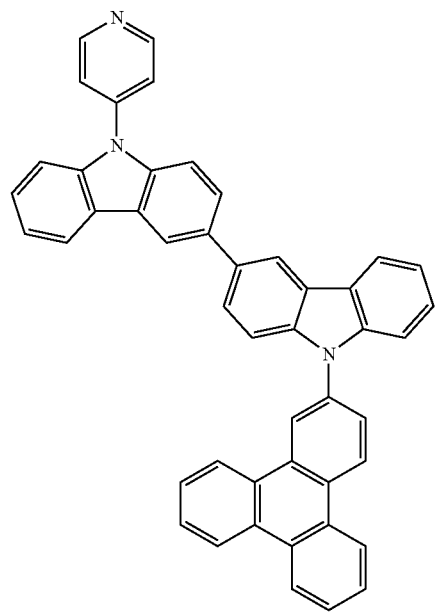
[D-27]
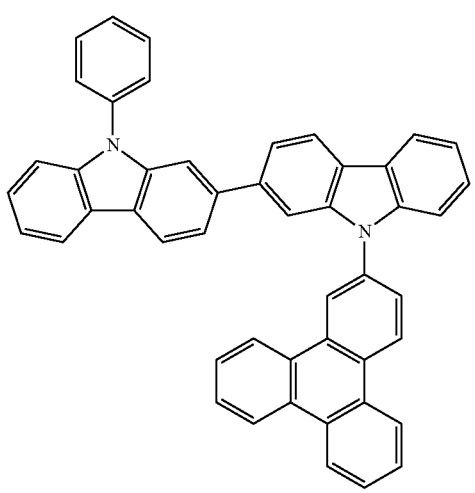
[D-28]
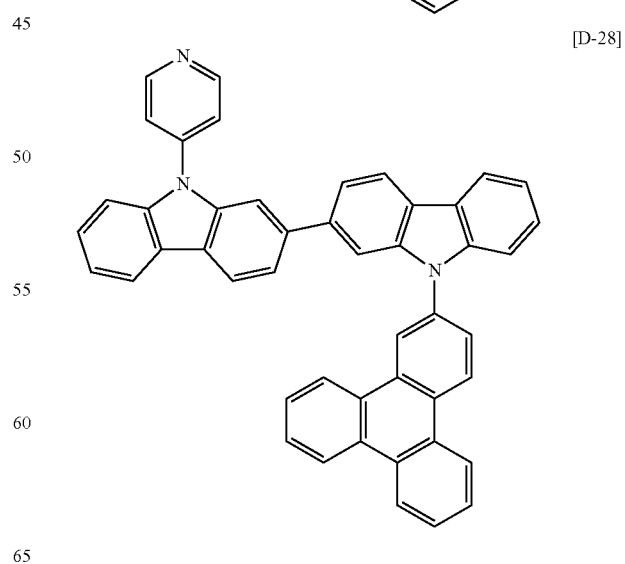

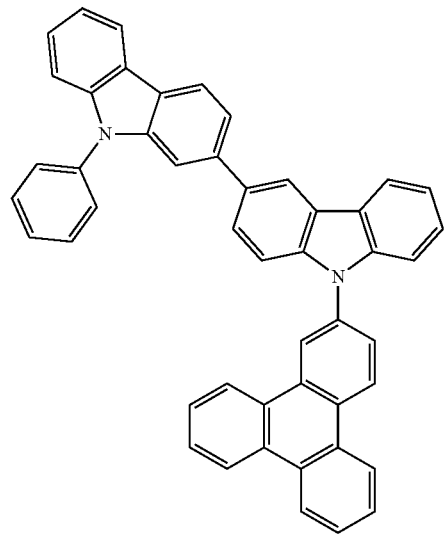
[D-29]
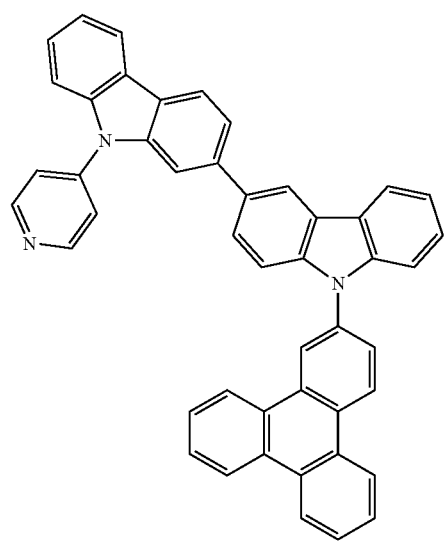
[D-30]
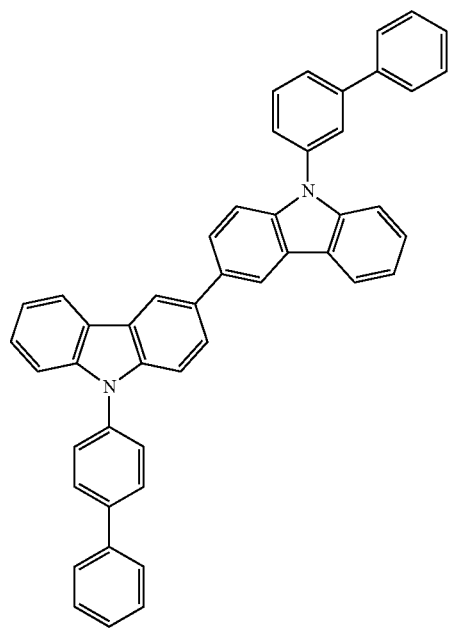
[D-31]
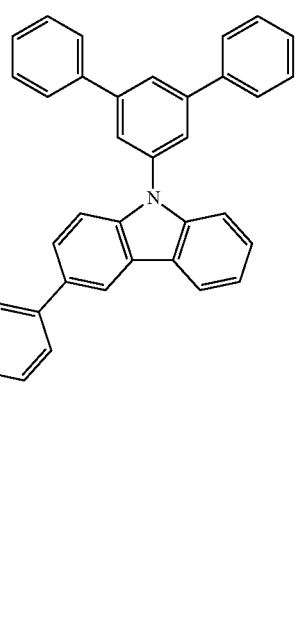
[D-32]

[D-33]
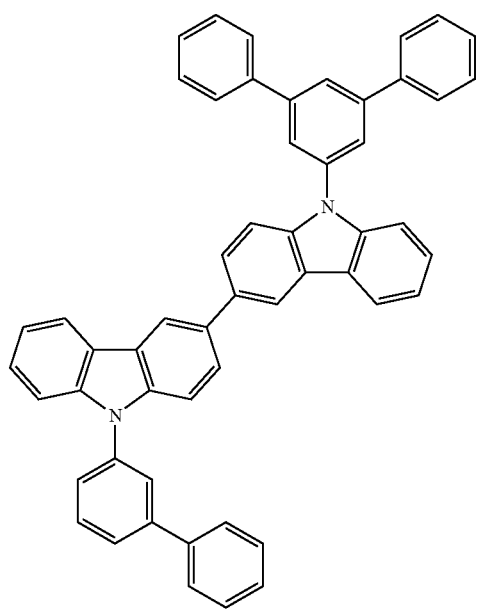
[D-35]
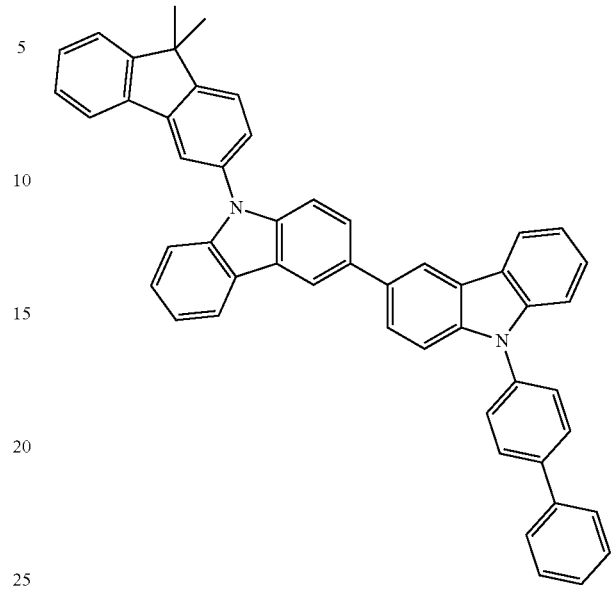
[D-36]
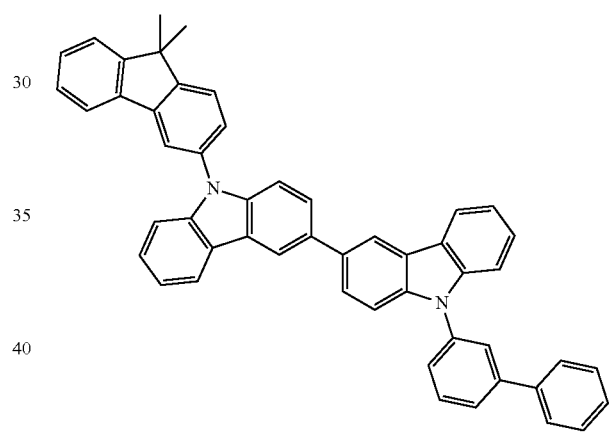
[D-34]
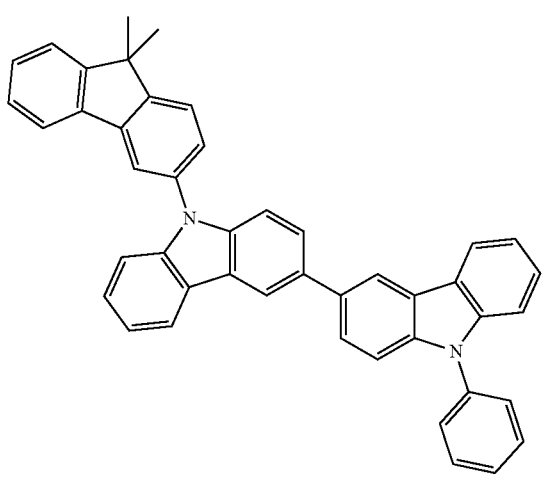
[D-37]
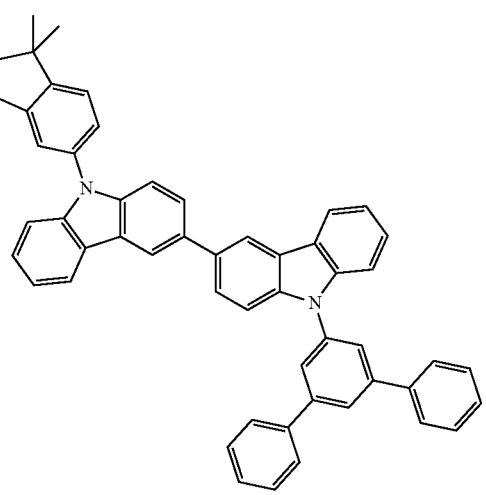

-continued
[D-38]
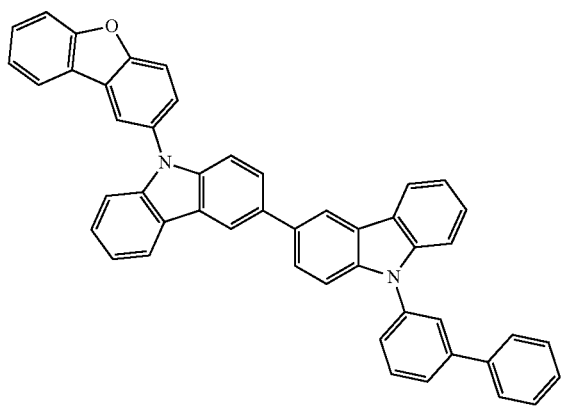
[D-39]
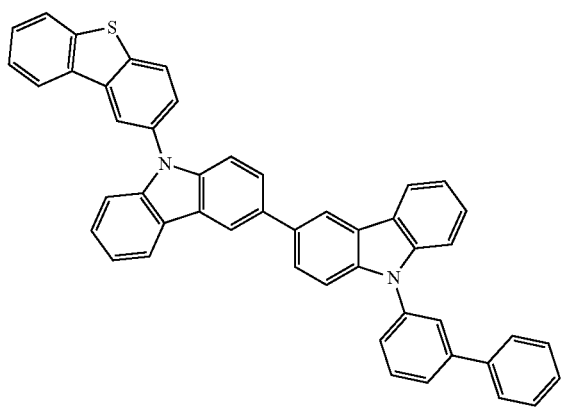
[D-40]
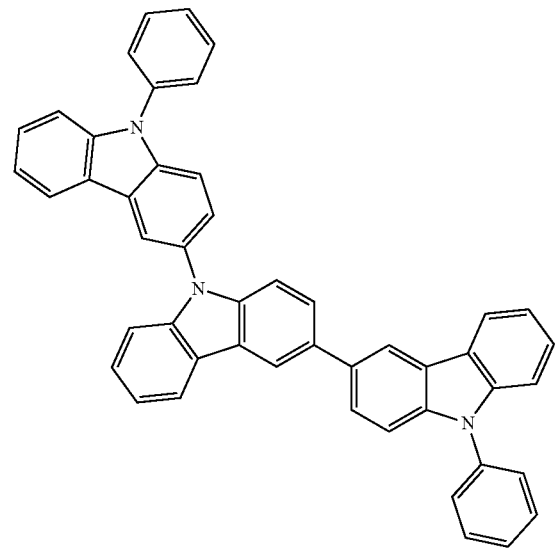
-continued
[D-41]
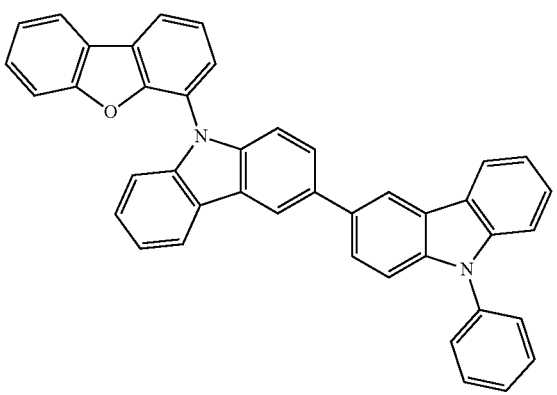
[D-42]
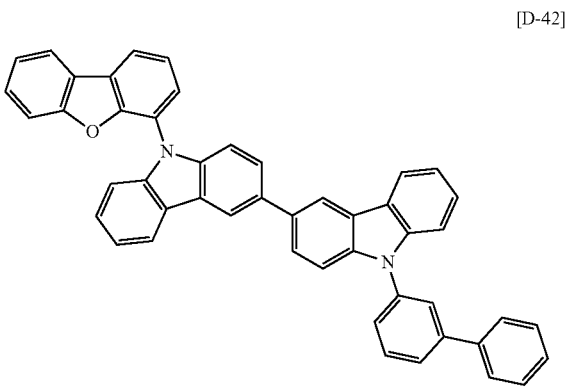
[D-43]
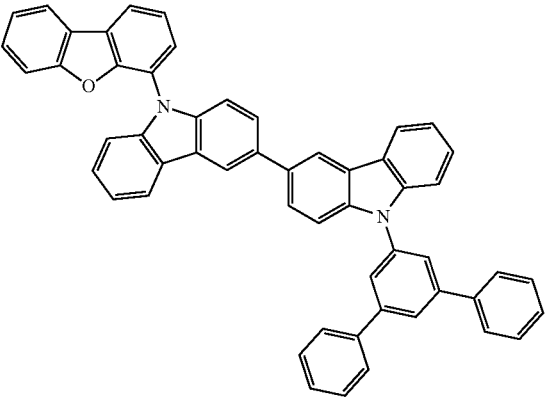

-continued
[D-44]
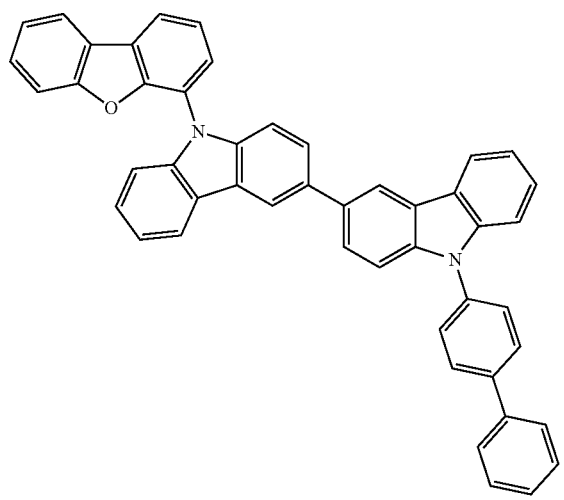
[D-45]
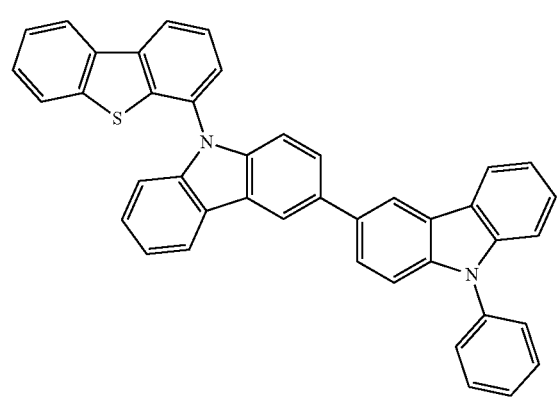
[D-46]
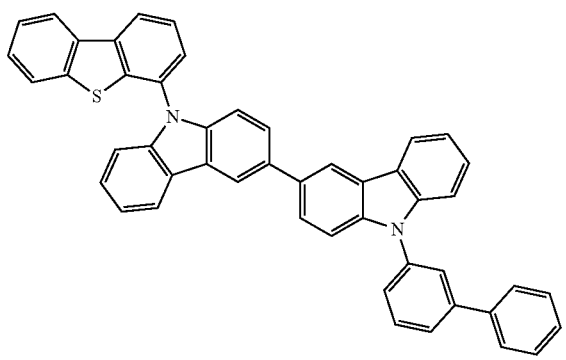
-continued
[D-47]
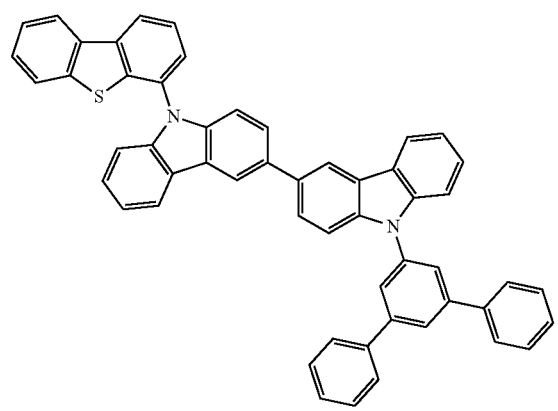
[D-48]
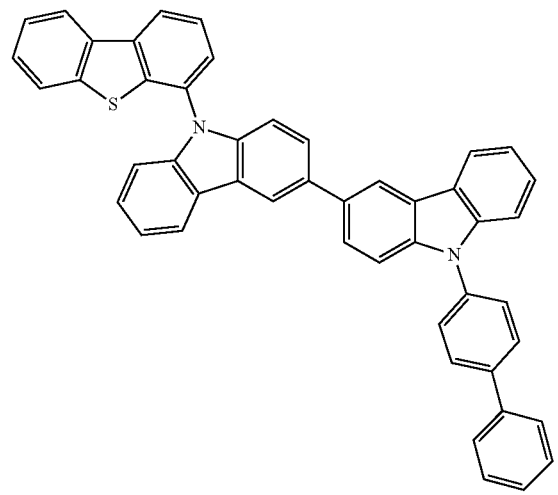
[D-49]
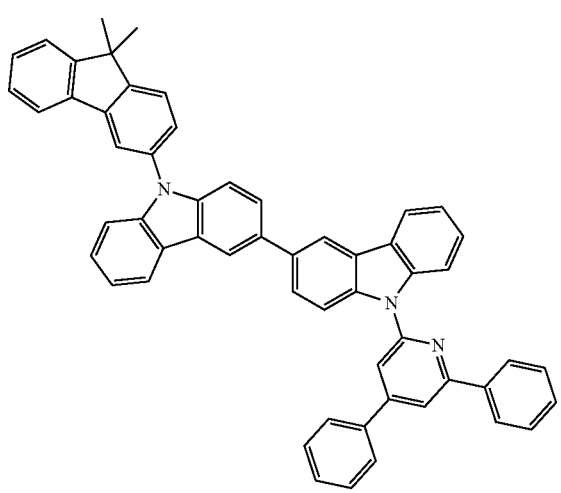

[D-50]
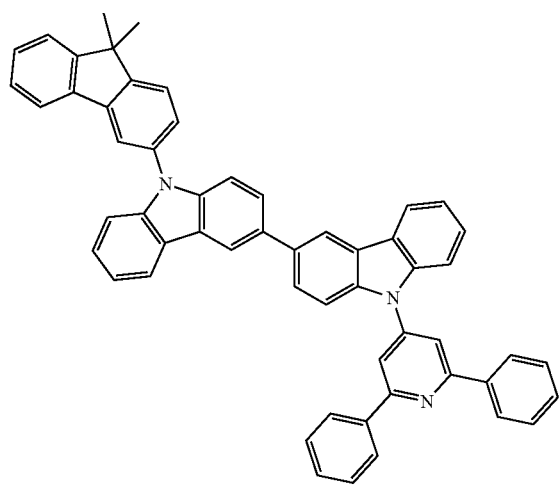
[D-53]
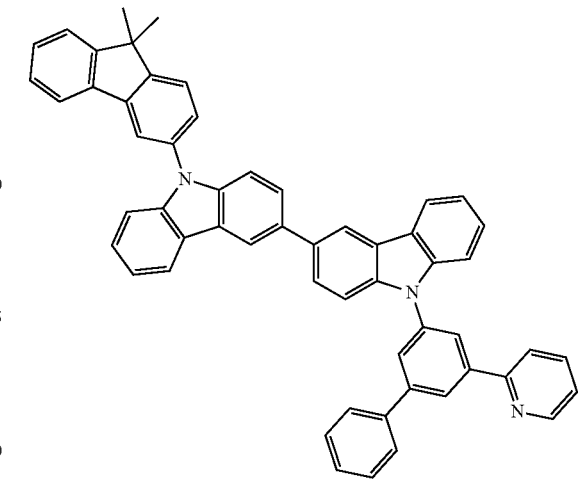
[D-51]
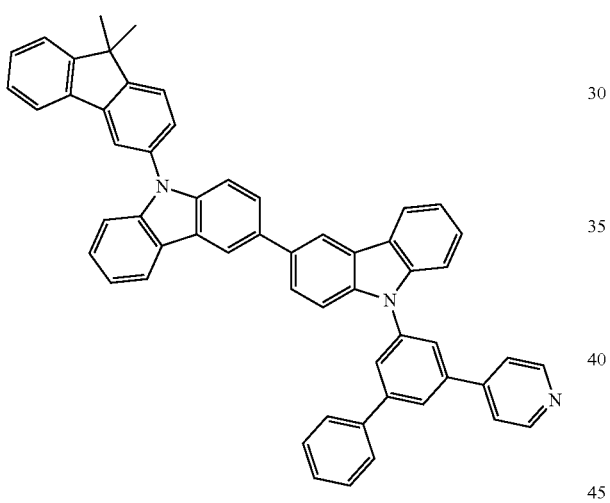
[D-54]
[D-52]
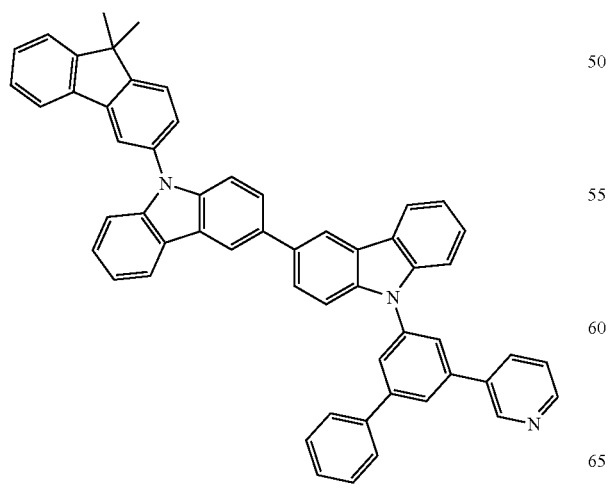
[D-55]

[D-56]
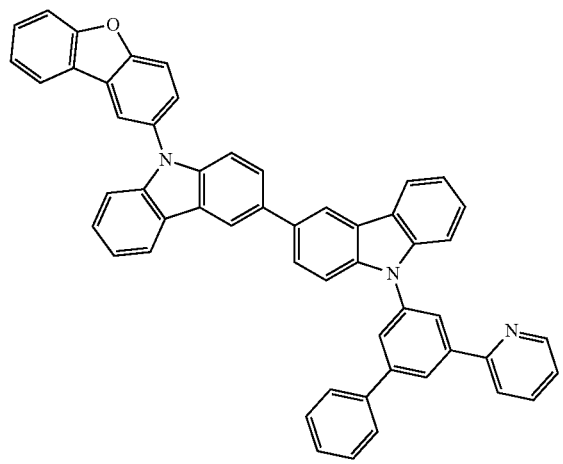
[D-57]
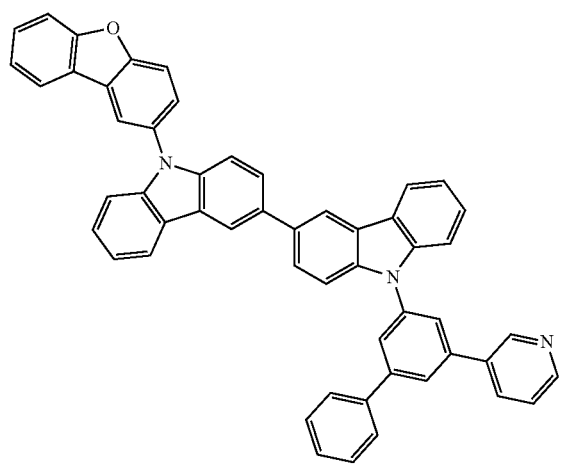
[D-58]
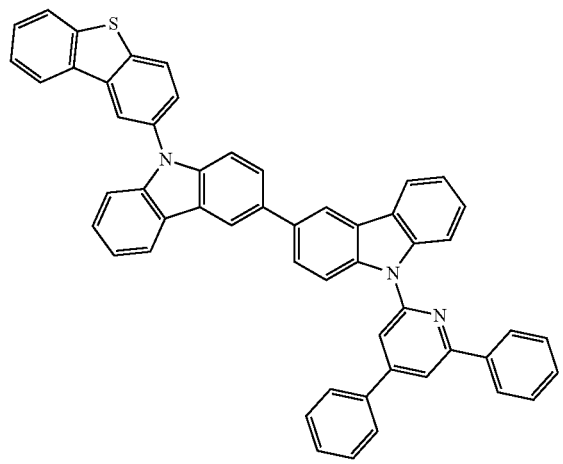
[D-59]
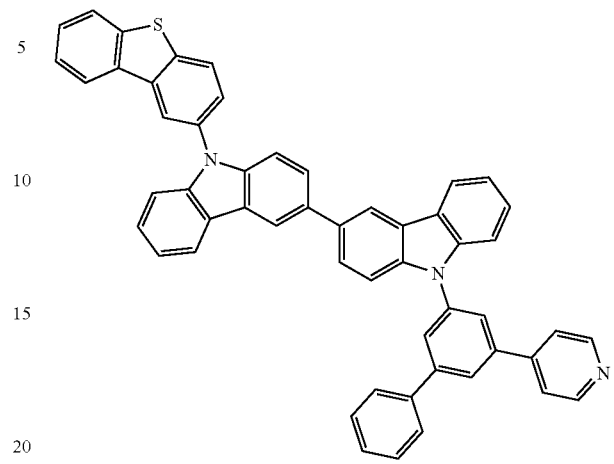
[D-60]
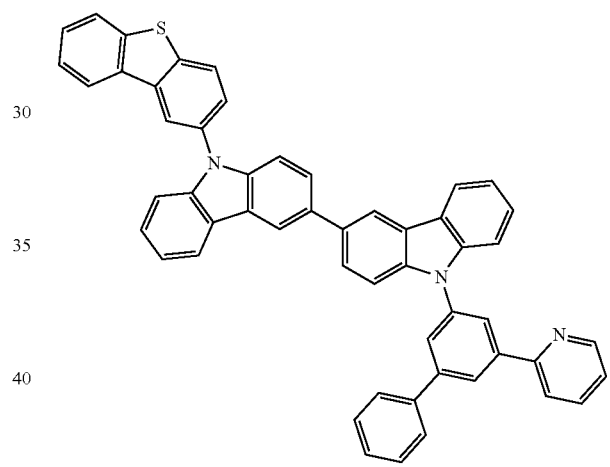
[D-61]
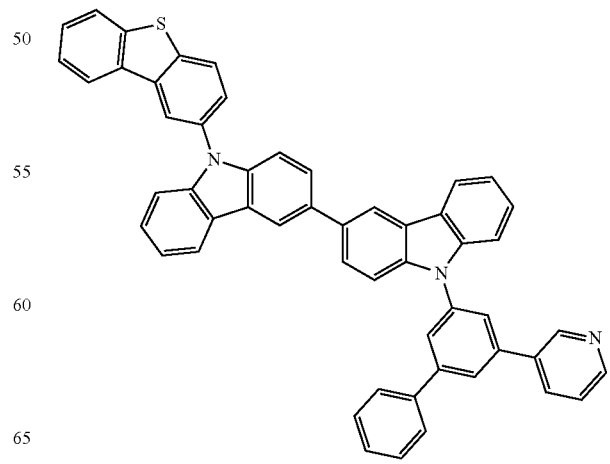

[D-62]
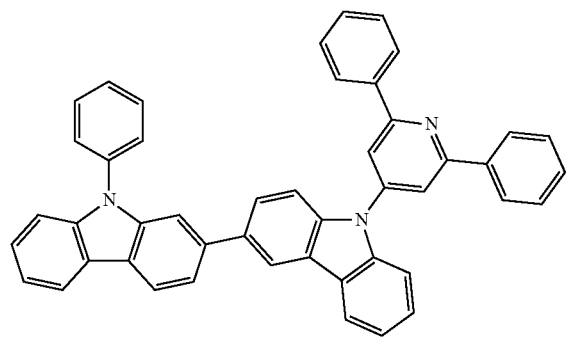
[D-63]
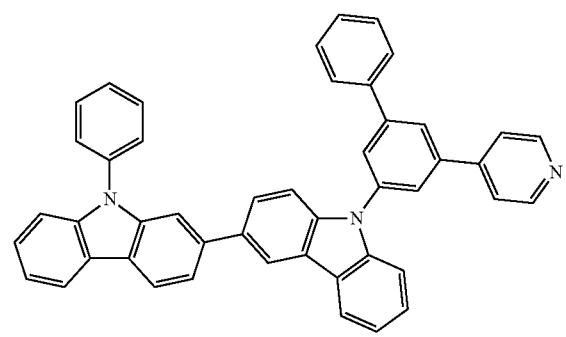
[D-64]
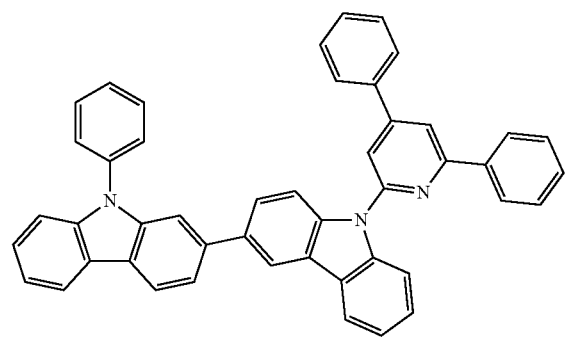
[D-65]
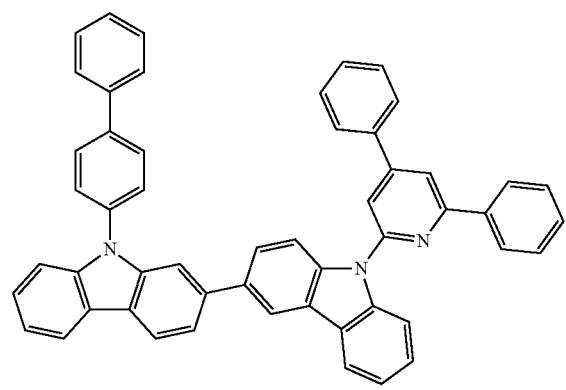
[D-66]
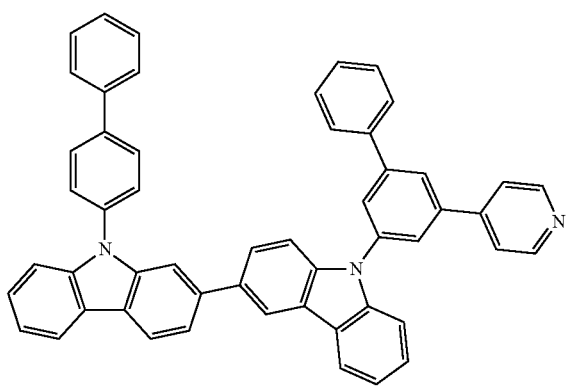
[D-67]
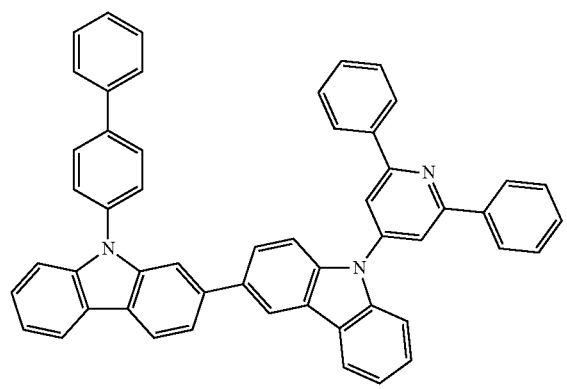
[D-68]
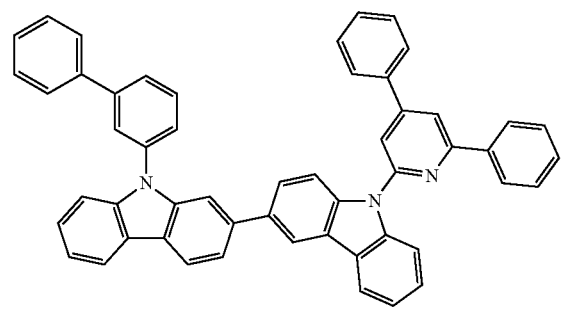
[D-69]
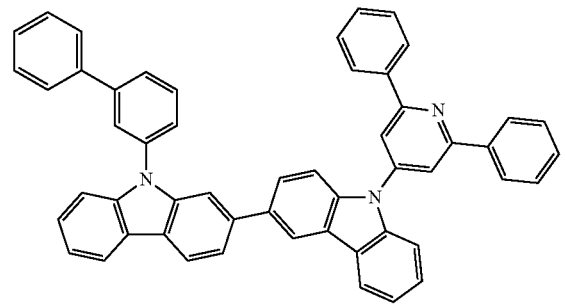

[D-70]
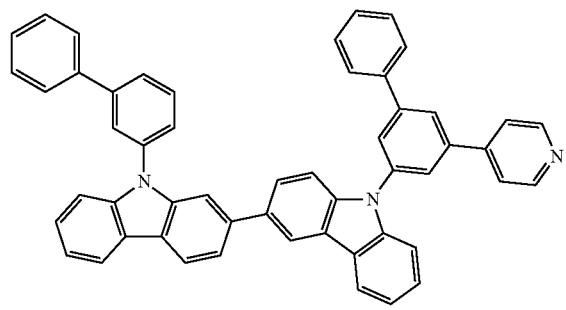
[D-74]
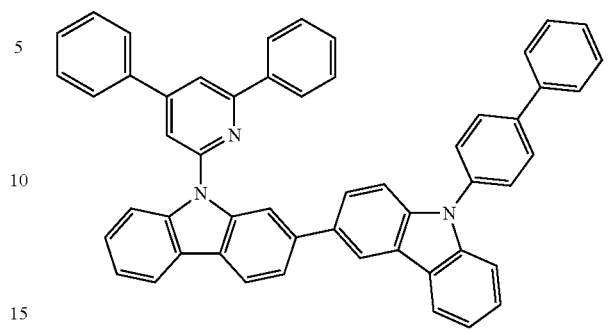
[D-71]
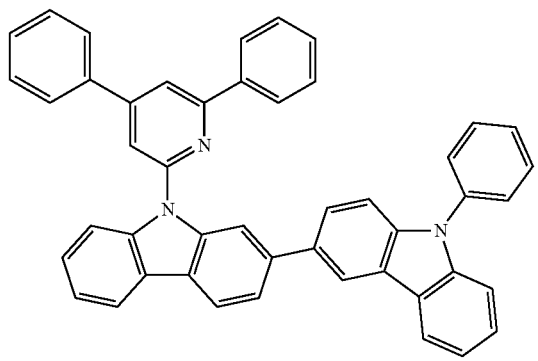
[D-75]
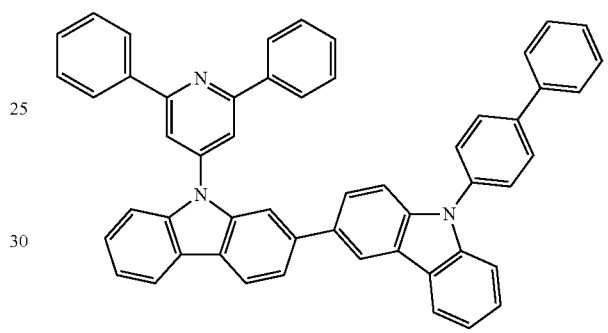
[D-72]
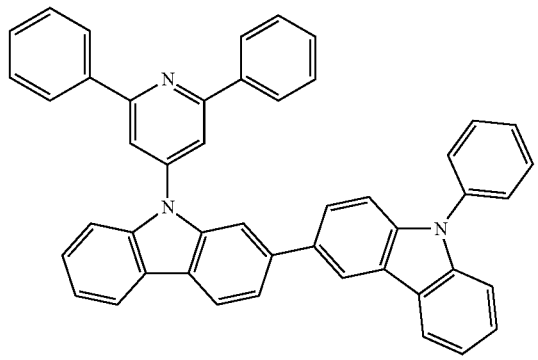
[D-76]
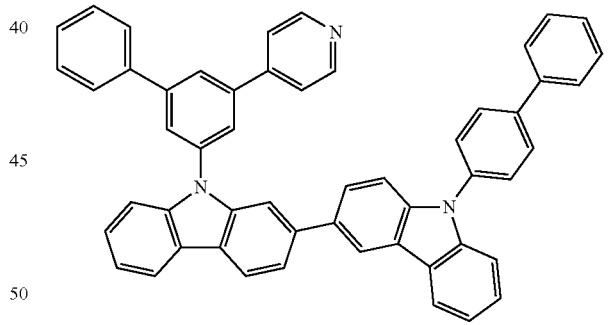
[D-73]
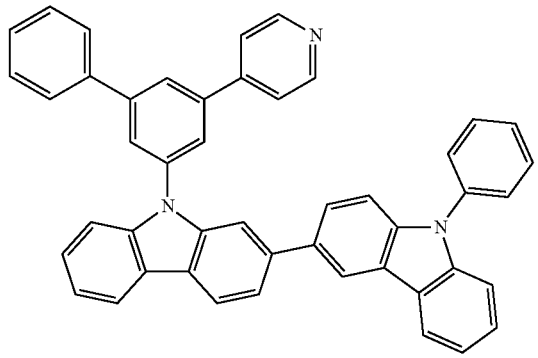
[D-77]
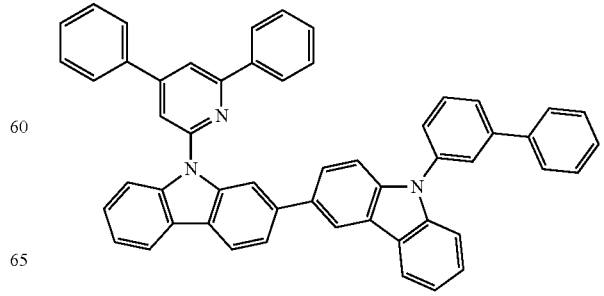

[D-78]
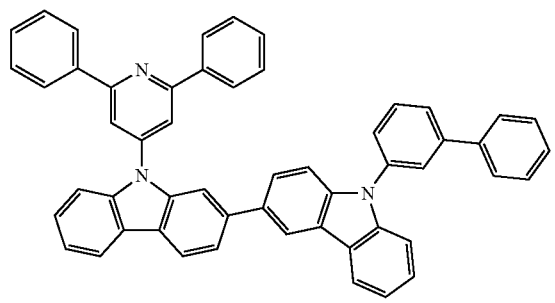
[D-82]
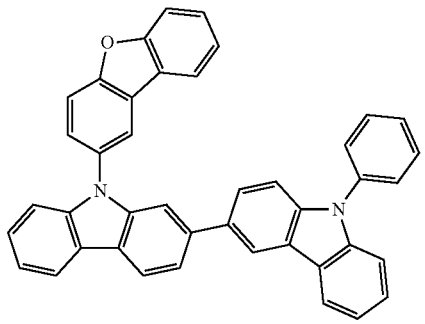
[D-79]
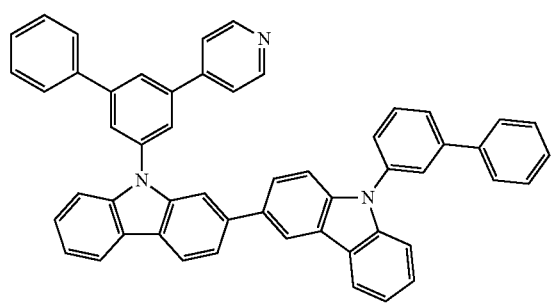
[D-83]
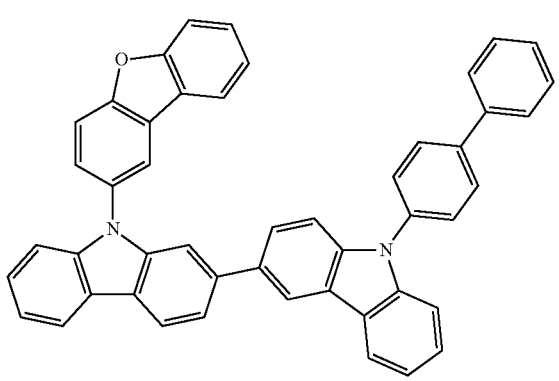
[D-80]
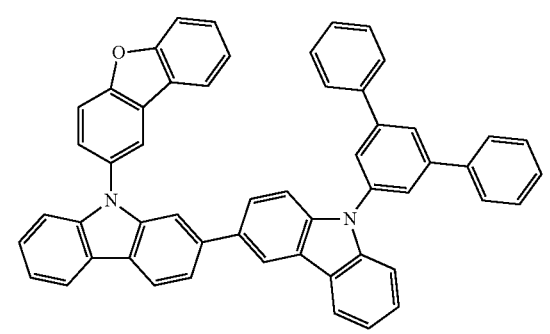
[D-84]
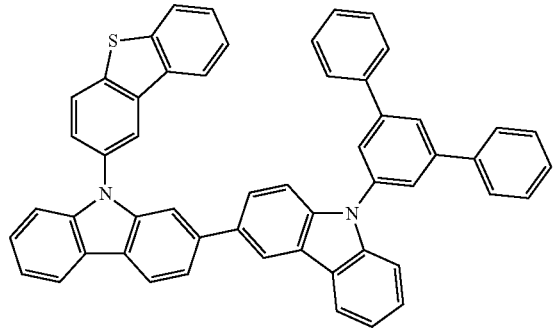
[D-81]
[D-85]
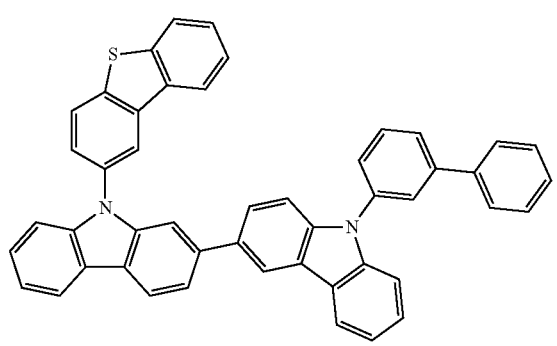

[D-86]
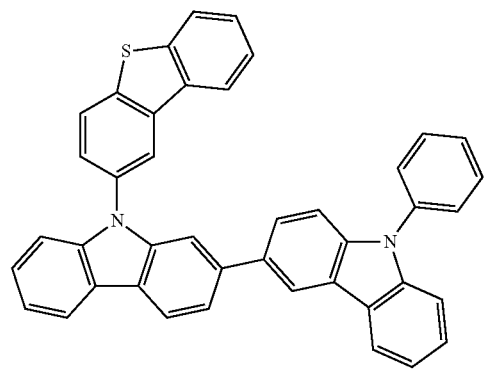
[D-90]
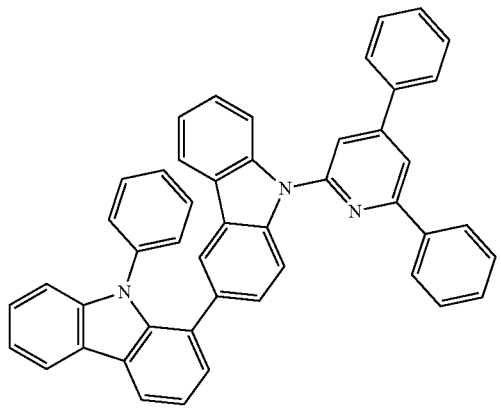
[D-87]
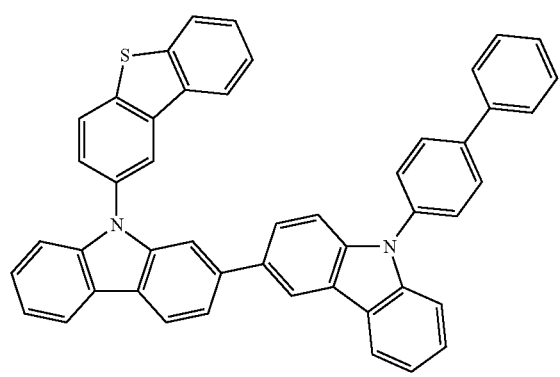
[D-91]
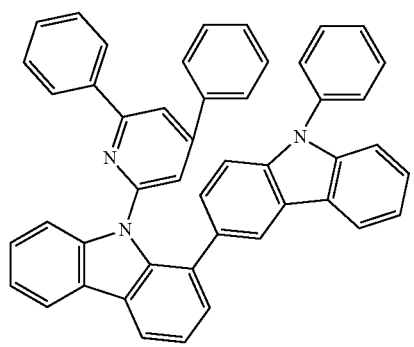
[D-88]
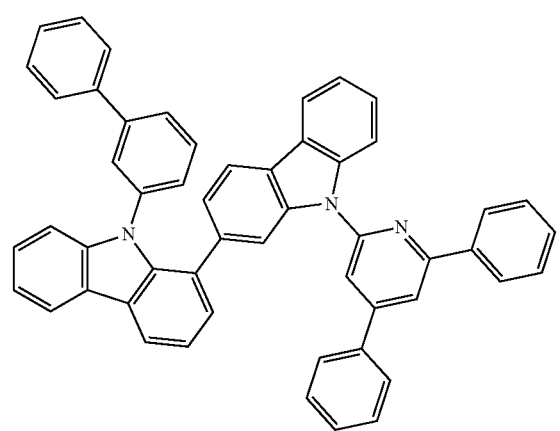
[D-92]
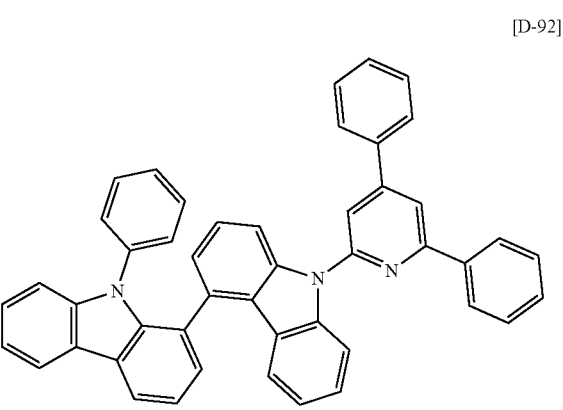
[D-89]
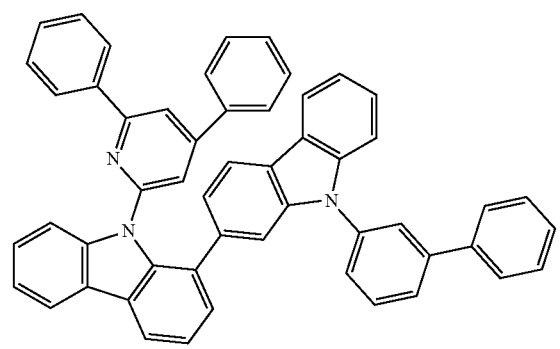
[D-93]
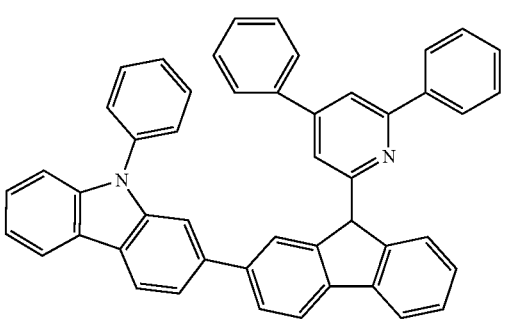

[D-94]
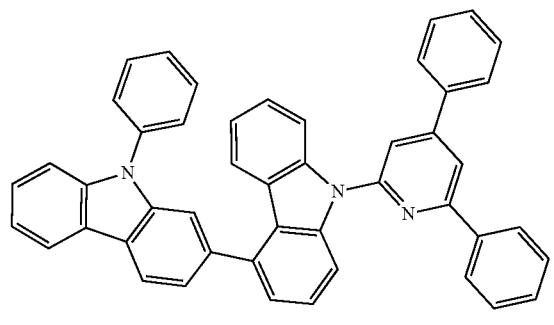
[D-98]
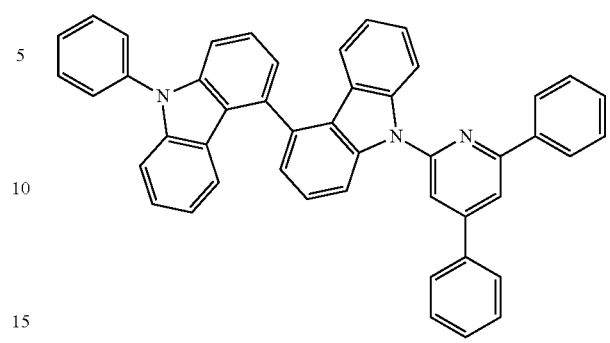
[D-95]
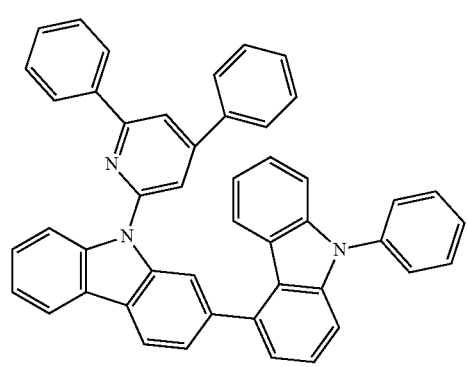
[D-99]
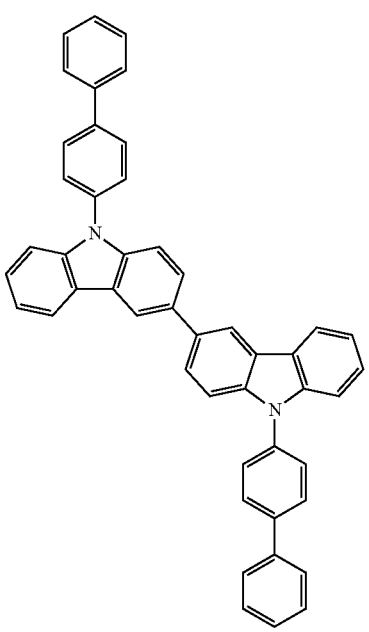
[D-96]
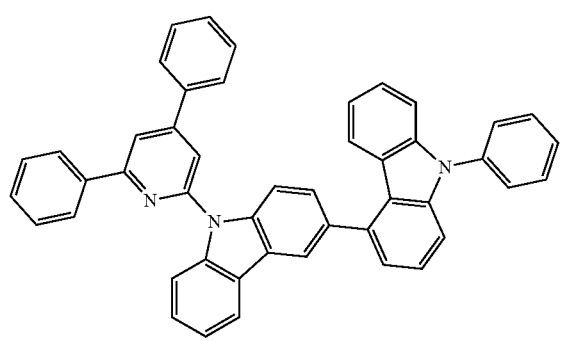
[D-97]
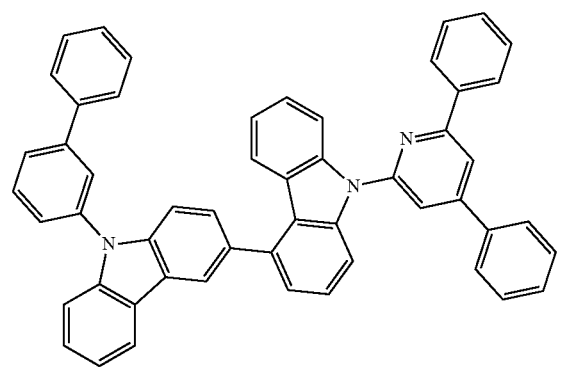
[D-100]

[D-101]
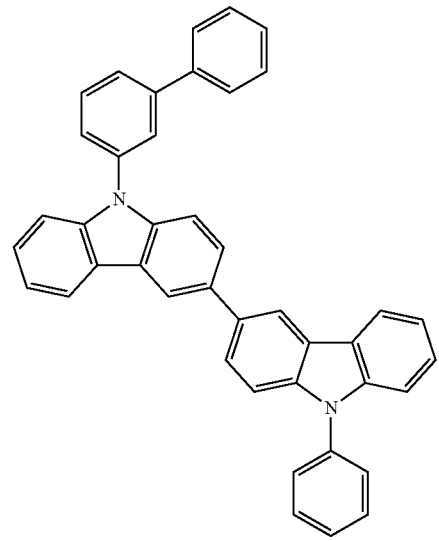
[D-102]
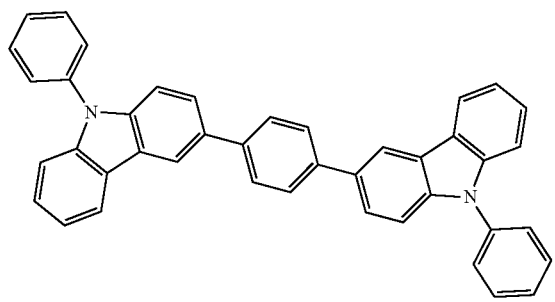
[D-103]
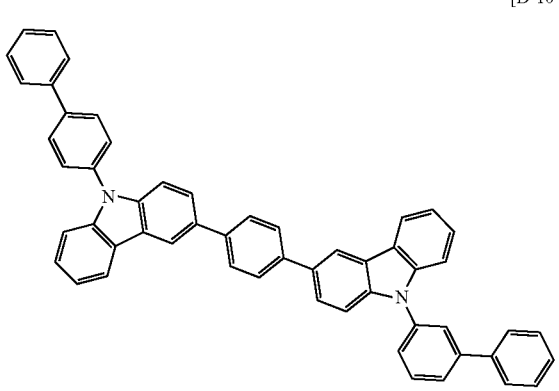
[D-104]
[D-105]
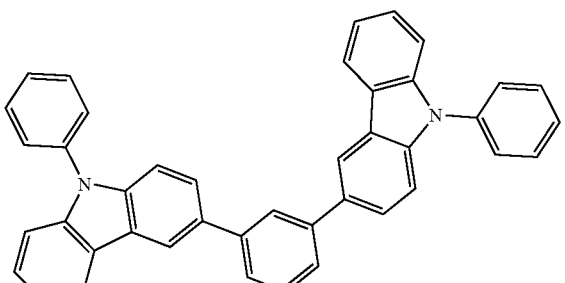
[D-106]
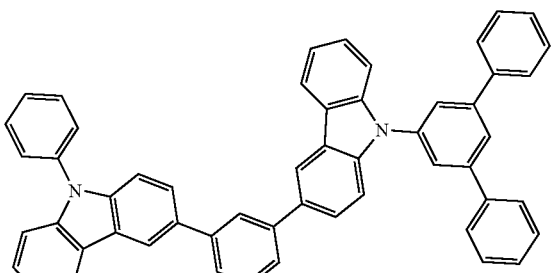
[D-107]
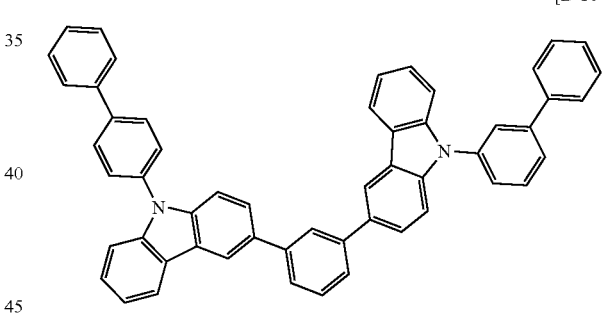
[D-108]
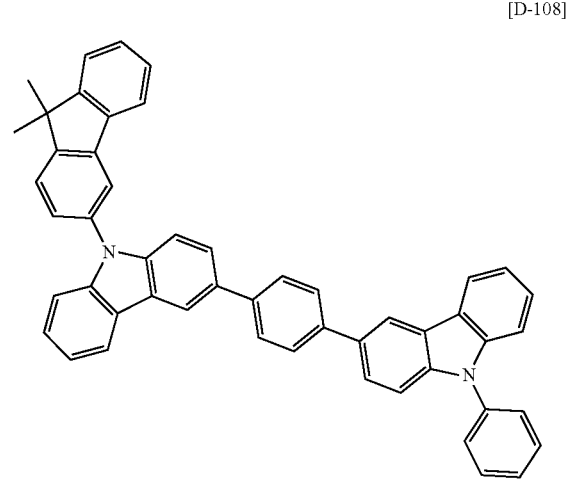

-continued
[D-109]
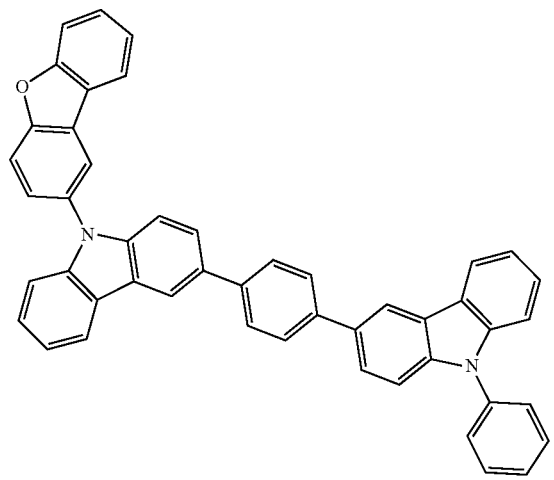
[D-110]
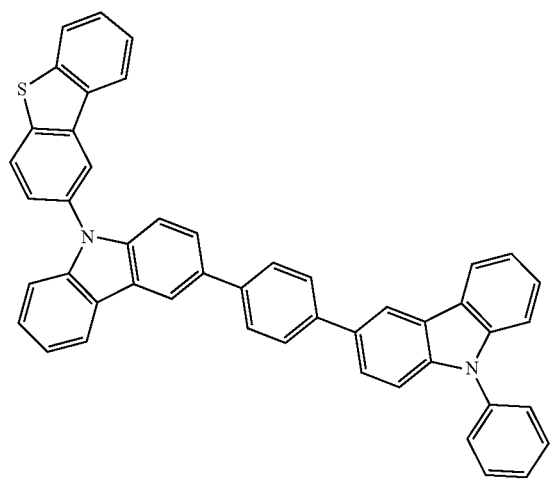
[D-111]
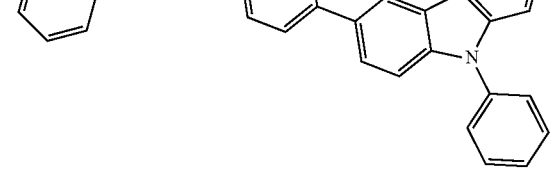
-continued
[D-112]
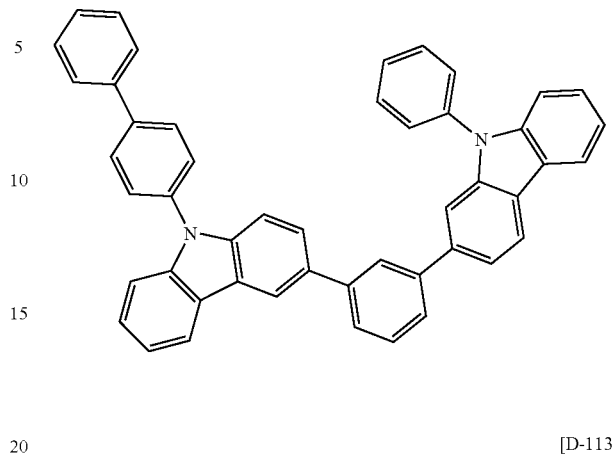
[D-113]
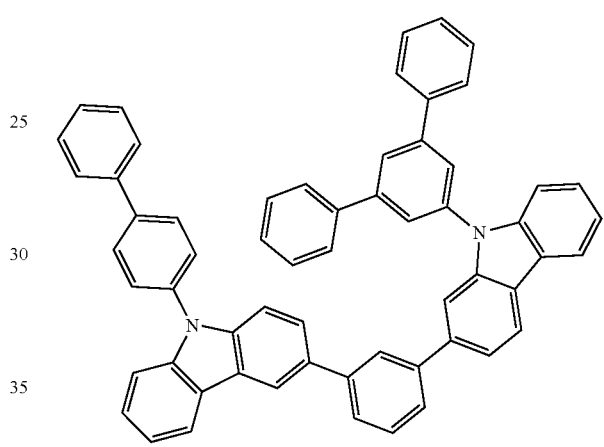
[D-114]
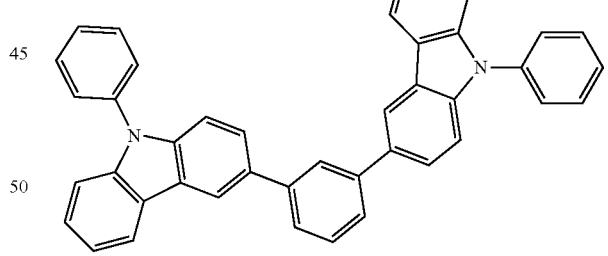
[D-115]
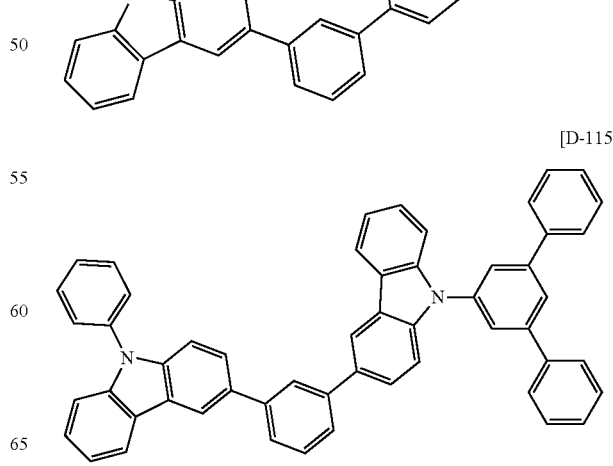

[D-116]
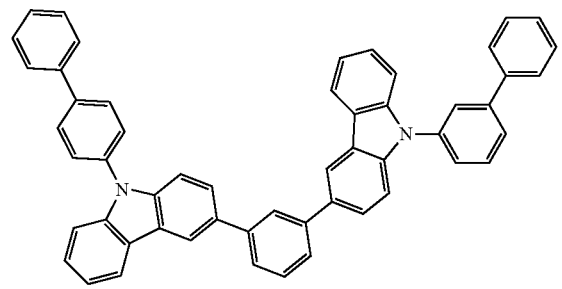
[D-117]
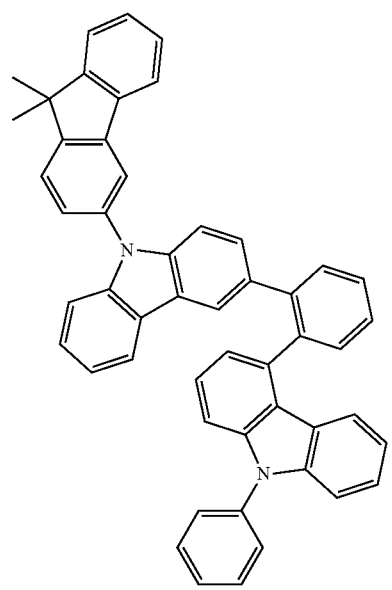
[D-118]
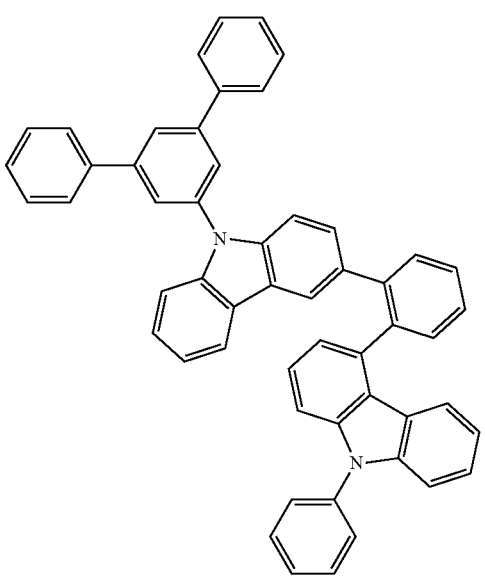
[D-119]
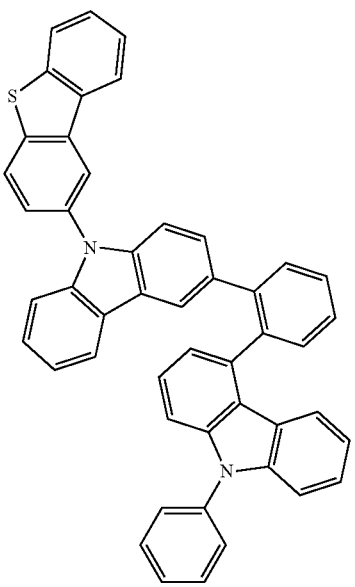
[D-120]
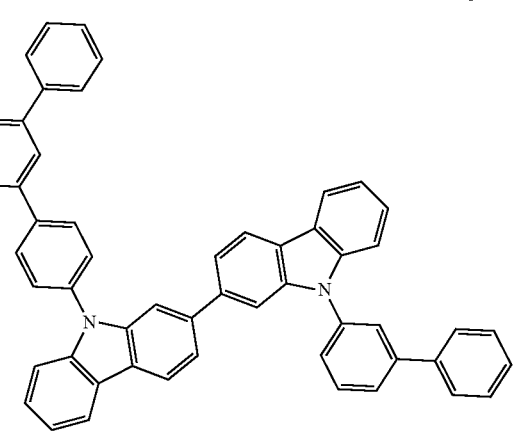
[D-121]
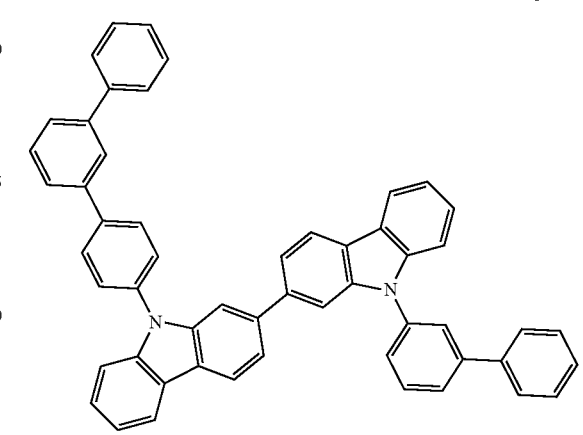

[D-122]
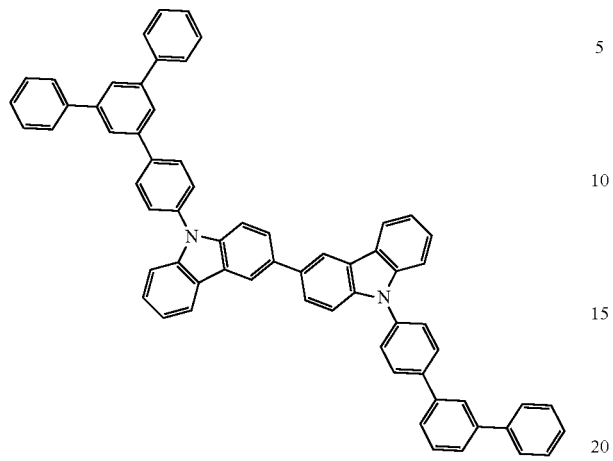
[D-125]
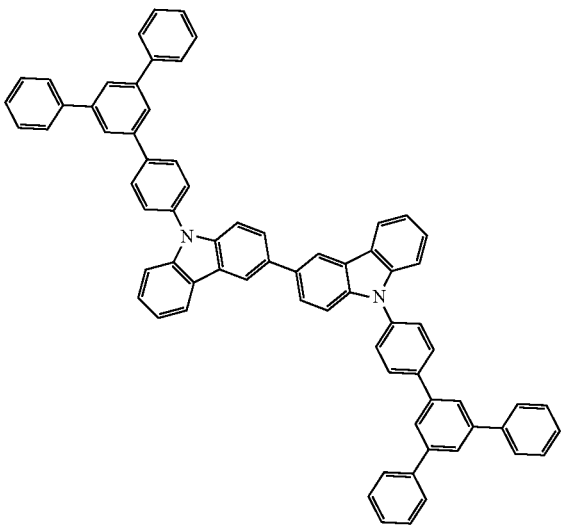
[D-123]
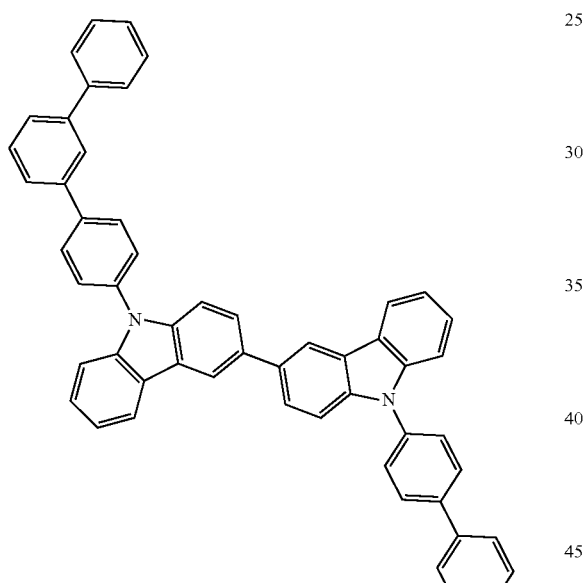
[D-124]
[D-126]
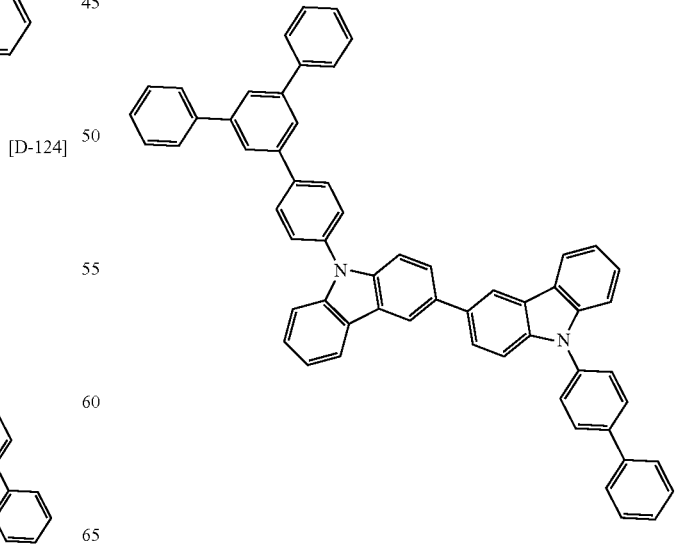

[D-127]
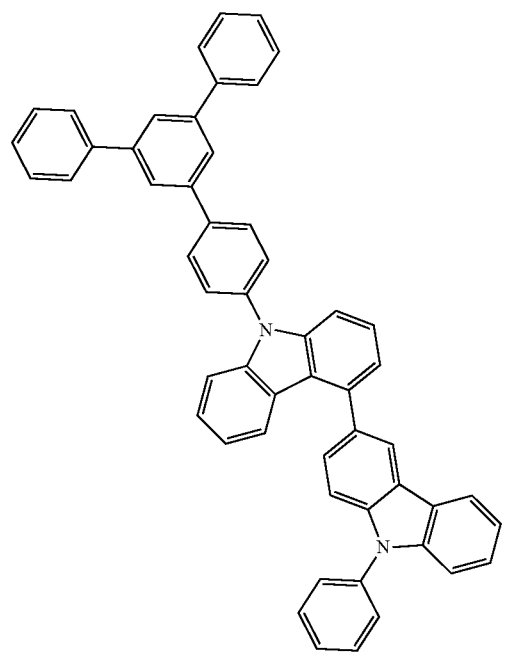
[D-128]
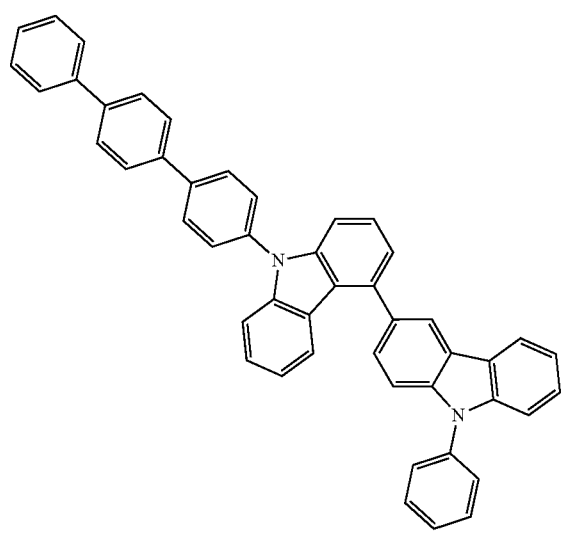
[D-129]
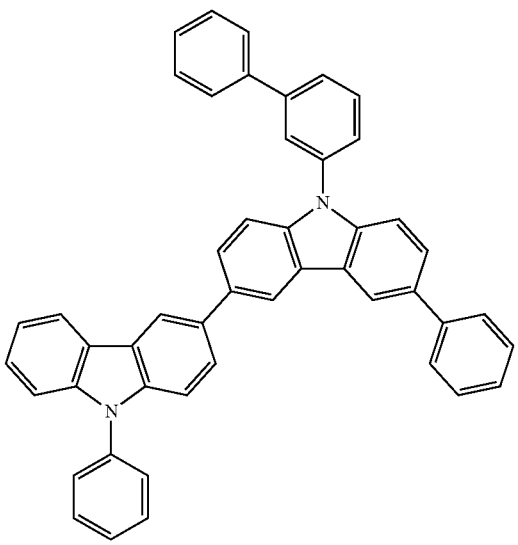
[D-130]
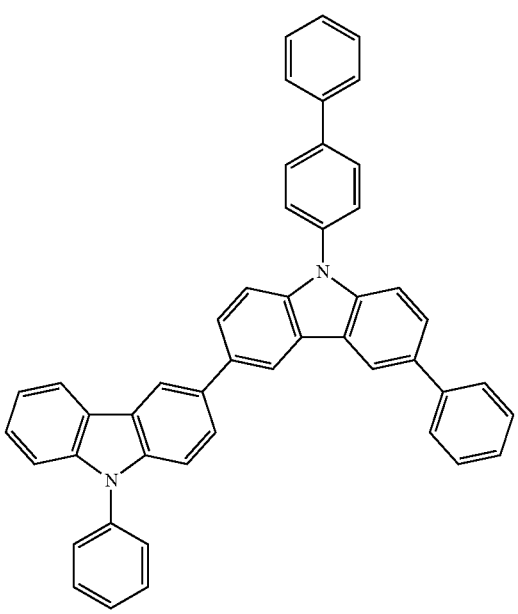

[D-131]
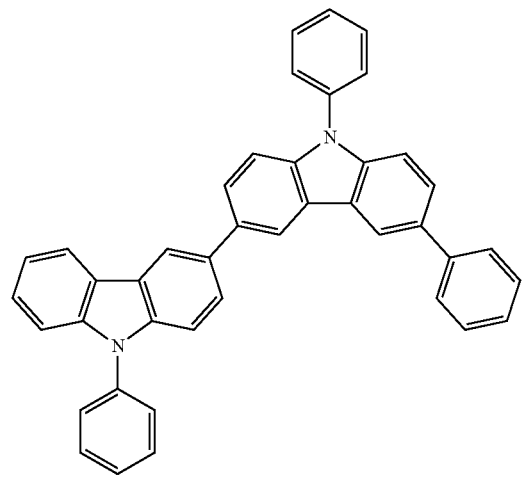
[D-132]
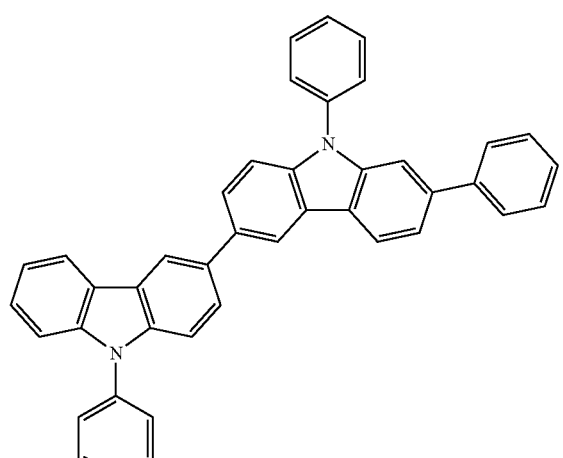
[D-133]
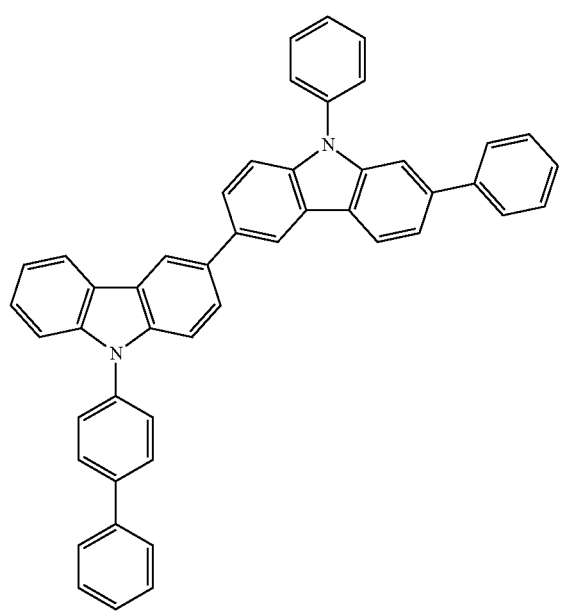
[D-134]
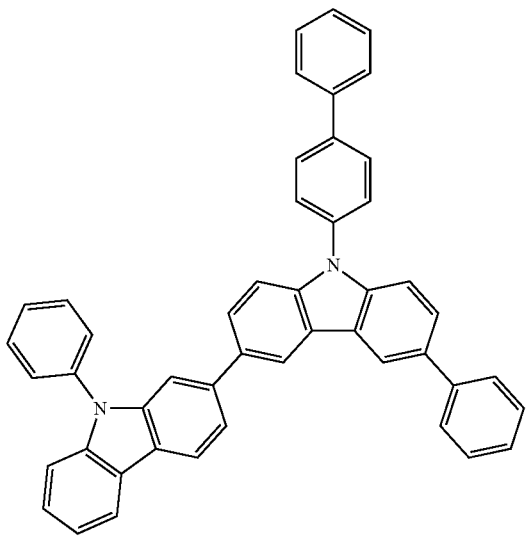
[D-135]
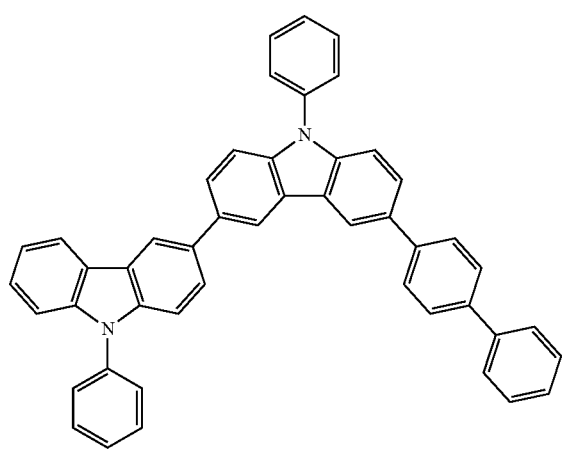
[D-136]

[D-137]

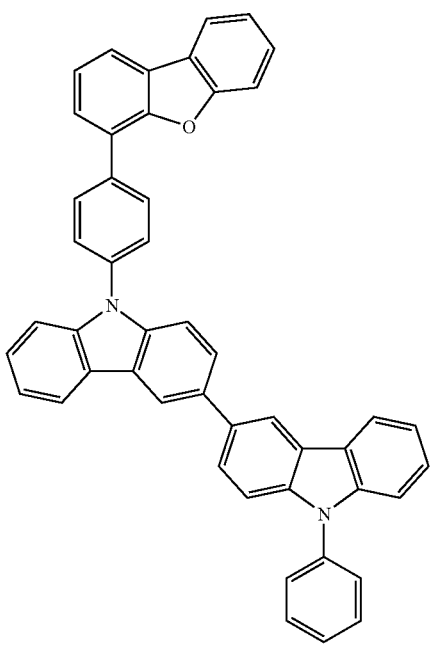

[D-138]

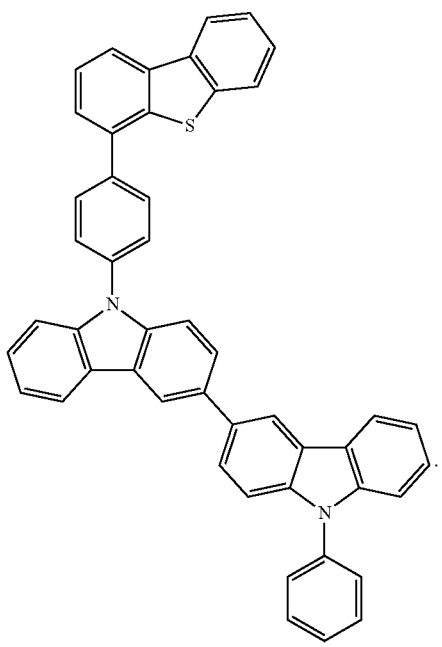

The first host and the second host may be applied in a form of a composition.

The phosphorescent dopant may be a red or green phosphorescent dopant. In an implementation, the phosphorescent dopant may be an organometallic compound represented by Chemical Formula 3.

[Chemical Formula 3]

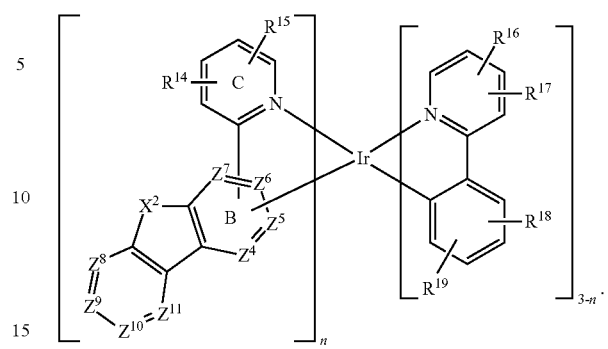

In Chemical Formula 3, $Z^4$ to $Z^{11}$ may each independently be N, C or $CR^c$, ring C may be bound to ring B through a C—C bond, iridium may be bound to ring B through an Ir—C bond, $X^2$ may be O or S, $R^c$ (e.g., of $CR^c$ in $Z^4$ to $Z^{11}$, above) and $R^{14}$ to $R^{19}$ may each independently be hydrogen, deuterium, a halogen, germanium group, a cyano group, a substituted or unsubstituted silyl group, a substituted or unsubstituted C1 to C10 alkyl group, a substituted or unsubstituted C3 to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n may be an integer ranging from 1 to 3.

The composition including the first and second hosts may be combined with the phosphorescent dopant including a dibenzofuranyl group, a dibenzothiophenyl group, or a derivative of the dibenzofuranyl group and the dibenzothiophenyl group including at least one N in a hexagonal ring of the dibenzofuranyl group and the dibenzothiophenyl group to secure a combination/matching advantage of packing of host and dopant materials, an energy transport, and the like and thus obtain characteristics of a low driving voltage, a long life-span, and high efficiency.

In an implementation, one of $Z^4$ to $Z^{11}$ of Chemical Formula 3 may be N. In an implementation, two, three, or four of $Z^4$ to $Z^{11}$ of Chemical Formula 3 may be N.

The phosphorescent dopant may be, e.g., represented by one of Chemical Formula 3-1 to Chemical Formula 3-6.

[Chemical Formula 3-1]

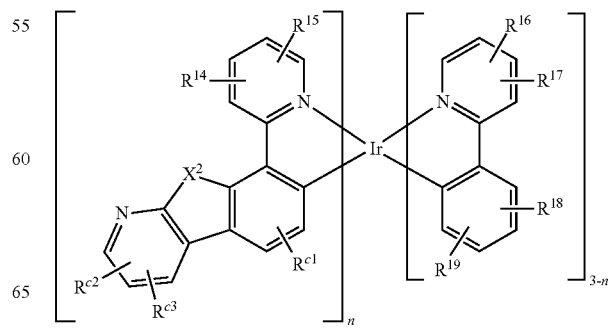

[Chemical Formula 3-2]

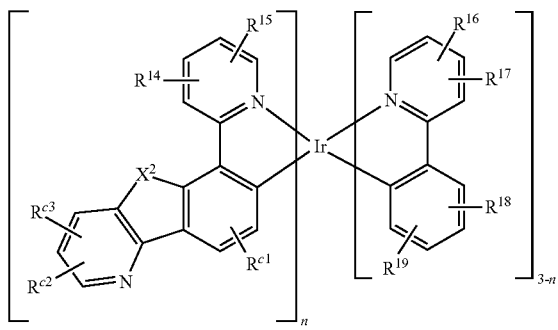

[Chemical Formula 3-3]

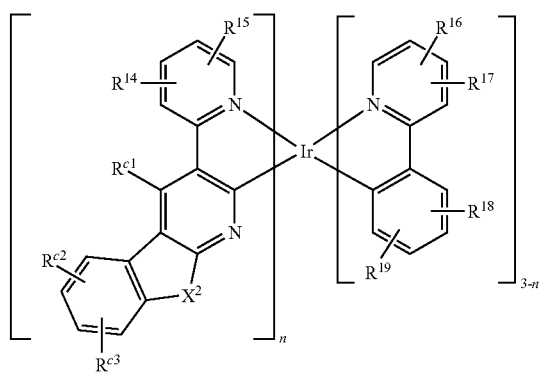

[Chemical Formula 3-4]

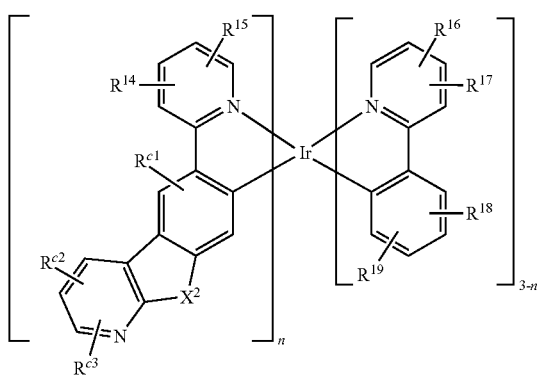

[Chemical Formula 3-5]

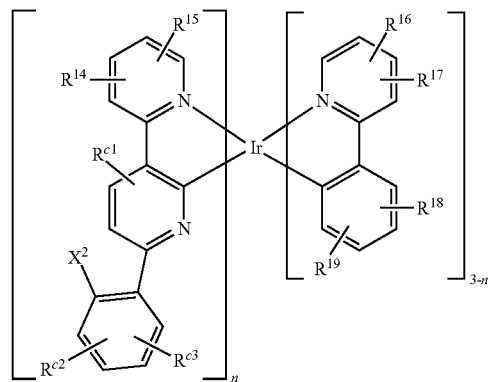

[Chemical Formula 3-6]

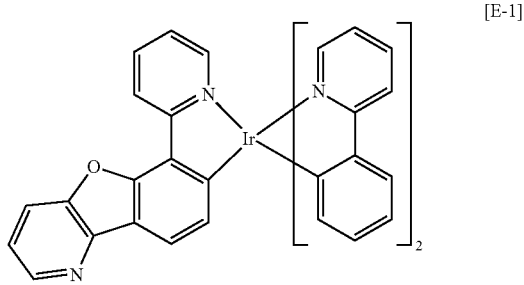

In Chemical Formula 3-1 to Chemical Formula 3-6, $X^2$, $R^{14}$ to $R^{19}$ and n may be the same as described above, and $R^{c1}$, $R^{c2}$, and $R^{c3}$ are the same as $R^c$.

In an implementation, $R^c$, $R^{c1}$, $R^{c2}$, $R^{c3}$, and $R^{14}$ to $R^{19}$ may each independently be hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C20 aryl group, for example $R^c$, $R^{c1}$, $R^{c2}$, $R^{c3}$, and $R^{14}$ to $R^{19}$ may independently be hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C12 aryl group. In an implementation, $R^c$, $R^{c1}$, $R^{c2}$, $R^{c3}$, and $R^{14}$ to $R^{19}$ may each independently be hydrogen, deuterium, a halogen, a silyl group that is substituted or unsubstituted with deuterium or a halogen, a methyl group that is substituted or unsubstituted with deuterium or a halogen, an isopropyl group that is substituted or unsubstituted with deuterium or a halogen, a tert-butyl group that is substituted or unsubstituted with deuterium or a halogen, or a silyl group that is substituted or unsubstituted with a C1 to C4 alkyl group.

In an implementation, the phosphorescent dopant may be, e.g., selected from compounds of Group 3.

[Group 3]

[E-1]

[E-2]
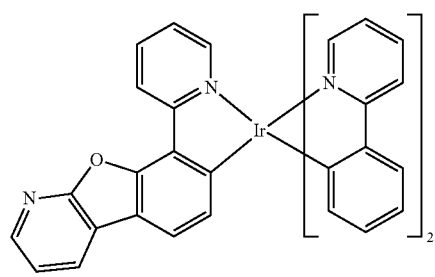
[E-3]
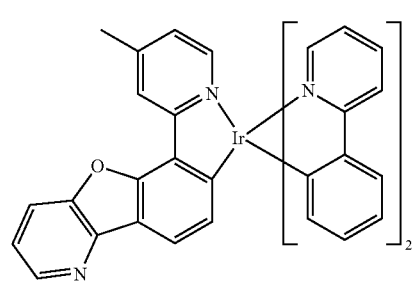
[E-4]
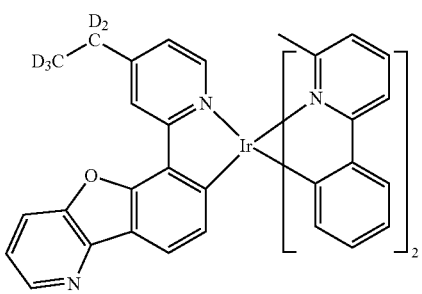
[E-5]
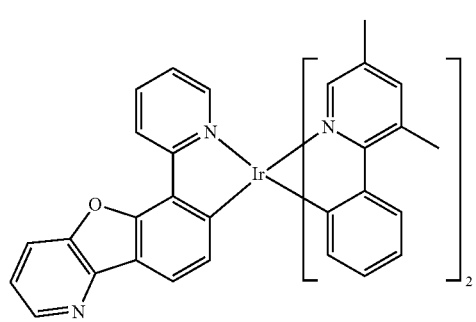
[E-6]
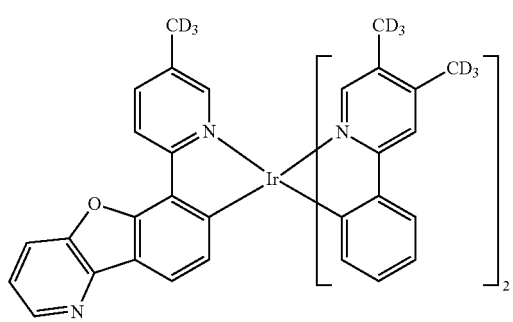
[E-7]
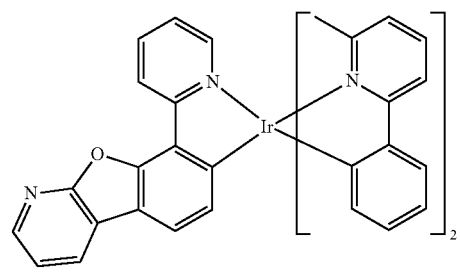
[E-8]
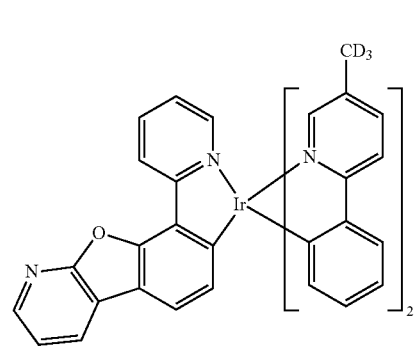
[E-9]
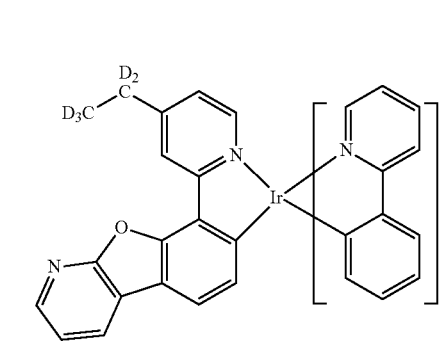
[E-10]
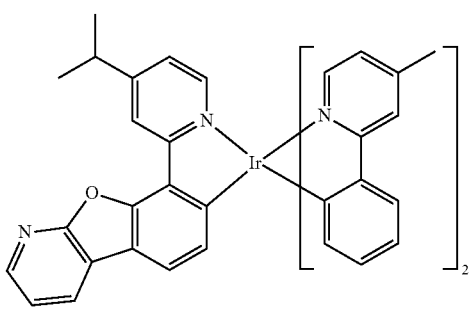
[E-11]
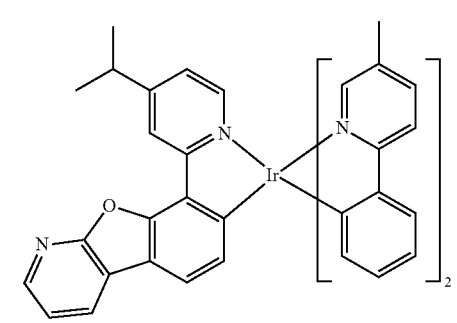

-continued
[E-12] 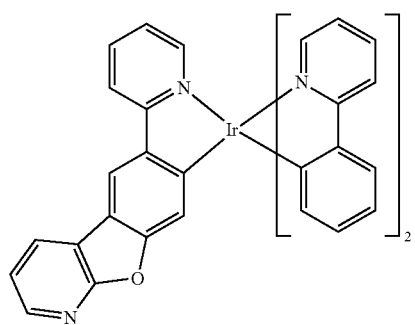
[E-13] 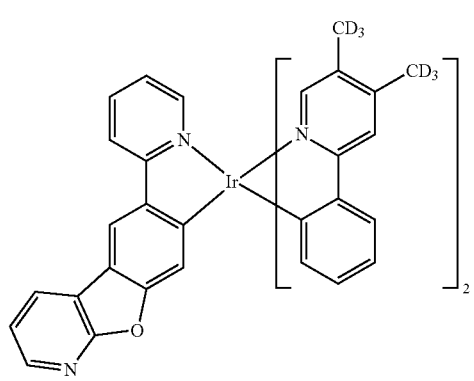
[E-14] 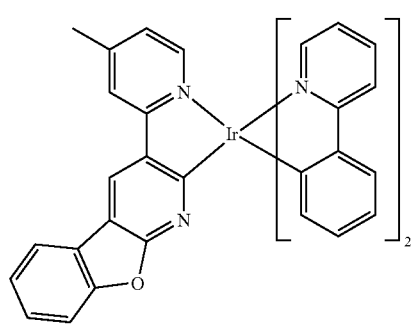
[E-15] 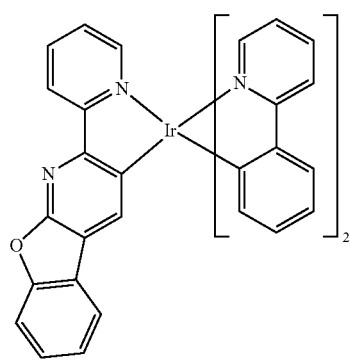
-continued
[E-16] 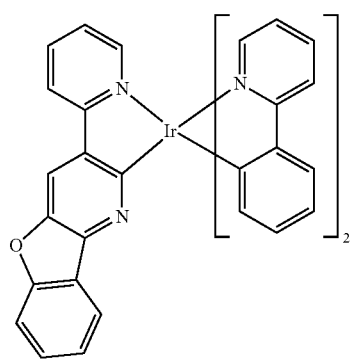
[E-17] 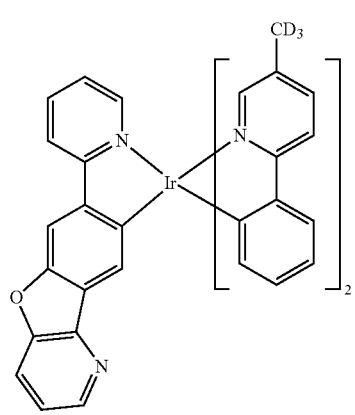
[E-18] 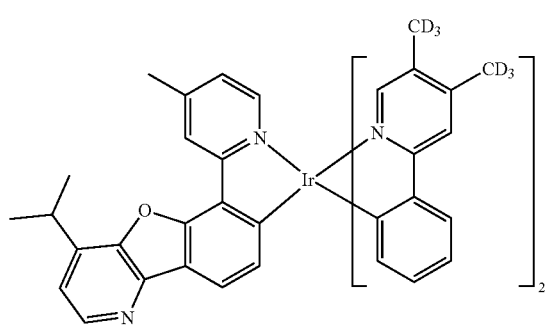
[E-19] 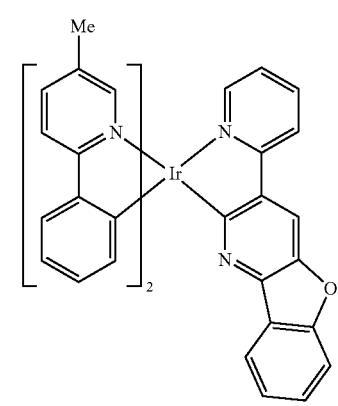

[E-20] 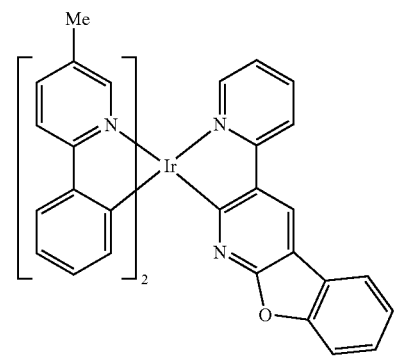
[E-21] 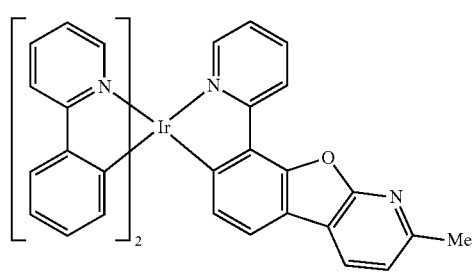
[E-22] 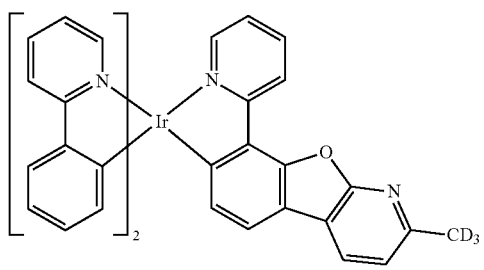
[E-23] 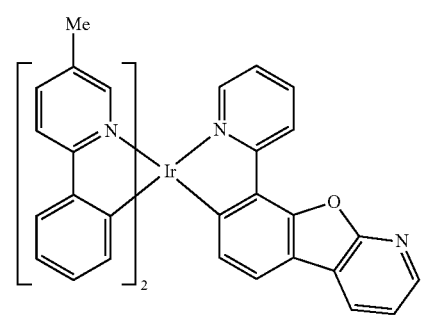
[E-24] 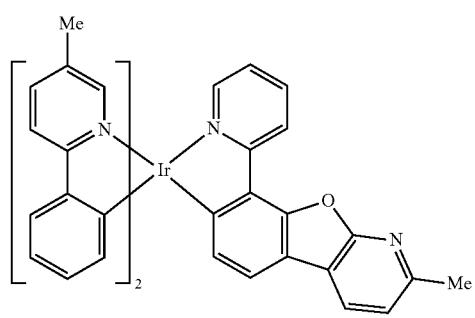
[E-25] 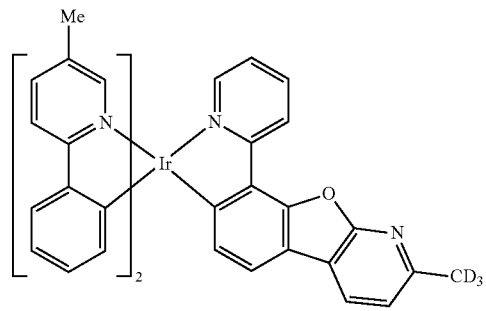
[E-26] 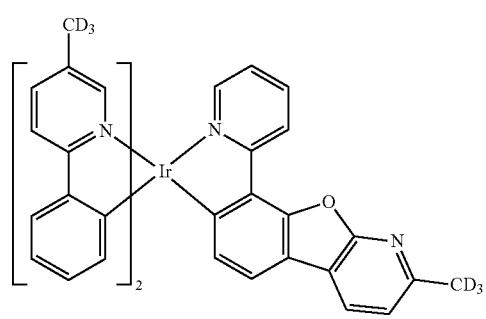
[E-27] 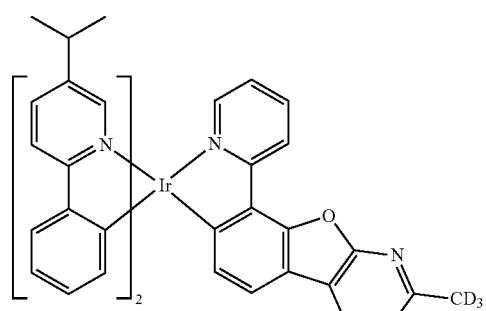
[E-28] 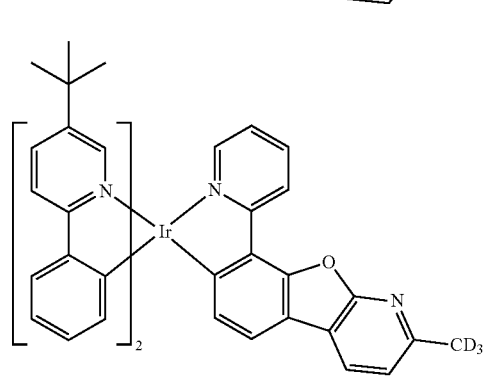
[E-29] 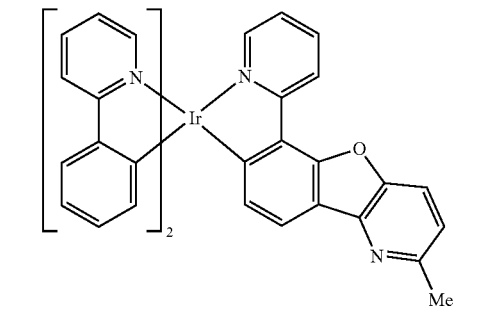

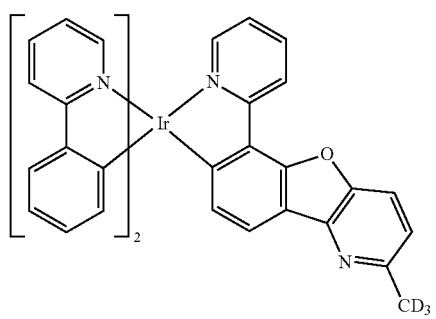 [E-30]
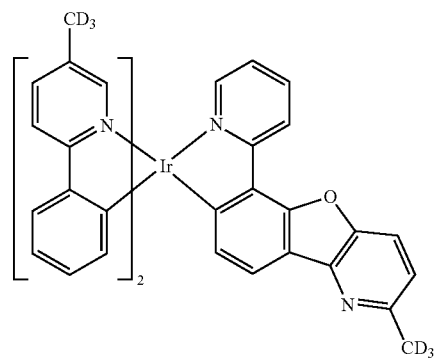 [E-34]
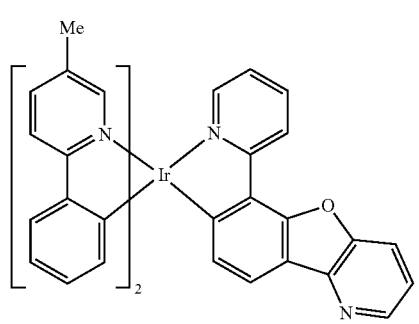 [E-31]
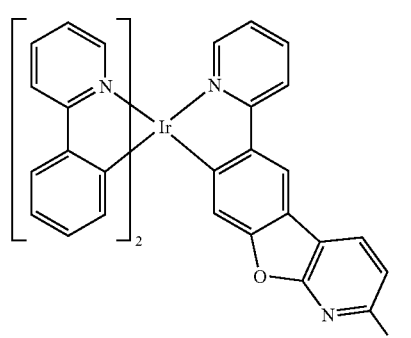 [E-35]
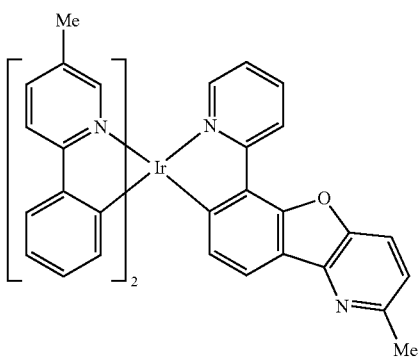 [E-32]
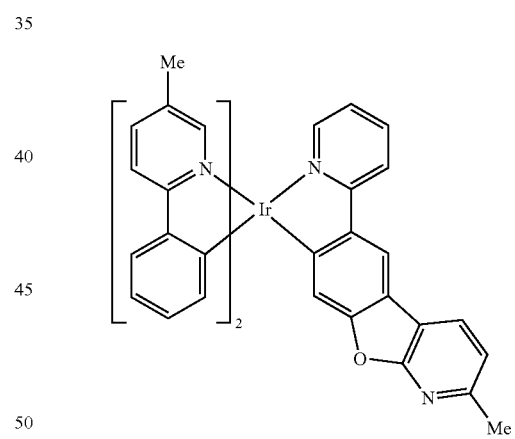 [E-36]
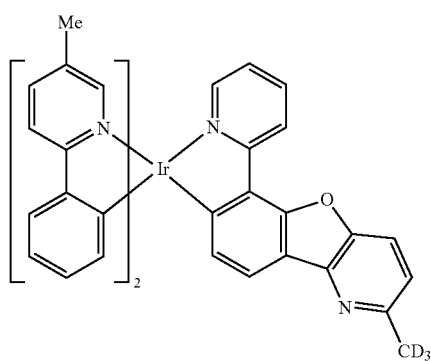 [E-33]
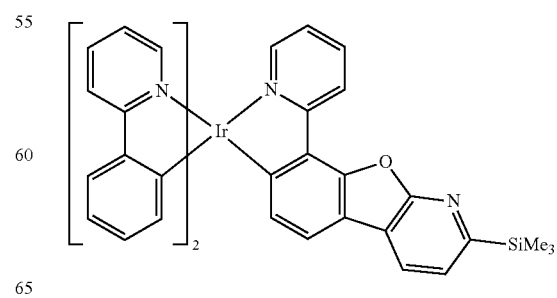 [E-37]

-continued

[E-38]

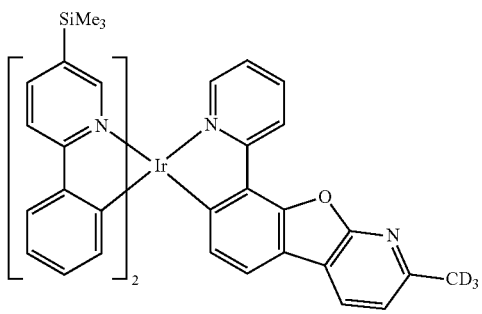

[E-39]

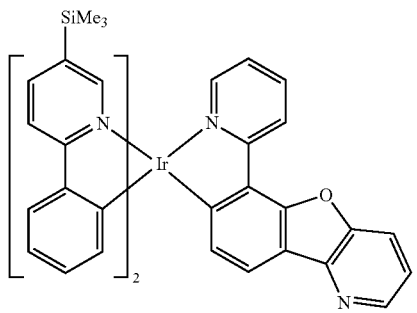

[E-40]

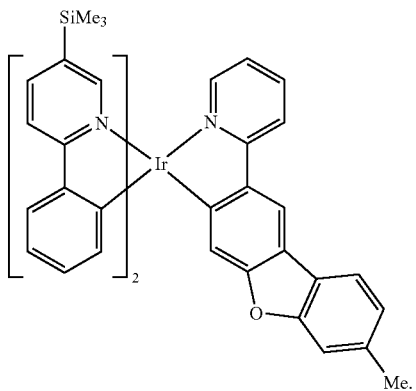

In an implementation, a composition including a first host represented by Chemical Formula 1-3, a second host represented by Chemical Formula 2A, and a phosphorescent dopant represented by Chemical Formula 3-1 may be applied to the light emitting layer.

In an implementation, Chemical Formula 1-3 may be, e.g., Chemical Formula 1-3a.

In an implementation, $Z^1$ to $Z^3$ of Chemical Formula 1-3a may be all N, $R^1$ may be a substituted or unsubstituted C6 to C20 aryl group, a substituted or unsubstituted dibenzofuranyl group, or a substituted or unsubstituted dibenzothiophenyl group, and $L^1$ may be a single bond or a meta-phenylene group.

In an implementation, $Y^1$ and $Y^2$ of Chemical Formula 2A may each independently be a substituted or unsubstituted phenyl group, a substituted or unsubstituted meta-biphenyl group, a substituted or unsubstituted para-biphenyl group, a substituted or unsubstituted carbazolyl group, a substituted or unsubstituted dibenzofuranyl group, or a substituted or unsubstituted dibenzothiophenyl group, and $L^3$ and $L^4$ may each independently be a single bond or a substituted or unsubstituted C6 to C20 arylene group.

In an implementation, $R^{c1}$, $R^{c2}$, $R^{c3}$ and $R^{14}$ to $R^{19}$ of Chemical Formula 3-1 may each independently be hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C12 aryl group.

In an implementation, the first host and the second host may be included in a weight ratio of 1:9 to 6:4, 2:8 to 6:4, 3:7 to 6:4. In an implementation, the first host and the second host may be included in a weight ratio of 1:9 to 5:5, 2:8 to 5:5, 3:7 to 5:5. In an implementation, the first host and the second host may be included in a weight ratio of 3:7 to 5:5.

In an implementation, the phosphorescent dopant may be included in an amount of about 0.1 wt % to 15 wt %, e.g., 1 wt % to 15 wt % or 5 wt % to 15 wt % based on 100 wt % of the composition of the first host and second host. For example, the first host and the second host may be included in a weight ratio of 3:7 and the phosphorescent dopant may be included in an amount of 5 wt % to 15 wt % based on 100 wt % of the composition of the first host and second host.

The composition of the first host and the second host according to an embodiment may include a suitable additional phosphorescent dopant in addition to the phosphorescent dopant described above.

The additional phosphorescent dopant may be mixed an organic metal compound including one of Ir, Pt, Os, Ti, Or, Hf, Eu, Tb, Tm, Fe, Co, Ni, Ru, Rh, Pd, or a combination thereof.

In an implementation, a dopant that exhibits excellent effect by combining the composition of the first host and the second host according to an embodiment may be a phosphorescent dopant represented by Chemical Formula 3.

In an implementation, one example of the additional phosphorescent dopant may be an organic metal compound represented by Chemical Formula 401.

<Chemical Formula 401>

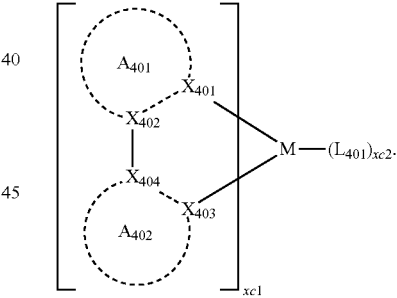

In Chemical Formula 401, M may be selected from Ir, Pt, Os, Ti, Or, Hf, Eu, Tb, and Tm; $X_{401}$ to $X_{404}$ may each independently be nitrogen or carbon; ring $A_{401}$ and $A_{402}$ rings may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; wherein "substituted" refers to replacement of at least one hydrogen of a substituent or a compound by deuterium, a halogen, a hydroxyl group, a cyano group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heterocyclic group, a C1 to C20 alkoxy group, a C1 to C10 trifluoroalkyl group, or a combination thereof; $L_{401}$ may be an organic ligand; xc1 may be 1, 2, or 3; and xc2 may be 0, 1, 2, or 3.

$L_{401}$ may be a suitable monovalent, divalent, or trivalent organic ligand. For example, $L_{401}$ may be selected from a halogen ligand (for example, Cl, F), diketone ligand (for example, acetylacetonate, 1,3-diphenyl-1,3-propanedionate, 2,2,6,6-tetramethyl-3,5-heptanedionate, or hexafluoroacetonate), carboxylic acid ligand (for example, picolinate, dimethyl-3-pyrazolecarboxylate, benzoate), a carbon monooxide ligand, an isonitrile ligand, a cyano ligand, and a phosphorus ligand (for example, phosphine, phosphite).

$Q_{401}$ to $Q_{407}$, $Q_{411}$ to $Q_{417}$, and $Q_{421}$ to $Q_{427}$ may each independently be selected from hydrogen, a C1 to C60 alkyl group, a C2 to C60 alkenyl group, a C6 to C60 aryl group, and a C2 to C60 heteroaryl group.

When $A_{401}$ of Chemical Formula 401 has two or more substituents, they may be combined with two or more substituents of $A_{401}$ to form a saturated or unsaturated ring.

When $A_{402}$ of Chemical Formula 401 has two or more substituents, they may be combined with two or more substituents of $A_{402}$ to form a saturated or unsaturated ring.

When xc1 of Chemical Formula 401 is two or more, a plurality of ligands

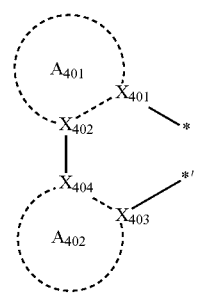

of Chemical Formula 401 may be the same or different.

When xc1 of Chemical Formula 401 is two or more, $A_{401}$ and $A_{402}$ may be independently linked with $A_{401}$ and $A_{402}$ of adjacent other ligand directly or by a linking group (for example, C1 to C5 alkylene group, —N(R')— (wherein, R' is a C1 to C10 alkyl group or a C6 to C20 aryl group), or —C(=O)—).

In an implementation, the additional phosphorescent dopant may be selected from Compounds PD70 to PD75.

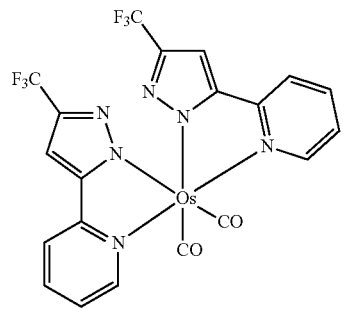

PD70

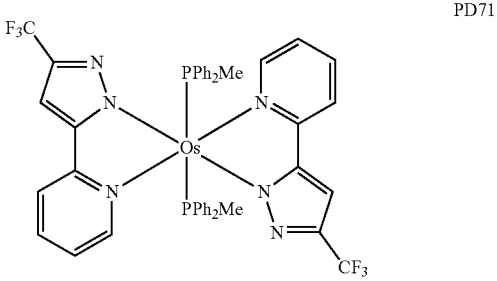

PD71

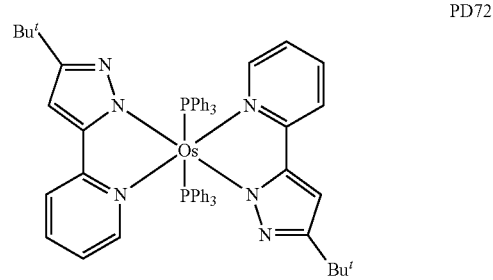

PD72

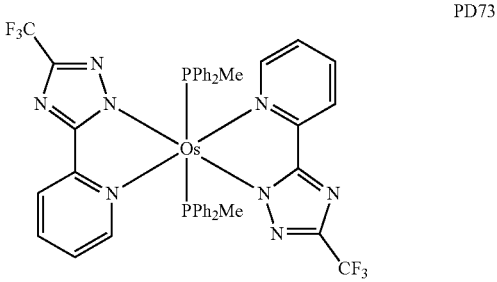

PD73

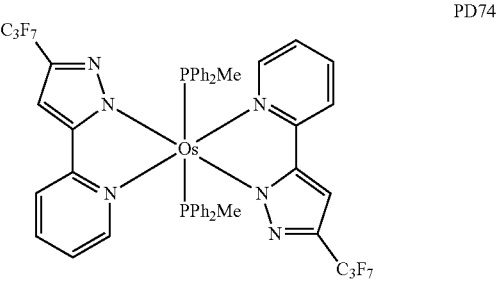

PD74

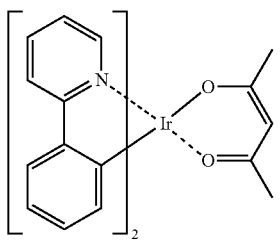

PD75

The organic light emitting diode may be applied to an organic light emitting diode (OLED) display.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co. Ltd. or TCI Inc. or were synthesized by suitable methods.

Compounds were synthesized through the following steps.

(Preparation of First Host)

Synthesis Example 1: Synthesis of Compound B-1

[Reaction Scheme 1]

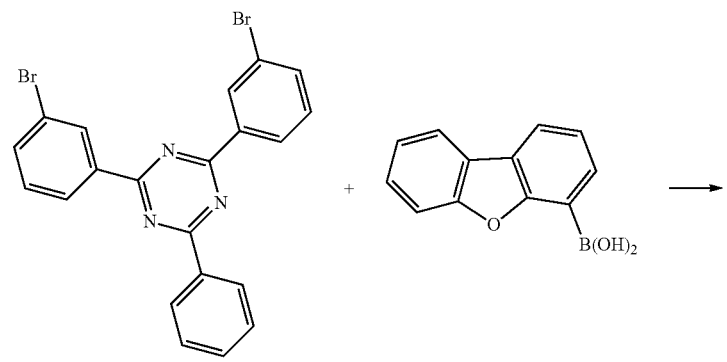

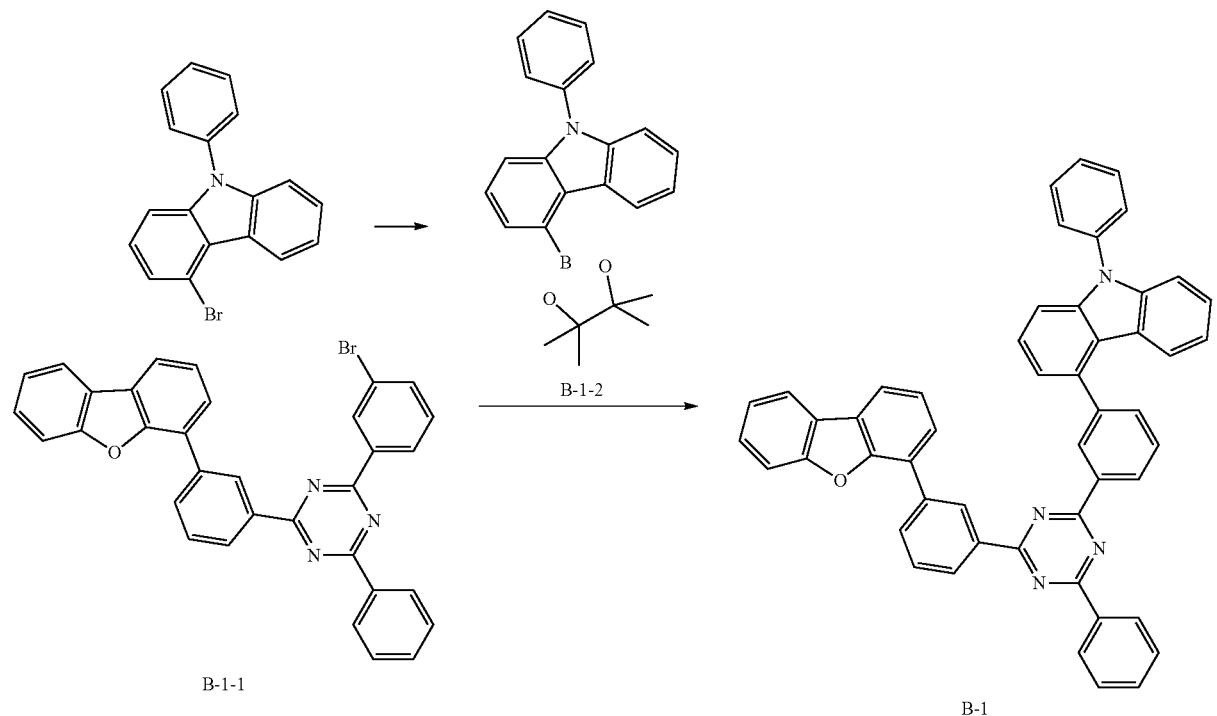

a) Synthesis of Intermediate B-1-1

30.0 g (64.2 mmol) of 2,4-bis(3-bromophenyl)-6-phenyl-1,3,5-triazine were added to 100 mL of tetrahydrofuran, 100 mL of toluene, and 100 mL of distilled water in a 500 mL round-bottomed flask, 1.0 equivalent of dibenzofuran-4-boronic acid, 0.03 equivalent of tetrakis(triphenylphosphine) palladium, and 2 equivalents of potassium carbonate were added thereto, and the mixture was heated and refluxed under a nitrogen atmosphere. After 6 hours, the reaction solution was cooled down, an aqueous layer was removed therefrom, and an organic layer therein was dried under a reduced pressure. The obtained solid was washed with water and hexane, the solid was recrystallized with 300 mL of toluene to obtain 21.4 g (a yield of 60%) of Intermediate B-1-1.

b) Synthesis of Intermediate B-1-2

15 g (46.55 mmol) of 4-bromo-9-phenylcarbazole (CAS: 1097884-37-1) was added to 200 mL of toluene in a 500 mL round-bottomed flask, 0.05 equivalent of dichlorodiphenylphosphinoferrocene palladium, 1.2 equivalent of bis(pinacolato) diboron, and 2 equivalents of potassium acetate were added thereto, and the mixture was heated and refluxed under a nitrogen atmosphere for 18 hours. The reaction solution was cooled down and added to 1 L of water in a dropwise fashion. A solid obtained therefrom was dissolved in boiling toluene to then treat with activated carbon and was then filtered with silica gel, and a filtrate therefrom was concentrated, precipitating a solid in the concentrated filtrate. The concentrated filtrate (including the solid therein) was stirred with a small amount of hexane and filtered to obtain Intermediate B-1-2 at a yield of 80%.

c) Synthesis of Compound B-1

20 g (36.1 mmol) of Intermediate B-1-1 was added to 100 mL of tetrahydrofuran and 50 mL of distilled water in a 500 mL round-bottomed flask, 1.1 equivalent of Intermediate B-1-2, 0.03 equivalent of tetrakis(triphenylphosphine) palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 24 g of Compound B-1.

LC/MS calculated for: $C_{51}H_{32}N_4O$ Exact Mass: 716.2576 found for: 717.26 [M+H].

Synthesis Example 2: Synthesis of Compound B-13

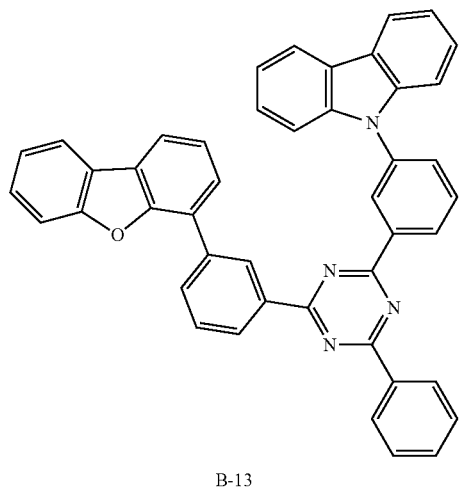

B-13

1 equivalent of Intermediate B-1-1, 1 equivalent of carbazole, 2 eq of sodium t-butoxide, and 0.05 eq of $Pd_2(dba)_3$ were suspended to be 0.2 M in xylene, 0.15 eq of tri-tertiarybutylphosphine was added thereto, and the mixture was refluxed and stirred for 18 hours. Methanol was added thereto in an amount of 1.5 times that of the xylene solvent, the mixture was stirred, and a solid obtained therefrom was filtered and washed with 300 mL of water. The solid was recrystallized by using monochlorobenzene to obtain Compound B-13 at a yield of 85%.

LC/MS calculated for: $C_{45}H_{28}N_4O$ Exact Mass: 640.2263 found for: 641.23 [M+H].

Synthesis Example 3: Synthesis of Compound B-17

[Reaction Scheme 3]

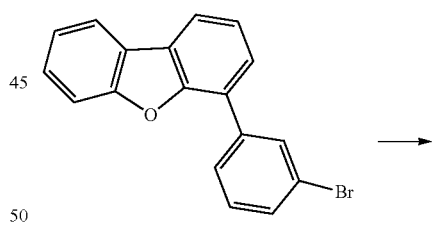

[Reaction Scheme 2]

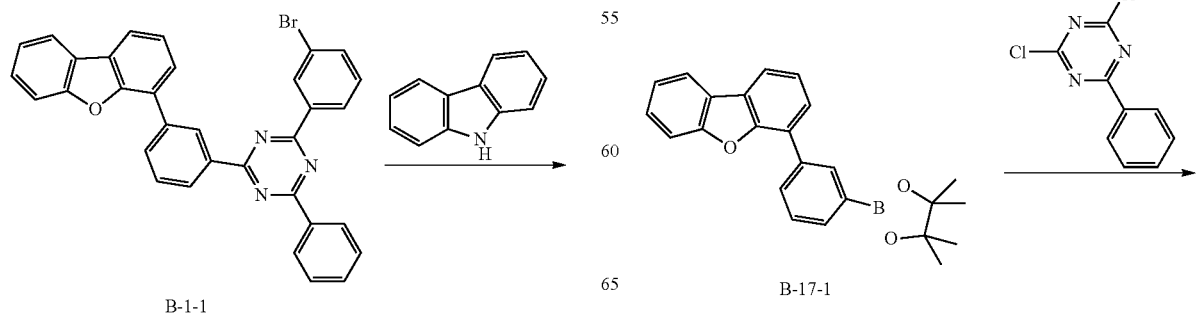

B-1-1

B-17-1

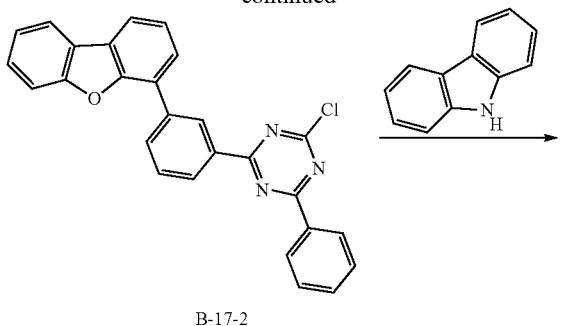

B-17-2

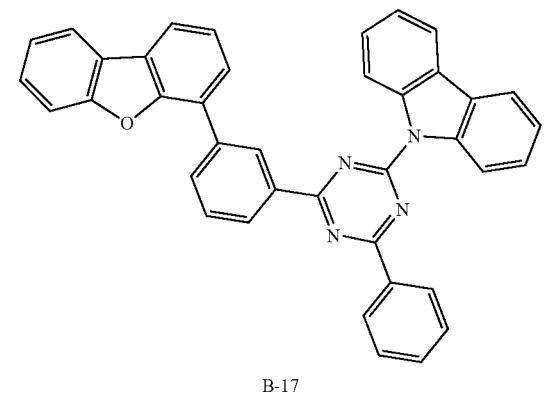

B-17 a) Synthesis of Intermediate B-17-1

15 g (46.4 mmol) of 4-(3-bromophenyl)-dibenzofuran (CAS: 887944-90-3) was added to 200 mL of toluene in a 500 mL round-bottomed flask, 0.05 equivalent of dichlorodiphenylphosphinoferrocene palladium, 1.2 equivalent of bis(pinacolato) diboron, and 2 equivalents of potassium acetate were added thereto, and the mixture was heated and refluxed under a nitrogen atmosphere for 18 hours. The solution was washed with water through an extraction, an organic layer therefrom was treated with activated carbon and filtered in silica gel, and a filtrate was concentrated, precipitating a solid in the concentrated filtrate. The concentrated filtrate (including the solid therein) was stirred with an amount of hexane and filtered to obtain Intermediate B-17-1 at a yield of 85%.

b) Synthesis of Intermediate B-17-2

9.04 g (40 mmol) of 2,4-dichloro-6-phenyltriazine was added to 60 mL of tetrahydrofuran, 60 mL of toluene, and 60 mL of distilled water in a 500 mL round-bottomed flask, 0.9 equivalent of Intermediate B-17-1, 0.03 equivalent of tetrakis(triphenylphosphine) palladium, and 2 equivalents of potassium carbonate were added thereto, and the mixture was heated and refluxed under a nitrogen atmosphere. After 6 hours, the reaction solution was cooled down, and after removing an aqueous layer therefrom, an organic layer therein was dried under a reduced pressure. A solid therefrom was washed with water and hexane and then, recrystallized with 300 mL of toluene to obtain Intermediate B-17-2 at a yield of 40%.

c) Synthesis of Compound B-17

1 equivalent of Intermediate B-17-2, 1.1 equivalent of carbazole, 2 eq of sodium t-butoxide, and 0.05 eq of $Pd_2(dba)_3$ were suspended to be 0.2 M in xylene, 0.15 eq of tri-tertiarybutylphosphine was added thereto, and the mixture was refluxed and stirred for 18 hours. Methanol was added thereto in an amount of 1.5 times that of the xylene solvent, and a solid therein was filtered and washed with 300 mL of water. The solid was recrystallized by using monochlorobenzene to obtain Compound B-17 at a yield of 80%.

LC/MS calculated for: $C_{39}H_{24}N_4O$ Exact Mass: 564.1950 found for: 565.21 [M+H].

Synthesis Example 4: Synthesis of Compound C-1

[Reaction Scheme 4]

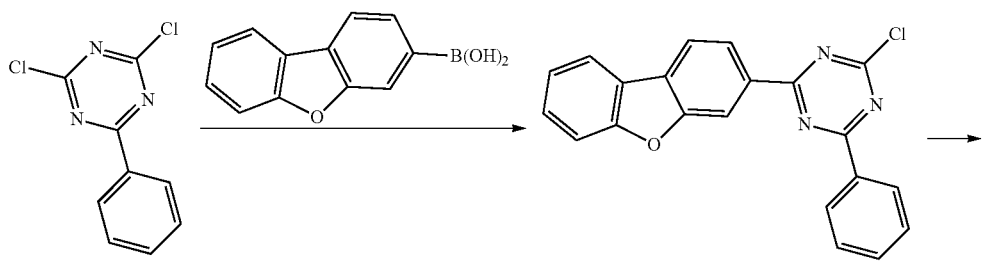

C-1-1

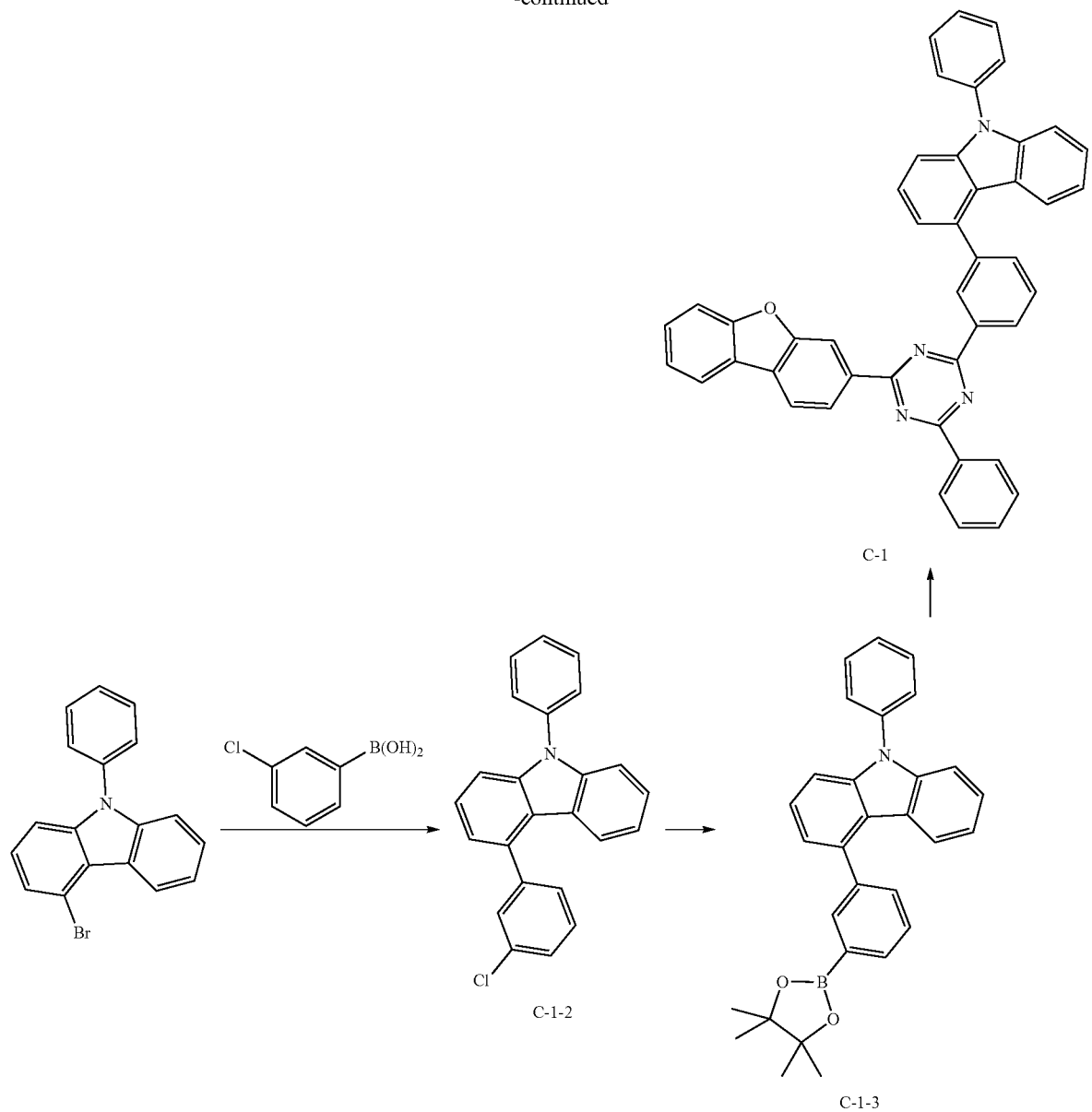

a) Synthesis of Intermediate C-1-1

22.6 g (100 mmol) of 2,4-dichloro-6-phenyltriazine was added to 100 mL of tetrahydrofuran, 100 mL of toluene, and 100 mL of distilled water in a 500 mL round-bottomed flask, 0.9 equivalent of dibenzofuran-3-boronic acid, 0.03 equivalent of tetrakis(triphenylphosphine) palladium, and 2 equivalents of potassium carbonate were added thereto, and the mixture was heated and refluxed under a nitrogen atmosphere. After 6 hours, the reaction solution was cooled down, and after removing an aqueous layer therefrom, an organic layer therein was dried under a reduced pressure. The obtained solid was washed with water and hexane and recrystallized with 200 mL of toluene to obtain 21.4 g of Intermediate C-1-1 at a yield of 60%.

b) Synthesis of Compound C-1-2

15 g (46.55 mmol) of 4-bromo-9-phenylcarbazole (CAS: 1097884-37-1) was added to 140 mL of tetrahydrofuran and 70 mL of distilled water in a 500 mL round-bottomed flask, 1.1 equivalent of 3-chlorophenyl boronic acid, 0.03 equivalents of tetrakis(triphenylphosphine) palladium, and 2 equivalents of potassium carbonate were added thereto, and the mixture was heated and refluxed under a nitrogen atmosphere. After 12 hours, the reaction solution was cooled down, an organic layer was extracted, and solvent was removed under a reduced pressure. A compound concentrated therefrom was treated through silica column chromatography to obtain Intermediate C-1-2 at a yield of 85%.

c) Synthesis of Intermediate C-1-3

12 g (33.9 mmol) of Intermediate C-1-2 was added to 150 mL of xylene in a 500 mL round-bottomed flask, 0.05 equivalent of dichlorodiphenylphosphinoferrocene palladium, 1.2 equivalent of bis(pinacolato) diboron, and 2 equivalents of potassium acetate were added thereto, and the mixture was heated and refluxed under a nitrogen atmosphere for 18 hours. The reaction solution was cooled down and then washed with water through an extraction, an organic layer therefrom was treated with activated carbon and filtered in silica gel, and a filtrate therefrom was concentrated, precipitating a solid in the concentrated filtrate. The concentrated filtrate (including the solid therein) was stirred with a small amount of hexane and filtered to obtain Intermediate C-1-3 at a yield of 75%.

d) Synthesis of Compound C-1

8 g (22.4 mmol) of Intermediate C-1-1 was added to 80 mL of tetrahydrofuran and 40 mL of distilled water in a 500 mL round-bottomed flask, 1.0 equivalent of Intermediate C-1-3, 0.03 equivalent of tetrakis(triphenylphosphine) palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 12 g of Compound C-1.

LC/MS calculated for: $C_{45}H_{28}N_4O$ Exact Mass: 640.2263 found for: 641.24.

Synthesis Example 5: Synthesis of Compound C-2

[Reaction Scheme 5]

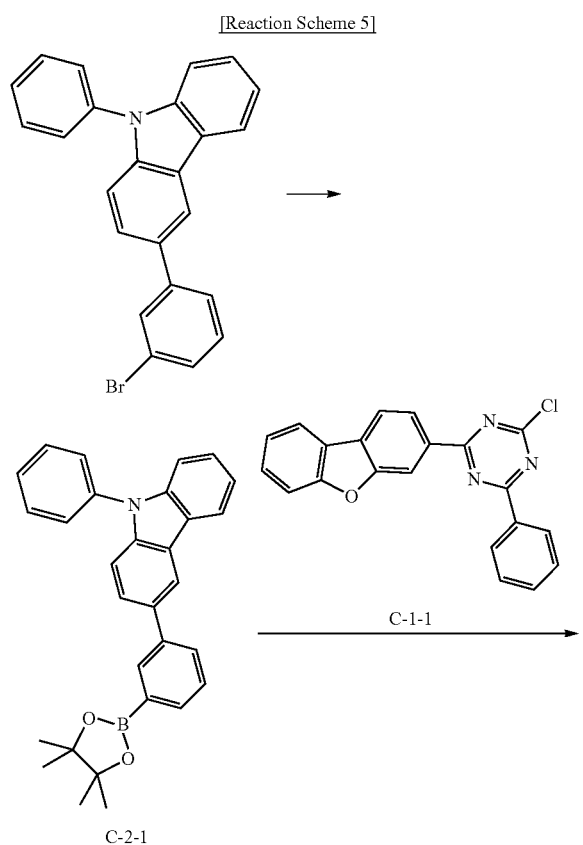

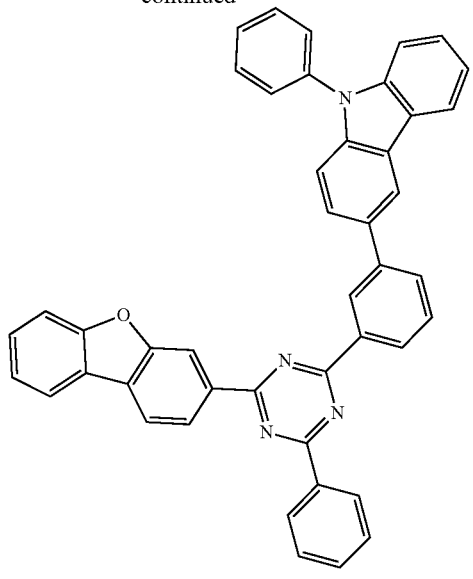

a) Synthesis of Intermediate C-2-1

15 g (46.4 mmol) of 3-(3-bromophenyl)-9-phenylcarbazole (CAS: 854952-59-3) was added to 200 mL of toluene in a 500 mL round-bottomed flask, 0.05 equivalent of dichlorodiphenylphosphinoferrocene palladium, 1.2 equivalent of bis(pinacolado) diboron, and 2 equivalents of potassium acetate were added thereto, and the mixture was heated and refluxed under a nitrogen atmosphere for 18 hours. The reaction solution was cooled down and added to 1 L of water in a dropwise fashion to collect a solid. The solid was dissolved in boiling toluene to then treat with activated carbon, was filtered in silica gel, and a filtrate therefrom was concentrated, precipitating a solid in the concentrated filtrate. The concentrated filtrate (including the solid therein) was stirred with a small amount of hexane and filtered to obtain Intermediate C-2-1 at a yield of 85%.

b) Synthesis of Compound C-2

8 g (22.4 mmol) of Intermediate C-1-1 according to Synthesis Example 4 was added to 80 mL of tetrahydrofuran and 40 mL of distilled water in a 500 mL round-bottomed flask, 1.0 equivalent of Intermediate C-2-1, 0.03 equivalent of tetrakis(triphenylphosphine) palladium, and 2 equivalents of potassium carbonate were added thereto, and the mixture was heated and refluxed under a nitrogen atmosphere. After 18 hours, the reaction solution was cooled down, and a solid precipitated therein was washed with 500 mL of water. The solid was recrystallized by using 500 mL of monochlorobenzene to obtain 13 g of Compound C-2.

LC/MS calculated for: $C_{45}H_{28}N_4O$ Exact Mass: 640.2263 found for: 641.24.

Synthesis Example 6: Synthesis of Compound C-12

[Reaction Scheme 6]

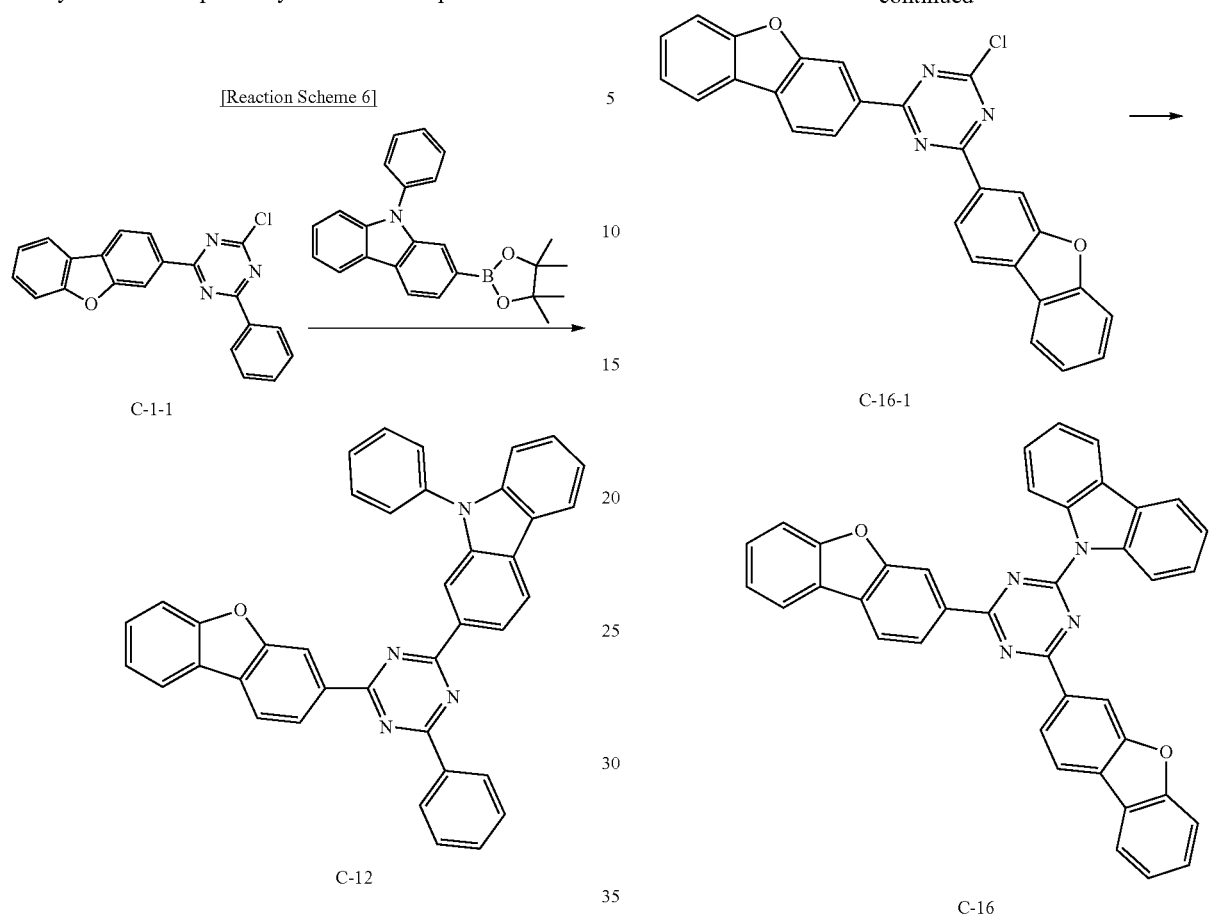

8 g (22.4 mmol) of Intermediate C-1-1 according to Synthesis Example 4 was added to 80 mL of tetrahydrofuran and 40 mL of distilled water in a 500 mL round-bottomed flask, 1.0 equivalent of 9-phenyl-2-(4,4,5,5-tetramethyl-1,3,2-dioxaborolan-2-yl)-carbazole (cas: 1246669-45-3), 0.03 equivalent of tetrakis(triphenylphosphine) palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 11 g of Compound C-12.

LC/MS calculated for: $C_{39}H_{24}N_4O$ Exact Mass: 564.1950 found for: 565.20.

Synthesis Example 7: Synthesis of Compound C-16

[Reaction Scheme 7]

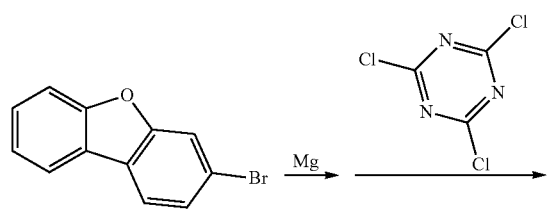

a) Synthesis of Intermediate C-16-1

Magnesium (7.86 g, 323 mmol) and iodine (1.64 g, 6.46 mmol) were added to 0.1 L of tetrahydrofuran (THF) under a nitrogen atmosphere, the mixture was stirred for 30 minutes, and 3-bromo dibenzofuran (80 g, 323 mmol) dissolved in 0.3 L of THF was slowly added thereto in a dropwise fashion at 0° C. over 30 minutes. The mixed solution was slowly added in a dropwise fashion to 29.5 g (160 mmol) of cyanuric chloride dissolved in 0.5 L of THF at 0° C. over 30 minutes. After heating a reaction up to ambient temperature, the mixture was stirred for 1 hour and additionally stirred for 12 hours under a reflux condition. After cooling down the reaction, water was slowly added thereto to finish the reaction, and an organic solvent therefrom was concentrated under a reduced pressure to obtain a solid. The solid was stirred with 200 mL of acetone and filtered to obtain Intermediate C-16-1 at a yield of 40%.

b) Synthesis of Compound C-16

Compound C-16 was synthesized according to the same method as Synthesis Example 2 by using Intermediate C-16-1.

LC/MS calculated for: $C_{39}H_{22}N_4O_2$ Exact Mass: 578.1743 found for 579.20.

Synthesis Example 8: Synthesis of Compound C-17

[Reaction Scheme 8]

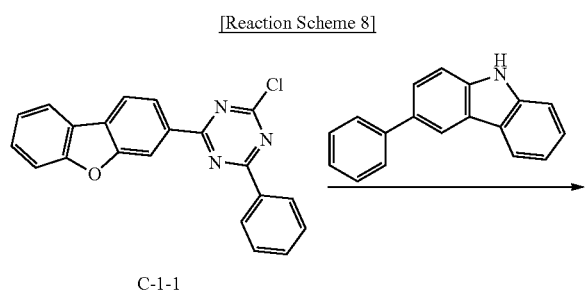

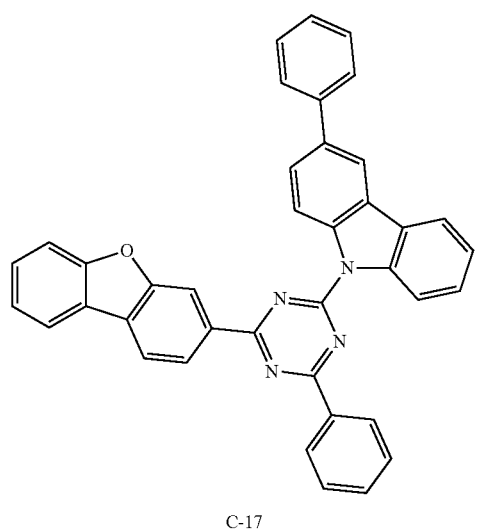

C-17

Compound C-17 was synthesized according to the same method as Synthesis Example 2 by using Intermediate C-1-1 and 3-phenyl-9H-carbazole respectively by 1 equivalent.

LC/MS calculated for: $C_{39}H_{24}N_4O$ Exact Mass: 564.1950 found for: 565.20.

Synthesis Example 9: Synthesis of Compound C-21

[Reaction Scheme 9]

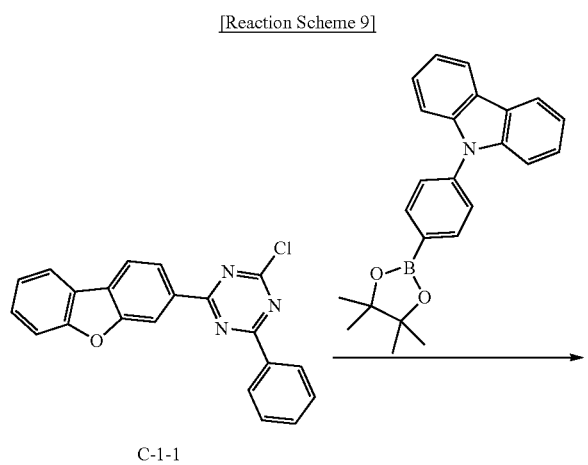

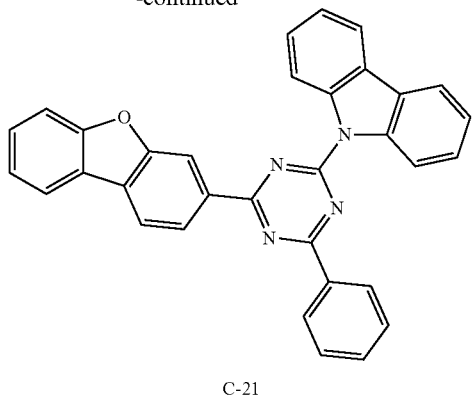

C-21

Compound C-21 was synthesized according to the same method as Synthesis Example 6 by using Intermediate C-1-1 and 9-(4-(4,4,5,5-tetramethyl-1,3,2-dioxaborolan-2-yl)-phenyl)-carbazole (Cas: 785051-54-9) respectively by 1.0 equivalent.

LC/MS calculated for: $C_{39}H_{24}N_4O$ Exact Mass: 564.1950 found for: 565.20.

Synthesis Example 10: Synthesis of Compound C-22

[Reaction Scheme 10]

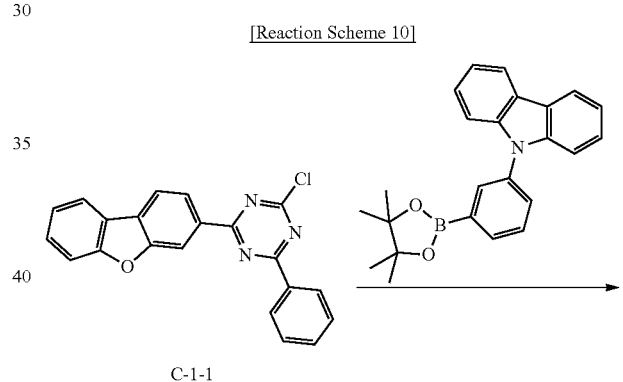

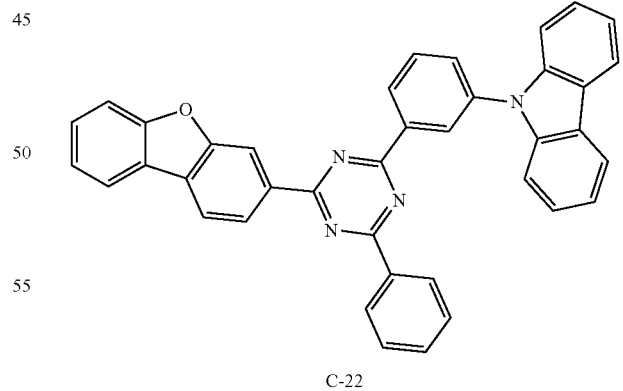

C-22

Compound C-22 was synthesized according to the same method as Synthesis Example 6 by using Intermediate C-1-1 and 9-(3-(4,4,5,5-tetramethyl-1,3,2-dioxaborolan-2-yl)-phenyl)-carbazole (CAS: 870119-58-7) respectively by 1.0 equivalent.

LC/MS calculated for: $C_{39}H_{24}N_4O$ Exact Mass: 564.1950 found for: 565.20.

Synthesis Example 11: Synthesis of Compound C-25

[Reaction Scheme 11]

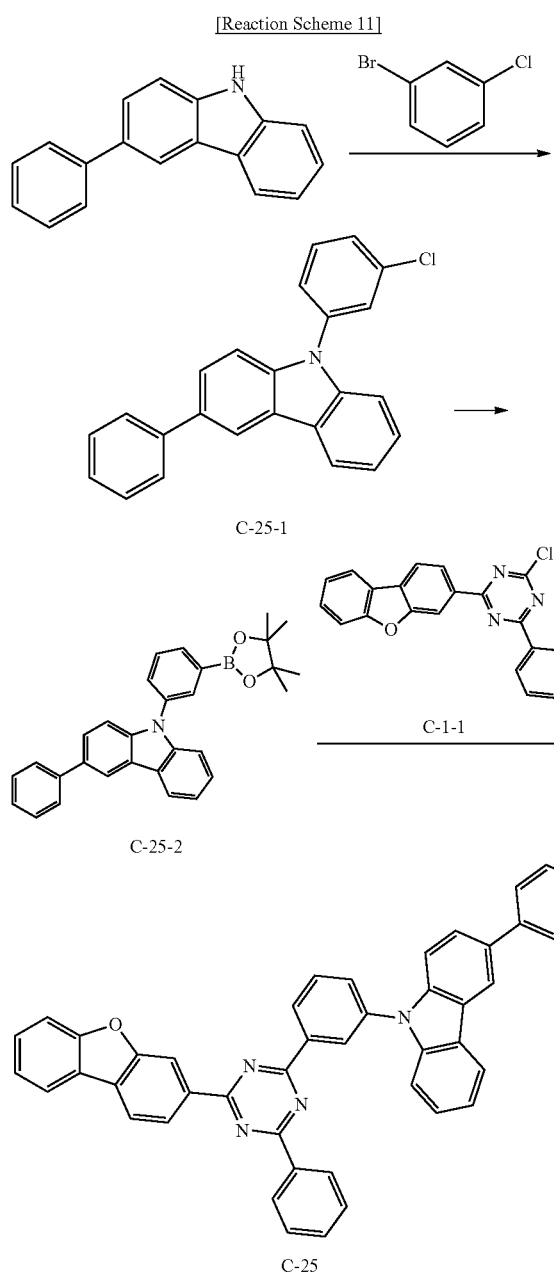

a) Synthesis of Intermediate C-25-1

Intermediate C-25-1 was synthesized according to the same method as Synthesis Example 2 by using 1 equivalent of 3-phenyl-9H-carbazole and 1.2 equivalents of 3-chloro-1-bromobenzene.

b) Synthesis of Intermediate C-25-2

Intermediate C-25-2 was synthesized according to the same method as a) of Synthesis Example 5 by using Intermediate C-25-1.

c) Synthesis of Compound C-25

Intermediate C-25 was synthesized according to the same method as a) of Synthesis Example 6 by using Intermediate C-25-2 and Intermediate C-1-1 respectively by 1.0 equivalent.

LC/MS calculated for: $C_{45}H_{28}N_4O$ Exact Mass: 640.2263 found for: 641.23.

Synthesis Example 12: Synthesis of Compound B-14

[Reaction Scheme 12]

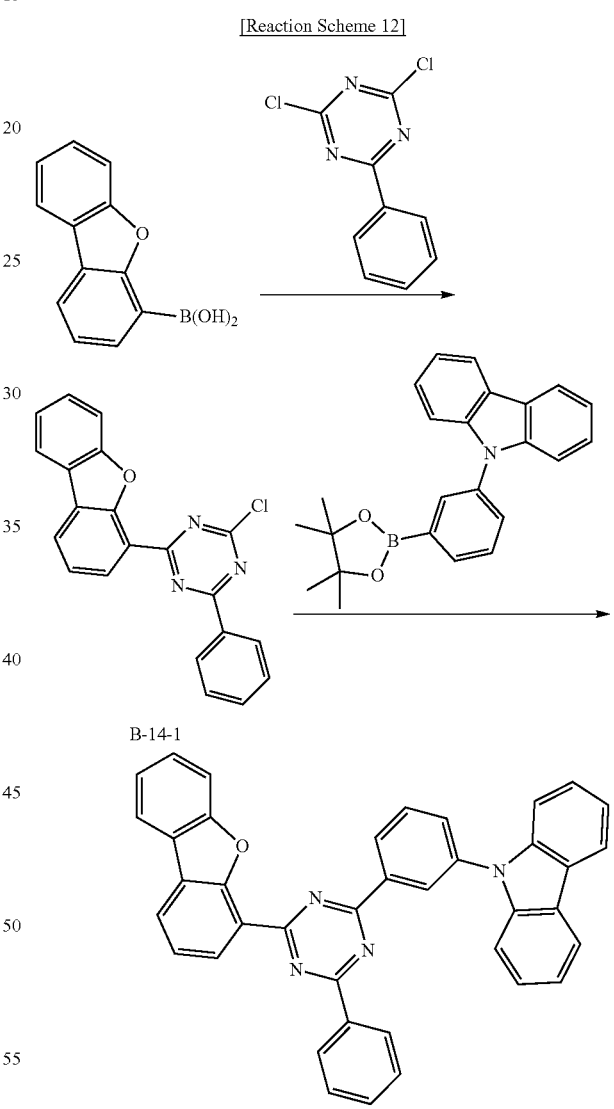

a) Synthesis of Intermediate B-14-1

Intermediate B-14-1 was synthesized according to the same method as a) of Synthesis Example 4 by using 1 equivalent of 2,4-dichloro-6-phenyltriazine and 0.9 equivalent of dibenzofuran-4-boronic acid.

b) Synthesis of Compound B-14

Intermediate B-14 was synthesized according to the same method as Synthesis Example 6 by using Intermediate B-14-1 and 9-(3-(4,4,5,5-tetramethyl-1,3,2-dioxaborolan-2-yl)-phenyl)-carbazole (CAS: 870119-58-7) by respectively 1.0 equivalent.

LC/MS calculated for: $C_{39}H_{24}N_4O$ Exact Mass: 564.1950 found for: 565.20.

Synthesis Example 13: Synthesis of Compound B-22 b) Synthesis of Compound B-22

Compound B-22 was synthesized according to the same method as Synthesis Example 6 by using Intermediate B-22-1 and 9-(3-(4,4,5,5-tetramethyl-1,3,2-dioxaborolan-2-yl)-phenyl)-carbazole (CAS: 870119-58-7) respectively by 1.0 equivalent.

LC/MS calculated for: $C_{39}H_{24}N_4O$ Exact Mass: 564.1950 found for: 565.21.

Synthesis Example 14: Synthesis of Compound B-25

[Reaction Scheme 13]

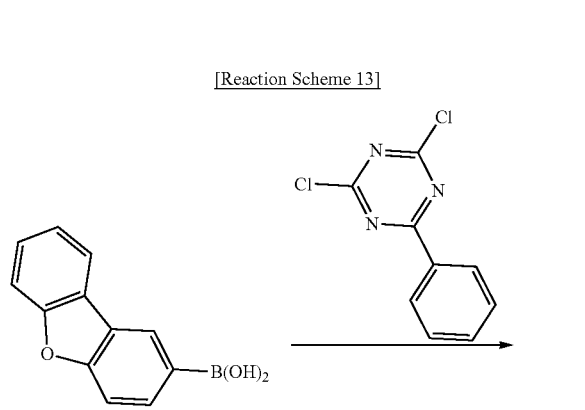

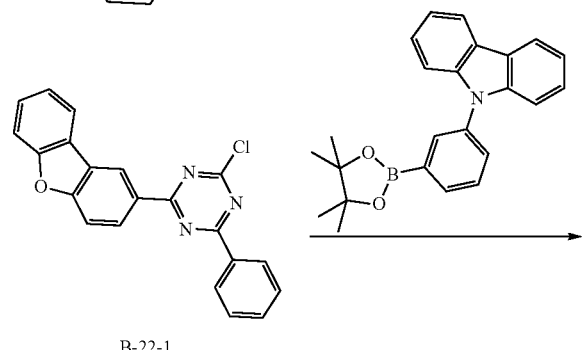

B-22-1

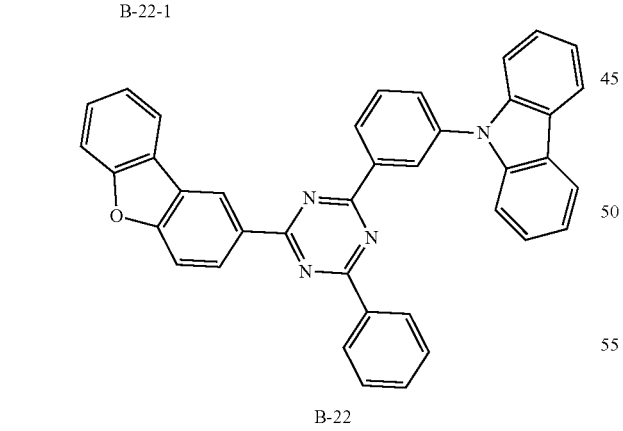

B-22

[Reaction Scheme 14]

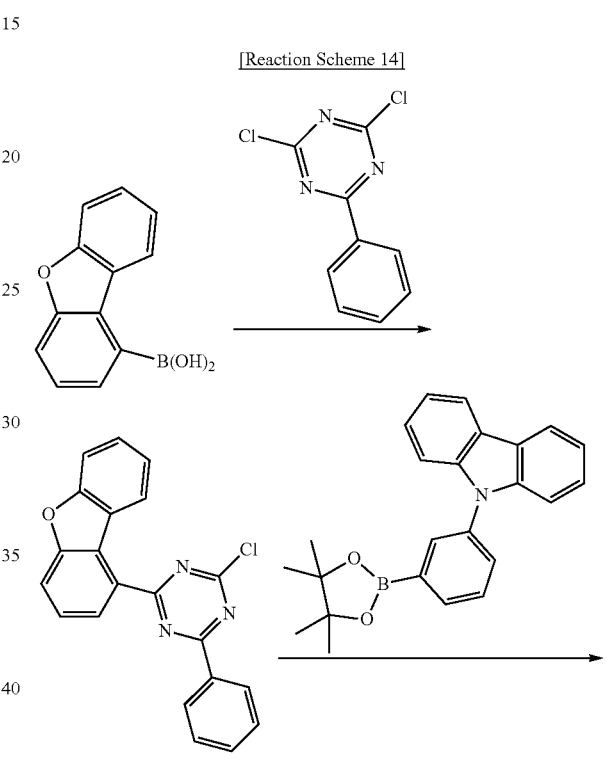

B-25-1

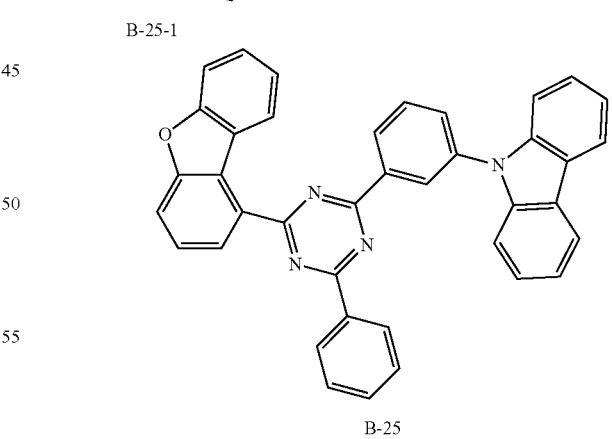

B-25 a) Synthesis of Intermediate B-22-1

Intermediate B-22-1 was synthesized according to the same method as a) of Synthesis Example 4 by using 1 equivalent of 2,4-dichloro-6-phenyltriazine and 0.9 equivalent of dibenzofuran-2-boronic acid.

a) Synthesis of Intermediate B-25-1

Intermediate B-25-1 was synthesized according to the same method as a) of Synthesis Example 4 by using 1 equivalent of 2,4-dichloro-6-phenyltriazine and 0.9 equivalent of dibenzofuran-1-boronic acid.

b) Synthesis of Compound B-25

Compound B-25 was synthesized according to the same method as Synthesis Example 6 by using Intermediate B-25-1 and 9-(3-(4,4,5,5-tetramethyl-1,3,2-dioxaborolan-2-yl)-phenyl)-carbazole (CAS: 870119-58-7) respectively by 1.0 equivalent.

LC/MS calculated for: $C_{39}H_{24}N_4O$ Exact Mass: 564.1950 found for: 565.20.

(Preparation of Second Host)

Synthesis Example 15: Synthesis of Compound D-129

[Reaction Scheme 15]

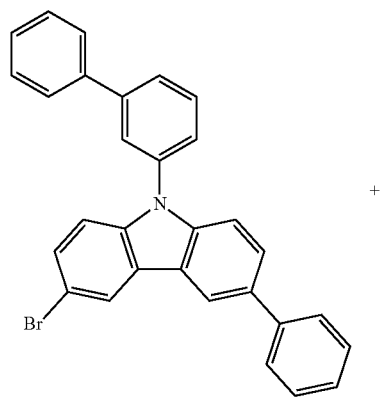

+

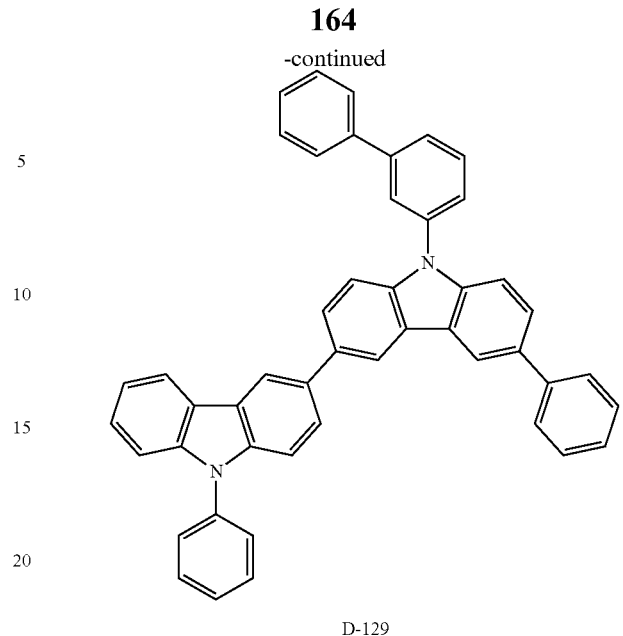

D-129

20.00 g (42.16 mmol) of 3-bromo-6-phenyl-N-metabiphenylcarbazole, 17.12 g (46.38 mmol) of N-phenylcarbazole-3-boronic ester were added to 175 mL of tetrahydrofuran:toluene (1:1) and 75 mL of a 2 M-potassium carbonate aqueous solution under a nitrogen atmosphere in a 500 mL round-bottomed flask equipped with an agitator, 1.46 g (1.26 mmol) of tetrakis(triphenylphosphine) palladium (0) was added thereto, and the mixture was heated and refluxed under a nitrogen atmosphere for 12 hours. When the reaction was complete, the reactant was poured into methanol, a solid therein was filtered, washed with water and methanol, and dried. A resulting material obtained therefrom was heated and dissolved in 700 mL of chlorobenzene, the solution was silica gel-filtered to completely remove the solvent, and a solid therefrom was heated and dissolved in 400 mL of chlorobenzene and recrystallized to obtain 18.52 g of Compound D-129 (a yield of 69%).

LC/MS calculated for: $C_{42}H_{32}N_2$ Exact Mass: 636.2565 found for: 636.27.

Synthesis Example 16: Synthesis of Compound D-137

[Reaction Scheme 16]

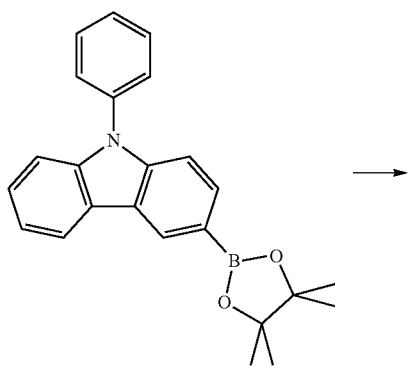 → 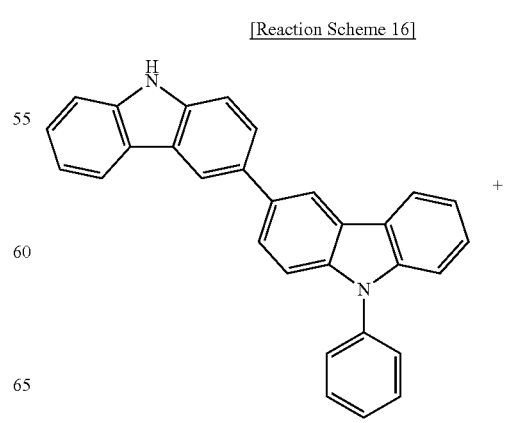 +

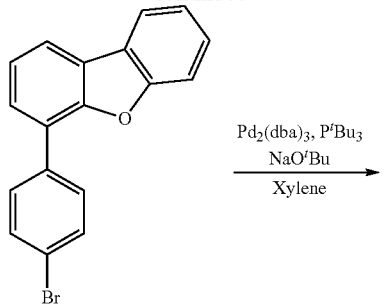

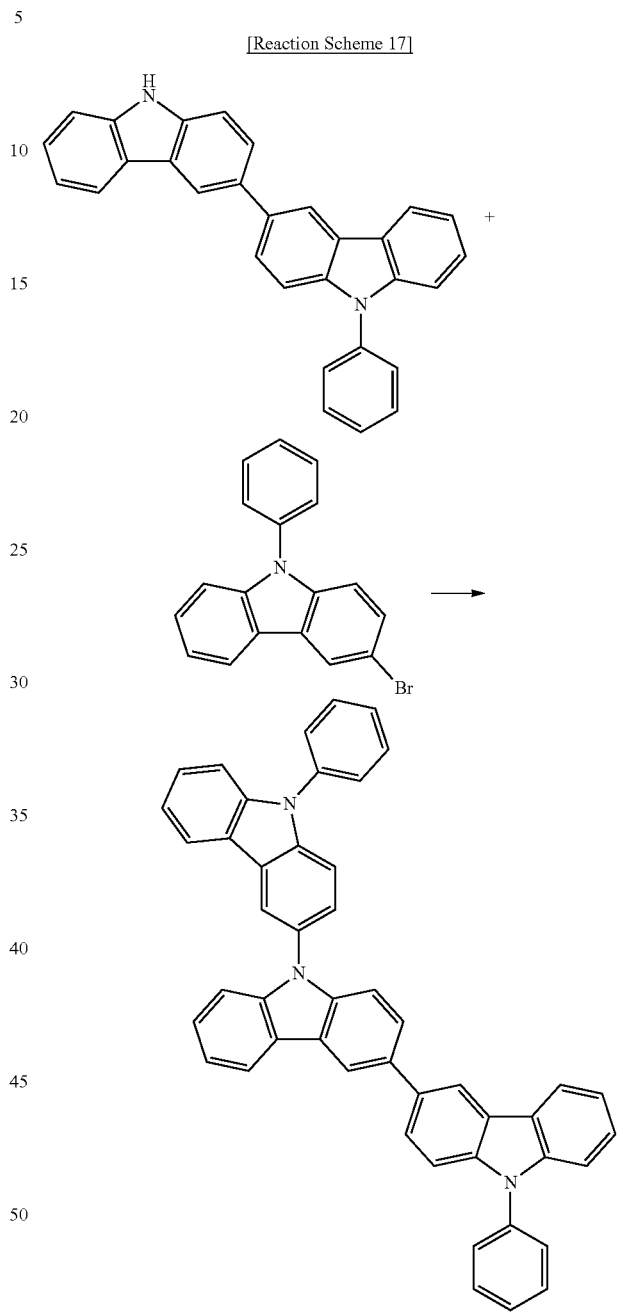

Synthesis Example 17: Synthesis of Compound D-40

[Reaction Scheme 17]

D-40

6.3 g (15.4 mmol) of N-phenyl-3,3-bicarbazole, 5.0 g (15.4 mmol) of 4-(4-bromophenyl)dibenzo[b,d]furan, 3.0 g (30.7 mmol) of sodium t-butoxide, 0.9 g (1.5 mmol) of tris(dibenzylideneacetone)dipalladium, and 1.2 mL of tri t-butylphosphine (50% in toluene) were mixed in 100 mL of xylene in a 250 mL round flask, and the mixture was heated and refluxed under a nitrogen atmosphere for 15 hours. 300 mL of methanol was added to the obtained mixture to crystallize a solid, the solid was filtered, dissolved in dichlorobenzene, filtered with silica gel/Celite, and after removing some of the organic solvent, recrystallized with methanol to obtain Intermediate D-137 (7.3 g, a yield of 73%).

LC/MS calculated for: $C_{48}H_{30}N_2O$ Exact Mass: 650.2358 found for: 650.24.

1 equivalent of N-phenyl-3,3-bicarbazole and 1 equivalent of 3-bromo-9-phenylcarbazole along with 1.5 equivalent of sodium t-butoxide, 0.03 equivalent of tris(dibenzylideneacetone)dipalladium, and 0.06 equivalent of tri t-butylphosphine were mixed with xylene (0.3 M) in a 250 mL round flask, and the mixture was heated and refluxed under a nitrogen atmosphere for 15 hours. The obtained mixture was added to 300 mL of methanol to crystallize a solid, and the solid was filtered, dissolved in dichlorobenzene with silica gel/Celite, and after removing some of the organic solvent, recrystallized with methanol to obtain Compound D-40 at a yield of 60%.

LC/MS calculated for: $C_{48}H_{31}N_3$ Exact Mass: 649.2518 found for: 649.25.

(Preparation of Phosphorescent Dopant)

Synthesis Example 18: Synthesis of Compound E-24

Dopant Compound E-24 was prepared according to the following Reaction Scheme 18.

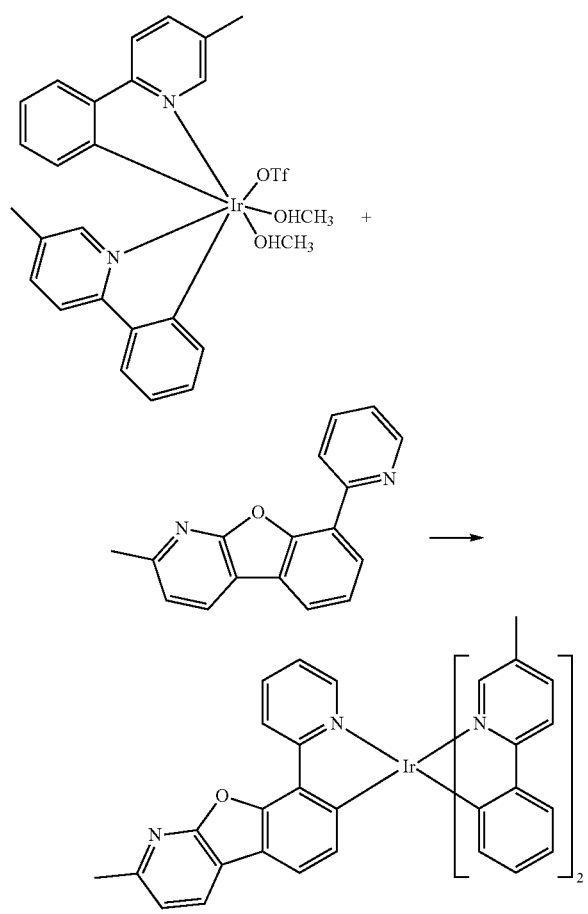

(Manufacture of Organic Light Emitting Diode)

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to form a 50 Å thick layer on the hole injection layer and Compound C was deposited to form a 1,020 Å thick layer and together form a hole transport layer (HTL). On the hole transport layer, a 400 Å-thick light emitting layer was formed by vacuum-depositing Compound C-1 as a first host and Compound D-99 as a second host and 10 wt % of Compound E-24 as a phosphorescent dopant. Herein, Compound C-1 and Compound D-99 were used in a weight ratio of 3:7, but their ratio in the following Examples was separately provided. Subsequently, on the light emitting layer, a 300 Å-thick electron transport layer was formed by simultaneously vacuum-depositing the compound D and Liq in a ratio of 1:1, and on the electron transport layer, Liq and Al were sequentially vacuum-deposited to be 15 Å thick and 1,200 Å thick to manufacture an organic light emitting diode.

The organic light emitting diode had a multi-layered organic thin layer. The organic light emitting diode had a structure of ITO/Compound A (700 Å)/Compound B (50 Å)/Compound C (1,020 Å)/EML [Compound C-1:Compound D-99:Compound E-24 (10 wt %)] (400 Å)/Compound D:Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinolone

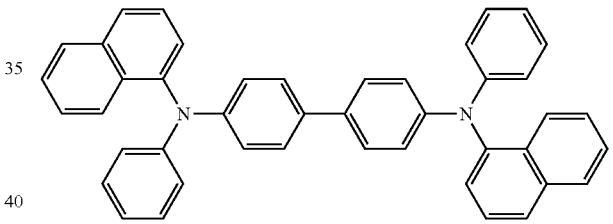

[NPB]

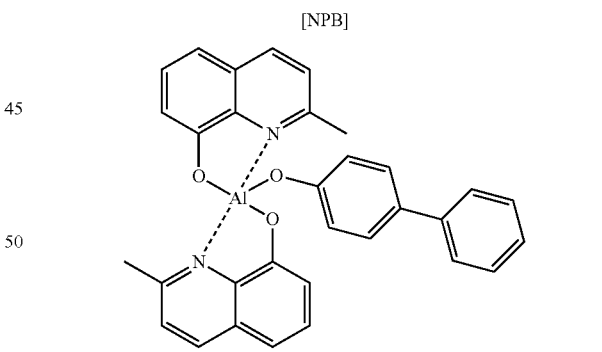

[BAlq]

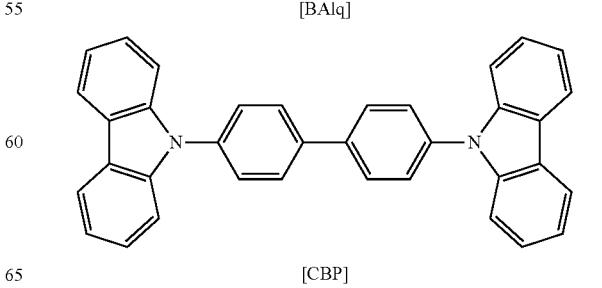

[CBP]

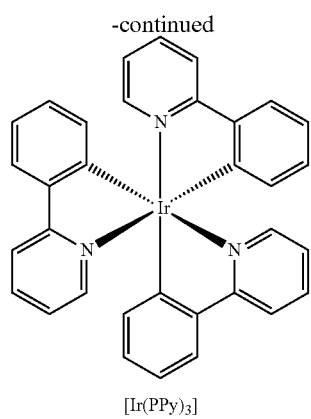

[Ir(PPy)₃]

Examples 2 to 23 and Comparative Examples 1 to 6

Each organic light emitting diode was manufactured according to the same method as Example 1 except for changing the composition of the first host, the second host, and the phosphorescent dopant in each composition shown in Table 1.

Evaluation 1: Luminous Efficiency and Life-Span Increase Effect

Luminous efficiency and life-span characteristics of the organic light emitting diodes according to Examples 1 to 23 and Comparative Examples 1 to 6 were evaluated. The measurements were specifically performed in the following methods, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) was calculated by using the luminance, current density, and voltages (V) from items (1) and (2), above.

(4) Measurement of Life-Span

T90 life-spans of the organic light emitting diodes according to Examples 1 to 24 and Comparative Examples 1 to 6 were measured as a function of time when their luminance decreased down to 90% relative to the initial luminance (cd/m$^2$) after emitting light with 5,000 cd/m$^2$ as the initial luminance (cd/m$^2$) and measuring the decrease in luminance over time with a Polanonix life-span measurement system.

(5) Measurement of Driving Voltage

A driving voltage of each diode was measured using a current-voltage meter (Keithley 2400) at 15 mA/cm$^2$.

TABLE 1

| | First host | Second host | Ratio of first and second hosts | Dopant | Color | Efficiency Cd/A | Life-span T90 | Driving voltage (Vd) |
|---|---|---|---|---|---|---|---|---|
| Comparative Example 1 | C-1 | — | alone | E-24 | green | 56 | 30 | 4.1 |
| Comparative Example 2 | C-1 | CBP | 3:7 | E-24 | green | 61 | 60 | 4.8 |
| Example 1 | C-1 | D-99 | 3:7 | E-24 | green | 70 | 600 | 3.9 |
| Comparative Example 3 | C-1 | D-99 | 3:7 | Ir(ppy)₃ | green | 49 | 220 | 4.2 |
| Comparative Example 4 | C-22 | — | alone | E-24 | green | 53 | 40 | 4.0 |
| Comparative Example 5 | C-22 | CBP | 3:7 | E-24 | green | 60 | 80 | 4.7 |
| Example 2 | C-22 | D-99 | 3:7 | E-24 | green | 71 | 640 | 3.9 |
| Comparative Example 6 | C-22 | D-99 | 3:7 | Ir(ppy)₃ | green | 49 | 240 | 4.3 |
| Example 3 | C-1 | D-40 | 3:7 | E-24 | green | 69 | 380 | 3.7 |
| Example 4 | C-22 | D-40 | 3:7 | E-24 | green | 70 | 420 | 3.7 |
| Example 5 | C-1 | D-137 | 3:7 | E-24 | green | 68 | 580 | 4.2 |
| Example 6 | C-22 | D-137 | 3:7 | E-24 | green | 67 | 620 | 4.3 |
| Example 7 | C-1 | D-31 | 3:7 | E-24 | green | 72 | 620 | 4.1 |
| Example 8 | C-22 | D-31 | 3:7 | E-24 | green | 72 | 700 | 4.2 |
| Example 9 | C-1 | D-129 | 3:7 | E-24 | green | 69 | 600 | 4.2 |
| Example 10 | C-22 | D-129 | 3:7 | E-24 | green | 67 | 610 | 4.4 |
| Example 11 | C-2 | D-99 | 3:7 | E-24 | green | 71 | 590 | 4.0 |
| Example 12 | C-12 | D-99 | 3:7 | E-24 | green | 67 | 580 | 3.8 |
| Example 13 | C-16 | D-99 | 3:7 | E-24 | green | 69 | 650 | 3.8 |
| Example 14 | C-17 | D-99 | 3:7 | E-24 | green | 69 | 570 | 3.9 |
| Example 15 | C-21 | D-99 | 3:7 | E-24 | green | 67 | 550 | 3.9 |
| Example 16 | C-22 | D-99 | 3:7 | E-24 | green | 69 | 620 | 4.0 |
| Example 17 | C-25 | D-99 | 3:7 | E-24 | green | 72 | 650 | 4.0 |
| Example 18 | B-1 | D-99 | 3:7 | E-24 | green | 68 | 410 | 4.2 |
| Example 19 | B-13 | D-99 | 3:7 | E-24 | green | 67 | 350 | 4.3 |
| Example 20 | B-17 | D-99 | 3:7 | E-24 | green | 67 | 370 | 4.1 |
| Example 21 | B-14 | D-99 | 3:7 | E-24 | green | 65 | 380 | 4.2 |
| Example 22 | B-14 | D-31 | 3:7 | E-24 | green | 66 | 440 | 4.3 |
| Example 23 | B-25 | D-31 | 3:7 | E-24 | green | 65 | 310 | 4.5 |

Referring to Table 1, when a material including DBX (e.g., dibenzofuran or dibenzothiophene) and carbazole was used as a first host, and biscarbazole was used as a second host, an advantage in terms of driving voltage and life-span was obtained, compared with when the first host was used alone or when CBP was used as the second host. In addition, when Ir(ppy)$_3$ as a phosphorescent dopant not including a DBX moiety was used, the life-span and efficiency were largely increased, compared with when Compound E-24 as a phosphorescent dopant including a DBX moiety was used. For example, when the structure of directly linking a position No. 3 of dibenzofuran with triazine as the first host was used, driving voltage decreased with an increase in life-span.

By way of summation and review, performance of an organic light emitting diode may be affected by characteristics of the organic layer, and among them, may be mainly affected by characteristics of an organic material of the organic layer.

For example, an organic material being capable of increasing hole and electron mobility and simultaneously increasing electrochemical stability may be developed so that the organic light emitting diode may be applied to a large-size flat panel display.

The embodiments may provide an organic optoelectronic device having high efficiency and long life-span.

The embodiments may provide a display device including the organic optoelectronic device.

DESCRIPTION OF SYMBOLS

100, 200: organic light emitting diode
105: organic layer
110: cathode
120: anode
130: light emitting layer
140: hole auxiliary layer Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic optoelectronic device, comprising:
   an anode and a cathode facing each other; and
   an organic layer between the anode and the cathode,
   wherein:
   the organic layer includes a light emitting layer and at least one of a hole injection layer, a hole transport layer, and an electron transport layer,
   the light emitting layer includes a first host compound represented by Chemical Formula 1-3a-I or Chemical Formula 1-4a-I and a second host represented by Chemical Formula 2:

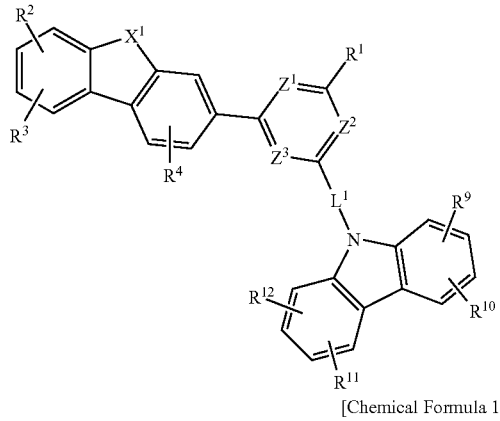

[Chemical Formula 1-3a-I]

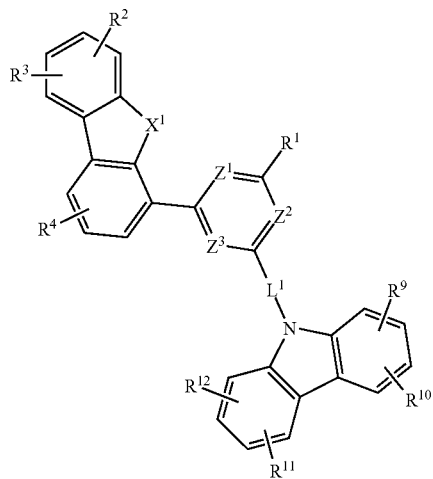

[Chemical Formula 1-4a-I]

in Chemical Formulae 1-3a-I and 1-4a-I,
$X^1$ is O or S,
$Z^1$ to $Z^3$ are each independently N or $CR^a$,
at least two of $Z^1$ to $Z^3$ are N,
$L^1$ is a single bond, or a substituted or unsubstituted C6 to C20 arylene group,
$R^1$ is a substituted or unsubstituted C6 to C20 aryl group, a substituted or unsubstituted dibenzofuranyl group, or a substituted or unsubstituted dibenzothiophenyl group, and
$R^a$, $R^2$ to $R^4$ and $R^9$ to $R^{13}$ are independently hydrogen, deuterium, a cyano group, a substituted or unsubstituted C1 to C10 alkyl group, or a substituted or unsubstituted C6 to C20 aryl group,

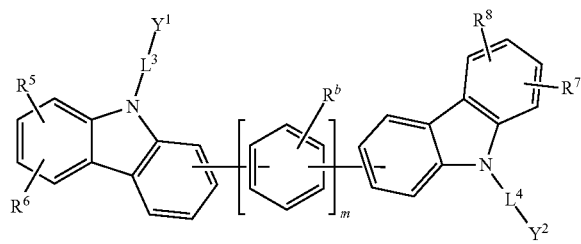

[Chemical Formula 2]

in Chemical Formula 2,

Y$^1$ and Y$^2$ are each independently a substituted or unsubstituted C6 to C20 aryl group or a substituted or unsubstituted C2 to C30 heterocyclic group, L$^3$ and L$^4$ are each independently a single bond or a substituted or unsubstituted C6 to C20 arylene group, R$^b$ and R$^5$ to R$^8$ are each independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group, and m is an integer ranging from 0 to 2.

2. The organic optoelectronic device as claimed in claim 1, wherein, in Chemical Formulae 1-3a-I and 1-4a-I, Z$^1$ to Z$^3$ are N.

3. The organic optoelectronic device as claimed in claim 1, wherein, in Chemical Formulae 1-3a-I and 1-4a-I,
R$^1$ is a substituent of Group I:

[Group 1]

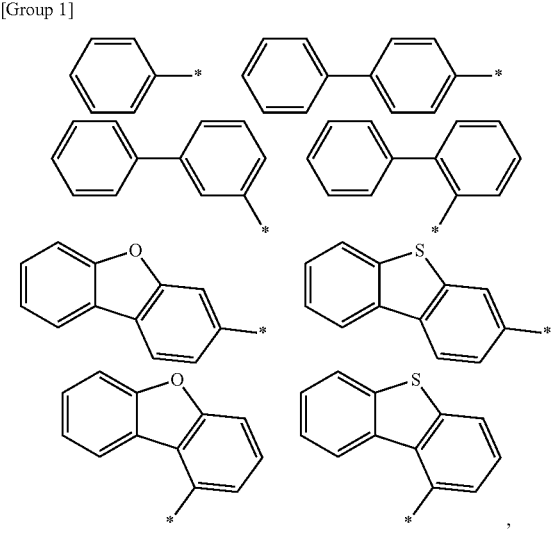

and in Group I, * is a linking point.

4. The organic optoelectronic device as claimed in claim 1, wherein, in Chemical Formulae 1-3a-I and 1-4a-I, L$^1$ is a single bond, a C6 arylene group, a C12 arylene group or a C18 arylene group.

5. The organic optoelectronic device as claimed in claim 1, wherein, in Chemical Formulae 1-3a-I and 1-4a-I, L$^1$ is a single bond, or an unsubstituted C6 arylene group.

6. The organic optoelectronic device as claimed in claim 1, wherein, in Chemical Formulae 1-3a-I and 1-4a-I, R$^1$ is an unsubstituted C6 aryl group.

7. The organic optoelectronic device as claimed in claim 1, wherein:

the compound is represented by Chemical Formula 1-3a-I, and in Chemical Formula 1-4a-I, X$^1$ is O, Z$^1$ to Z$^3$ are each N, L$^1$ is a single bond, or an unsubstituted C6 arylene group, R$^1$ is an unsubstituted C6 aryl group, and R$^2$ to R$^4$ and R$^9$ to R$^{13}$ are each hydrogen.

8. The organic optoelectronic device as claimed in claim 1, wherein:

Chemical Formula 2 includes a moiety of Group II, and

*-L$^3$-Y$^1$ and *-L$^4$-Y$^2$ are each independently a substituent of Group III:

[Group II]

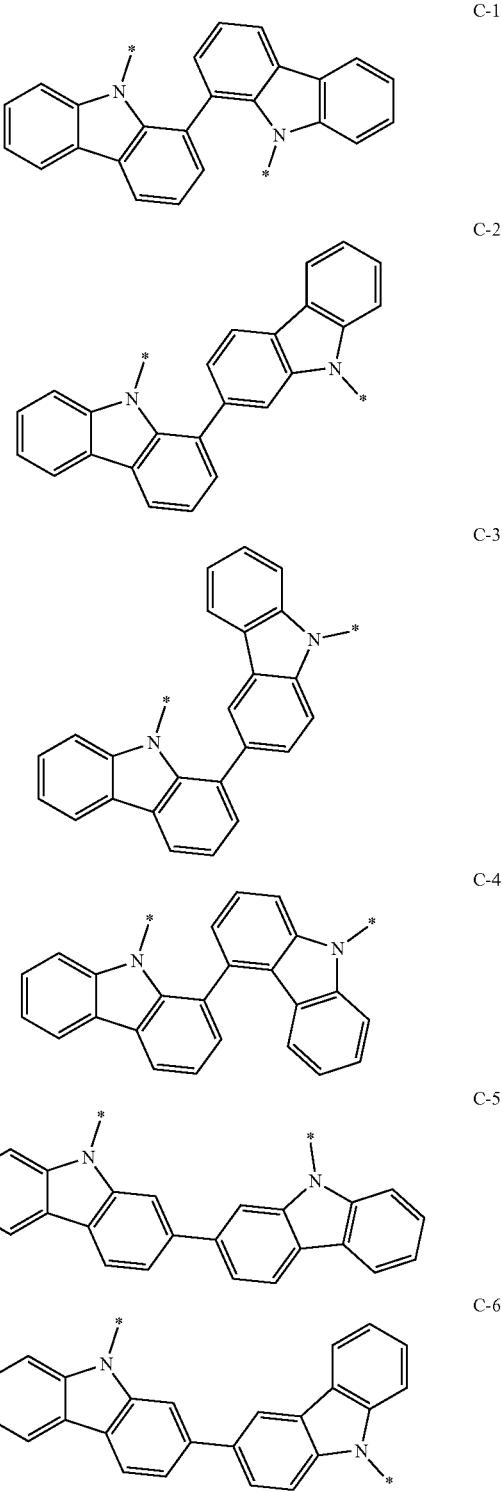

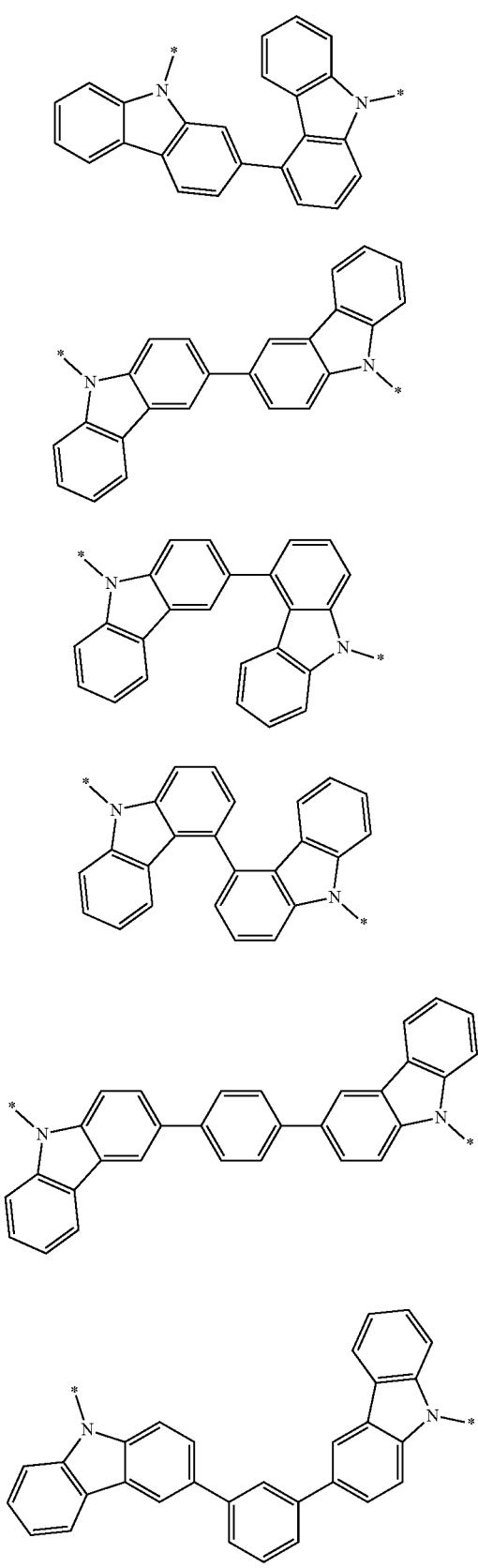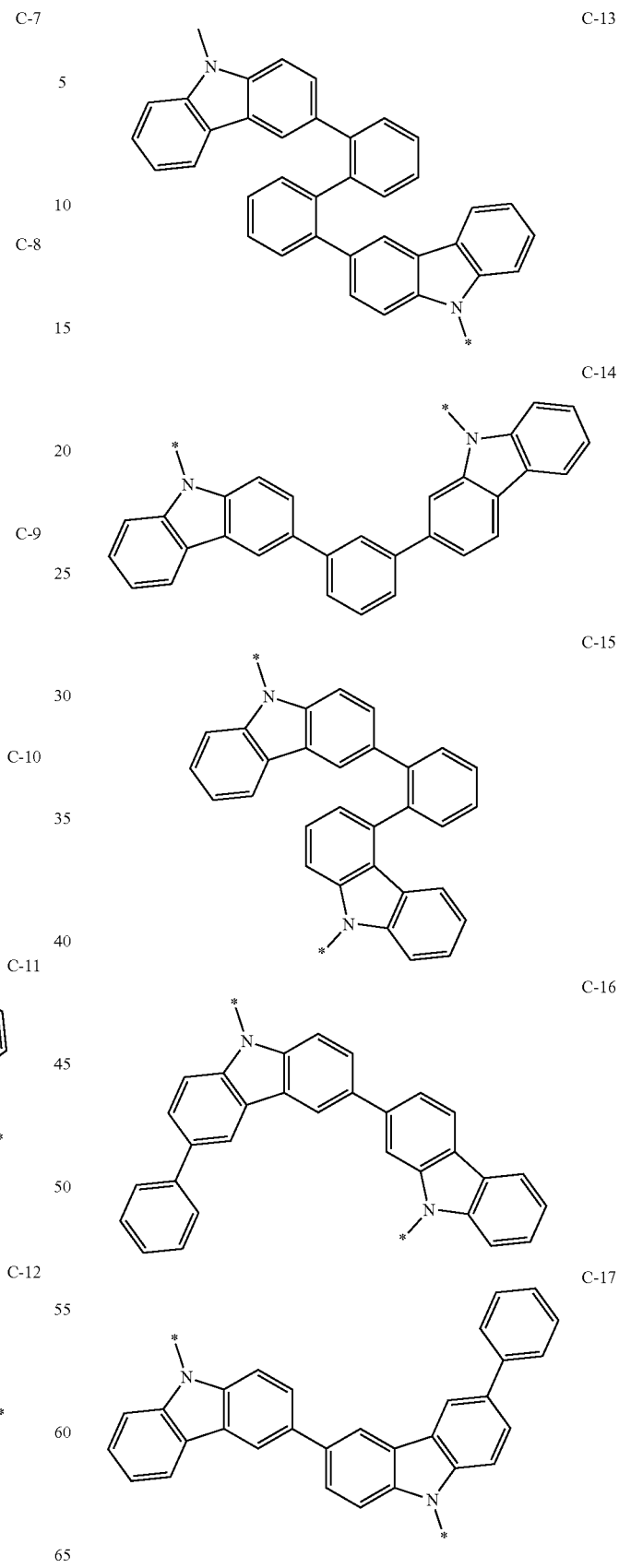

C-18
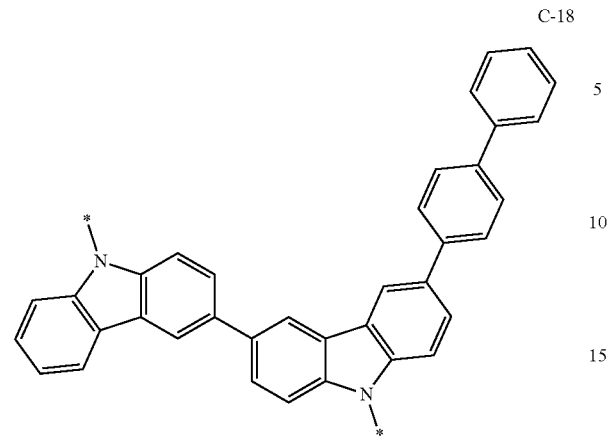
[Group III]
B-1
B-2
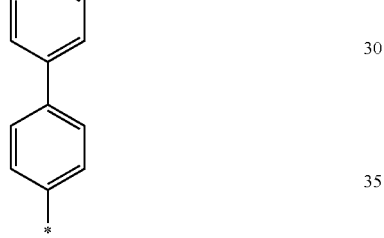
B-3
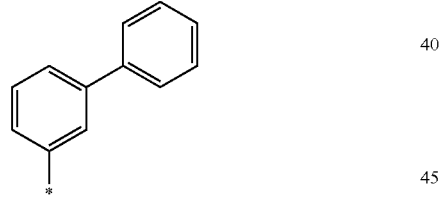
B-4
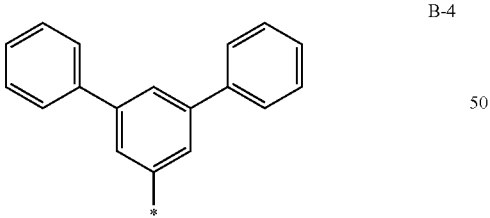
B-5
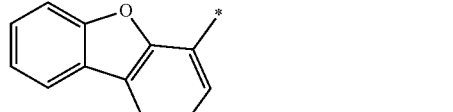
B-6
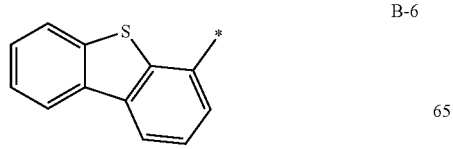
B-7
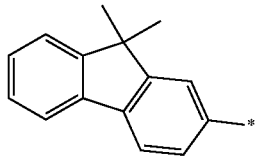
B-8
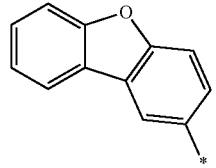
B-9
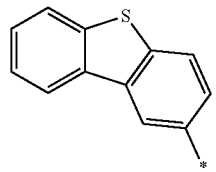
B-10
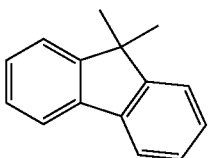
B-11
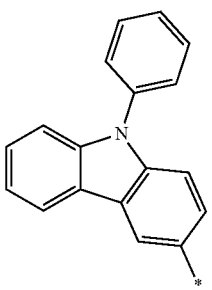
B-12
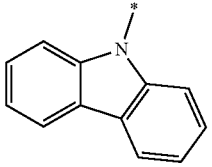
B-13
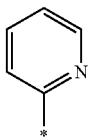
B-14
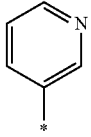

-continued
B-15
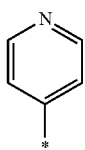
B-16
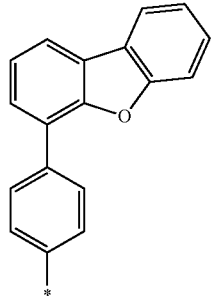
B-17
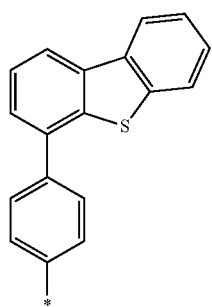
B-18
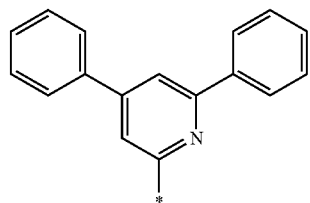
B-19
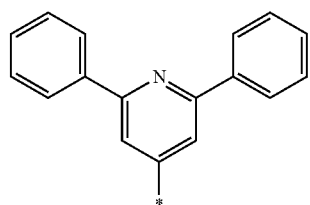
B-20
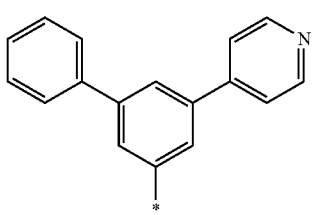
B-21
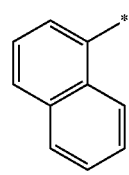
-continued
B-22
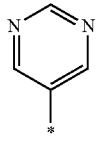
B-23
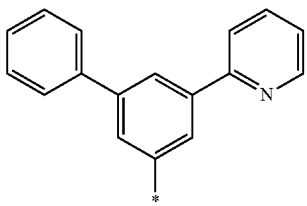
B-24
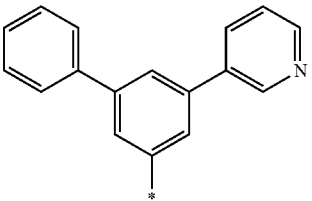
B-25
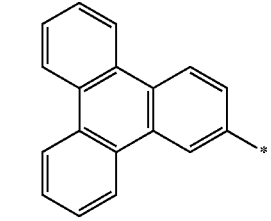
B-26
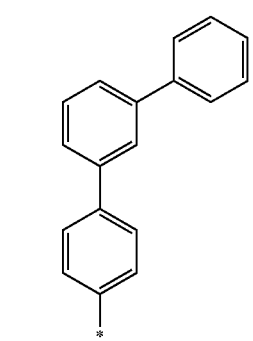
B-27
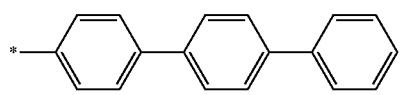
B-28
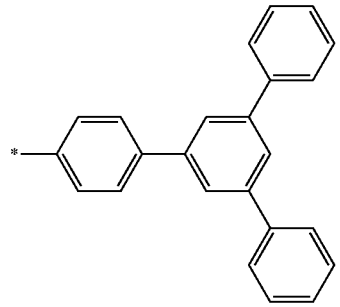
wherein, in Group II and Group III, * is a linking point.
9. The organic optoelectronic device as claimed in claim 8, wherein:

Chemical Formula 2 includes a moiety represented by Chemical Formula c-8 or Chemical Formula c-17 of Group II, and \*-$L^3$-$Y^1$ and \*-$L^4$-$Y^2$ are each independently a substituent of Group III.

10. The organic optoelectronic device as claimed in claim 8, wherein:

Chemical Formula 2 includes a moiety represented by Chemical Formula c-8 or Chemical Formula c-17 of Group II, and \*-$L^3$-$Y^1$ and \*-$L^4$-$Y^2$ are each independently a substituent represented by B-1, B-2, B-3, B-11, B-16, or B-17 of Group III.

11. The organic optoelectronic device as claimed in claim 1, wherein the second host represented by Chemical Formula 2 is represented by Chemical Formula 2A:

[Chemical Formula 2A]

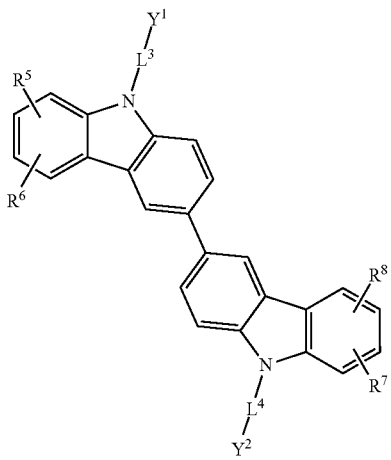

wherein, in Chemical Formula 2A, $L^3$ and $L^4$ are each independently a single bond, or a substituted or unsubstituted C6 to C20 arylene group, $R^a$ and $R^2$ to $R^8$ are each independently hydrogen, deuterium, a cyano group, a substituted or unsubstituted C1 to C10 alkyl group, or a substituted or unsubstituted C6 to C20 aryl group, and $Y^1$ and $Y^2$ are each independently a substituted or unsubstituted C6 to C20 aryl group, or a substituted or unsubstituted C2 to C30 heterocyclic group.

12. The organic optoelectronic device as claimed in claim 1, wherein, in Chemical Formula 2, m is 0, $Y^1$ and $Y^2$ are each an unsubstituted C6 aryl group, $L^3$ and $L^4$ are each an unsubstituted C6 arylene group, $R^5$ to $R^8$ are each hydrogen.

13. The organic optoelectronic device as claimed in claim 1, wherein the second host represented by Chemical Formula 2 is the following compound D-99:

D-99

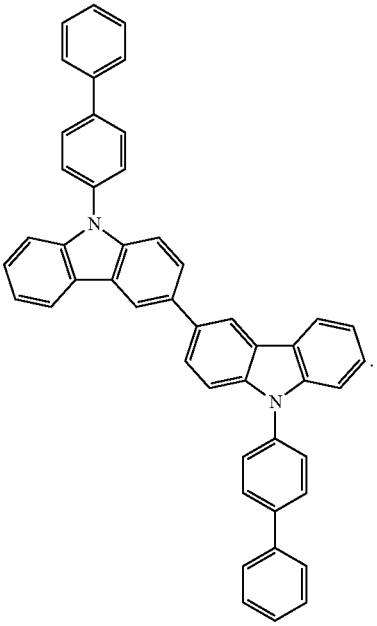

14. A display device comprising the organic optoelectronic device as claimed in claim 1.

\* \* \* \* \*